US010591466B2

(12) United States Patent
Prehaud et al.

(10) Patent No.: US 10,591,466 B2
(45) Date of Patent: Mar. 17, 2020

(54) IN VITRO BLOOD-BRAIN BARRIER MODEL

(71) Applicants: INSTITUT PASTEUR, Paris (FR); INSTITUT NATIONAL DE LA SANTE ET DE LA RECHERCHE MEDICALE, Paris (FR)

(72) Inventors: Christophe Prehaud, Guyancourt (FR); Monique Lafon, Paris (FR); Pierre-Emmanuel Ceccaldi, Boissise la Bertrand (FR); Philippe Afonso, Montrouge (FR); Pierre Lafaye, Malakoff (FR)

(73) Assignees: INSTITUT PASTEUR, Paris (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 157 days.

(21) Appl. No.: 15/508,488

(22) PCT Filed: Sep. 9, 2015

(86) PCT No.: PCT/EP2015/070671
§ 371 (c)(1),
(2) Date: Mar. 2, 2017

(87) PCT Pub. No.: WO2016/038123
PCT Pub. Date: Mar. 17, 2016

(65) Prior Publication Data
US 2017/0241988 A1 Aug. 24, 2017

(30) Foreign Application Priority Data
Sep. 9, 2014 (EP) .................................... 14306389

(51) Int. Cl.
*G01N 33/50* (2006.01)
*C12N 5/079* (2010.01)
*C12M 1/00* (2006.01)
*C12M 1/12* (2006.01)
*C12N 5/071* (2010.01)
*C12M 3/00* (2006.01)

(52) U.S. Cl.
CPC ......... *G01N 33/5082* (2013.01); *C12M 21/08* (2013.01); *C12M 23/34* (2013.01); *C12M 25/02* (2013.01); *C12M 29/04* (2013.01); *C12N 5/069* (2013.01); *C12N 5/0622* (2013.01); *C12N 5/0691* (2013.01); *G01N 33/5014* (2013.01); *G01N 33/5058* (2013.01); *G01N 33/5064* (2013.01); *C12N 2502/28* (2013.01)

(58) Field of Classification Search
None
See application file for complete search history.

(56) References Cited

U.S. PATENT DOCUMENTS 8,460,888 B2 6/2013 Lafaye et al.
2014/0127800 A1 5/2014 Shusta et al.

FOREIGN PATENT DOCUMENTS

| EP | 2239330 A1 | 10/2010 |
|---|---|---|
| WO | 02/057445 A1 | 7/2002 |
| WO | 2009/004495 A2 | 1/2009 |
| WO | 2013/068430 A2 | 5/2013 |
| WO | 2013/086329 A1 | 6/2013 |
| WO | 2016/038122 A1 | 3/2016 |

OTHER PUBLICATIONS

Joana Bicker, et al., "Blood-brain barrier models and their relevance for a successful development of CNS drug delivery systems: A review," Eur. J. Pharm. Biopharm. (2014), http://dx.doi.org/10.1016/j.ejpb.2014.03.012.
Da Fonseca, ACC, et al., (2014) The impact of microglial activation on blood-brain barrier in brain diseases. Front. Cell. Neurosci. 8:362. doi: 10.3389/fncel.2014.00362.
Maxime Culot, et al., "An in vitro blood-brain barrier model for high throughput (HTS) toxicological screening," Toxicology in Vitro 22 (2008) 799-811.
Marie-Pierre Dehouck, et al., "An Easier, Reproducible, and Mass-Productoin Method to Study the Blood-Brain Barrier In Vitro," Journal of Neuroscience, vol. 54, No. 5 (1990) pp. 1798-1801.
Laurence Descamps, et al., "Protective Effect of Glial Cells Against Lipopolysaccharide-Mediated Blood-Brain Barrier Injury," GLIA 42:46-58 (2003).
Ailing Fu, et al., "Targeted Delivery of Proteins into the Central Nervous System Mediated by Rabies Virus Glycoprotein-Derived Peptide," Pharm Res (2012) 29:1562-1569.
Nazila Janabi, et al., "Establishment of human microglial cell lines after transfection of primary cultures of embryonic microglial cells with the SV40 large T antigen," Neuroscience Letters 195 (1995) 105-108.
Tengfei Li, Jean-Pierre Bourgeois, Susanna Celli, et al.,"Cell-penetrating anti-GFAP VHH and corresponding fluorescent fusion protein VHH-GFP spontaneously cross the blood-brain barrier and specifically recognize astrocytes: application to brain imaging," FASEB J 2012 26: 3969-3979.
Lippmann et al.: Modeling the blood-brain barrier using stem cell sources. Fluids and Barriers of the CNS 2013 10:2.

(Continued)

*Primary Examiner* — Blaine Lankford
(74) *Attorney, Agent, or Firm* — Arrigo, Lee, Guttman & Mouta-Bellum LLP

(57) ABSTRACT

The invention is in the domain of delivery of molecules to brain cells across the blood-brain barrier. The invention relates to a novel polypeptide-based carrier that allows the efficient delivery of an effector peptide, to neuron cells across the blood-brain barrier, and to methods for the production and testing of such carrier, including a model for testing the capacity of such molecule to cross the blood-brain barrier and/or the toxicity of molecules on the blood brain barrier and/or the capacity of molecules that have crossed to target human brain cells (e/g. neurons, astrocytes and microglial cells).

18 Claims, 14 Drawing Sheets
Specification includes a Sequence Listing.

(56) References Cited

OTHER PUBLICATIONS

Arumugam Muruganandam, et al., "Selection of phage-displayed llama single-domain antibodies that transmigrate across human blood-brain barrier endothelium," The FASEB Journal express article 10.1096/fj.01-0343fje. Published online Dec. 28, 2001.

Shinsuke Nakagawa, et al., "A new blood-brain barrier model using primary rat brain endothelial cells, pericytes and astrocytes," Neurochemistry International 54 (2009) 253-263.

Francois Paquet-Durand, et al., "Turning teratocarcinoma cells into neurons: rapid differentiation of NT-2 cells in floating spheres," Developmental Brain Research 142 (2003) 161-167.

Claire Perruchini, et al., "Llama VHH antibody fragments against GFAP: better diffusion in fixed tissues than classical monoclonal antibodies," Acta Neuropathol (2009) 118:685-695.

Birk Poller, et al., Journal of Neurochemistry,"The human blood endothelial cell line . . . ," vol. 107, pp. 1358-1368 (2008).

Noriko Sumi, et al., "Lipopolysaccharide-Activated Microglia Induce Dysfunction of the Blood-Brain Barrier in Rat Microvascular Endothelial Cells Co-Cultured with Microglia," Cell Mol Neurobiol (2010) 30:247-253.

B. B. Weksler, et al., "Blood-brain barrier-specific properties of a human adult brain endothelial cell line," The FASEB Journal express article 10.1096/fj.04-3458fje. Published online Sep. 1, 2005.

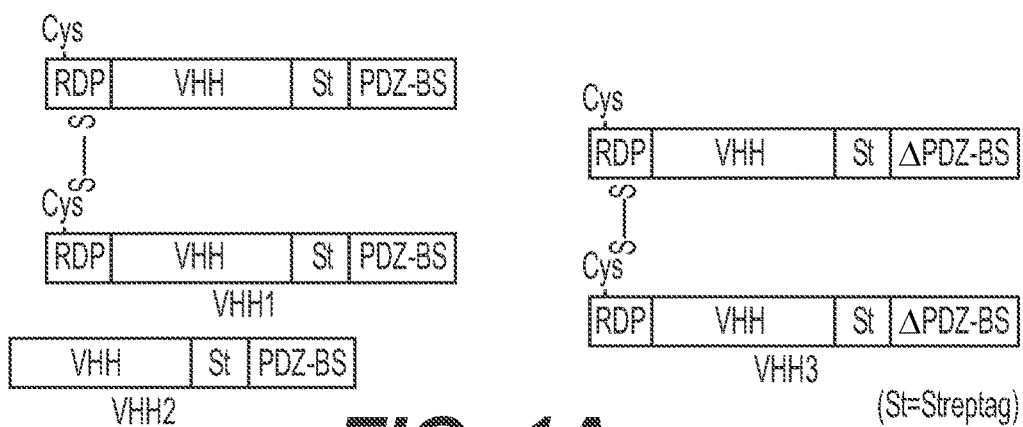
FIG. 1A
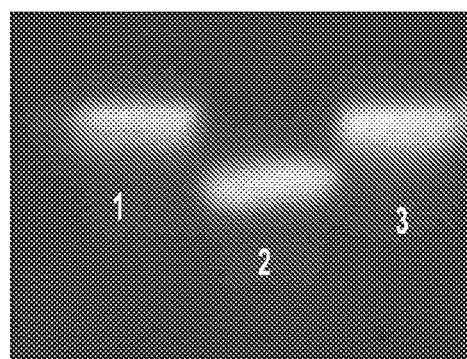
FIG. 1B
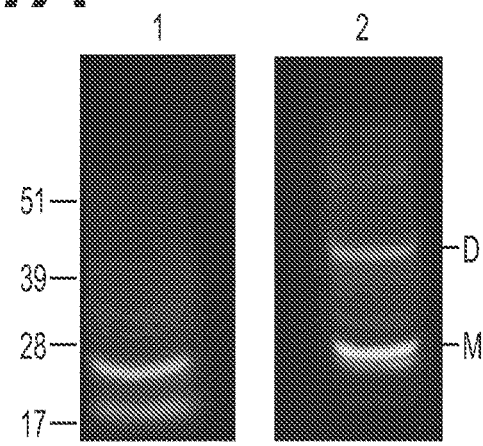
FIG. 1C
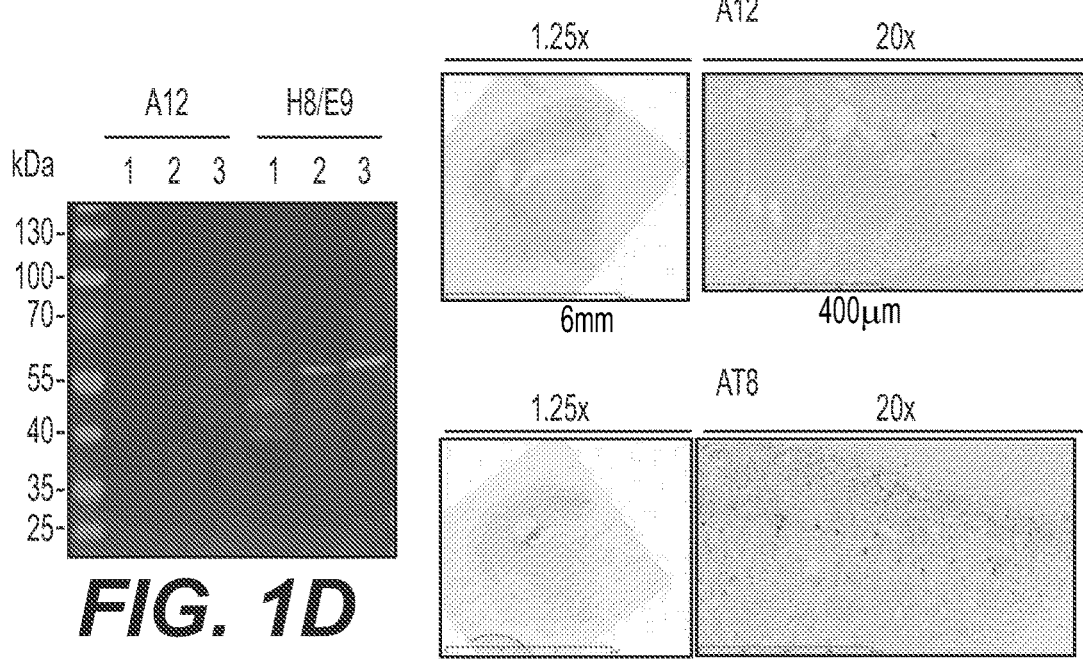
FIG. 1D
FIG. 1E

```
EPOP_JA737802      QVQLQESGGGLVQAGGSLRLSCAASGSIFSLNDMGWYRQAPGKQRELVAAITSGGSTNYA  60
EPOP_JA737727      QVQLQESGGGLVQAGGSLRLSCAASGSIFSLNDMGWYRQAPGKQRELVAAITSGGSTNYA  60
NRPL1_NRP_JA737727 QVQLQESGGGLVQAGGSLRLSCAASGSIFSLNDMGWYRQAPGKQRELVAAITSGGSTNYA  60
NRPL2_NRP00429C6B  QVQLQESGGGLVQAGGSLRLSCAASGSIFSLNDMGWYRQAPGKQRELVAAITSGGSTNYA  60
NRPL2_NRP0042A2FC  QVQLQESGGGLVQAGGSLRLSCAASGSIFSLNDMGWYRQAPGKQRELVAAITSGGSTNYA  60
NRPL1_NRP_JA737728 QVQLQESGGGLVQAGGFLRLSCAASGSIFSLNDMGWYRQAPGKQRELVAAITSGGSTNYA  60
EPOP_JA737803      QVQLQESGGGLVQAGGPLRLSCAASGSIFSLNDMGWYRQAPGKQRELVAAITSGGSTNYA  60
EPOP_JA737728      QVQLQESGGGLVQAGGPLRLSCAASGSIFSLNDMGWYRQAPGKQRELVAAITSGGSTNYA  60
NRPL2_NRP0042909A  QVQLQESGGGLVQAGGSLRLSCAASGSIFSLNDMGWYRQAPGKQRELVAAISSGGRLNYA  60
NRPL1_NRP_JA737730 QVQLQESGGGLVQFGGSLRLSCAASGSIFSLNDMGWYRQAPGKQRELVAAISSGGRLNYA  60
EPOP_JA737805      QVQLQESGGGLVQPGGSLRLSCAASGSIFSLNDMGWYRQAPGKQRELVAAITSGGRLNYA  60
EPOP_JA737730      QVQLQESGGGLVQAGGSLRLSCAASGSIFSLNDMGWYRQAPGKQRELVAAITSGGSTNYA  60
NRPL2_NRP00429FF4  QVQLQESGGGLVQAGGSLRLSCAASGSIFSLNDMGWYRQAPGKQRELVAAITSGRSTNYA  60
NRPL1_NRP_JA737736 QVQLQESGGGLVQAGGSLRLSCAASGSIFSLNDMGWYRQAPGKQRELVAAITSGRSTNYA  60
EPOP_JA737811      QVQLQESGGGLVQAGGSLRLSCAASGSIFSLNDMGWYRQAPGKQRELVAAITSGRSTNYA  60
EPOP_JA737736      QVQLQESGGGLVQAGGSLRLSCAASGSIFSLNDMGWYRQAPGKQRELVAAITSGGSTNYA  60
NRPL2_NRP004296A4  QVQLQESGGGLVQAGGSLRLSCAASGSIFSLNDMGWYRQAPGKQRELVAAVTSGGSTNYA  60
NRPL1_NRP_JA737737 QVQLQESGGGLVQAGGSLRLSCAASGSIFSLNDMGWYRQAPGKLRELVAAVTSGGSTNYA  60
EPOP_JA737812      QVQLQESGGGLVQAGGSLRLSCAASGSIFSLNDMGWYRQAPGKLRELVAAVTSGGSTNYA  60
EPOP_JA737737      QVQLQESGGGLVQAGGSLRLSCAASGSIFSLNDMGWYRQAPGKLRELVAAVTSGGSTNYA  60
NRPL2_NRP0042A715  QVQLQESGGGLVQAGGSLRLSCAASGSIFSLNDMGWYRQAPGKLRELVAAITSGGSTKYA  60
NRPL1_NRP_JA737732 QVQLQESGGGLVQAGGSLRLSCAASGSIFSLNDMGWYRQAPGKLRELVAAITSGGSTKYA  60
EPOP_JA737807      QVQLQESGGGLVQAGGSLRLSCAASGSIFSLNDMGWYRQAPGKLRELVAAITSGGSTKYA  60
NRPL1_NRP_JA737733 QVQLQESGGGLVQAGGSLRLSCAASGSIFSLNDMGWYRQAPGKLRELVAAITSGGSTRYA  60
EPOP_JA737808      QVQLQESGGGLVQAGGSLRLSCAASGSIFSLNDMGWYRQAPGKQRDLVAAITSGGSTKYA  60
NRPL2_NRP0042A8E9  QVQLQESGGGLVQAGGSLRLSCAASGSIFSLNDMGWYRQAPGKQRDLVAAITSGGSTKYA  60
NRPL1_NRP_JA737731 QVQLQESGGGLVQAGGSLRLSCAASGSIFSINTMRWYRQAPGKHRELVATITSGGSTNYA  60
NRPL2_NRP003AC89C  QVQLQESGGGLVQAGGSLRLSCAASGSIFSINTMRWYRQAPGKHRELVATITSGGSTKIA  60
NRPL1_NRP_JA381965 QVQLQESGGGLVQAGGSLRLSCAASGSIFSINTMRWYRQAPGKHRELVATITSGGSTNYA  60
EPOP_JA381965      QVQLQESGGGLVQAGGSLRLSCAASGSIFSINSMDWDRQAPGKHRELVATITSGGSTNYA  60
NRPL2_NRP003AFFE2  QVQLQESGGGLVQAGGSLRLSCAASGSIFSINSMDWDRQAPGKQRELVATITSGGSTNYA  60
NRPL1_NRP_JA381850 QVQLQESGGGLVQAGGSLRLSCAASGSIFSINSMDWDRQAPGKQRELVATITSGGSTNYA  60
EPOP_JA381872      QVQLQESGGGLVQAGGSLRLSCAASGSIFSINSMDWDRQAPGKQRELVATITSGGSTNYA  60
EPOP_JA381850      QVQLQESGGGLVQPGGSLMLSCAASGNIFTINRMGWYRQAPGKQRELVAAITSGGNTNYA  60
EPOP_JC104783      QVQLQESGGGLVQPGGSLMLSCAASGNIFTINRMGWYRQAPGKQRELVAAITSGGNTNYA  60
```

FIG. 9

| USPOP_ACE10965 | QVQLQESGGGLVQAGGSLRLSCAASGSISSINVMGWFRQAPGKQRELVASITSGGSTNYA | 60 |
| NRPL2_NRP002147C2 | QVQLQESGGGLVQAGGSLRLSCAASGSISSINVMGWFRQAPGKQRELVASITSGGSTNYA | 60 |
| NRPL1_NRP_ACE10965 | QVQLQESGGGLVQAGGSLRLSCAASGSISSINVMGWFRQAPGKQRELVASITSGGSTNYA | 60 |
| NRPL2_NRP0042A6EF | QVQLQESGGGLVQPGGSLRLSCAASGSIFSINAMGWYRQAPGKQRDLVASITSGGSTNYA | 60 |
| NRPL1_NRP_JA737747 | QVQLQESGGGLVQPGGSLRLSCAASGSIFSINAMGWYRQAPGKQRDLVASITSGGSTNYA | 60 |
| EPOP_JA737822 | QVQLQESGGGLVQPGGSLRLSCAASGSIFSINAMGWYRQAPGKQRDLVASITSGGSTNYA | 60 |
| EPOP_JA737747 | QVQLQESGGGLVQPGGSLRLSCAASGSIFSINAMGWYRQAPGKQRDLVASITSGGSTNYA | 60 |
| NRPL2_NRP00310748 | QVQLQESGGGLVQPGGSLRLSCAASGSIFGINAMGWYRQAPGNQRELVAVITSGGTTTYA | 60 |
| NRPL1_NRP_HC481076 | QVQLQESGGGLVQPGGSLRLSCAASGSIFCINAMGWYRQAPGNQRELVAVITSGGTTTYA | 60 |
| EPOP_HC481076 | QVQLQESGGGLVQPGGSLRLSCAASGSIFGINAMGWYRQAPGNQRELVAVITSGGTTTYA | 60 |
| EPOP_JC104795 | QVQLQESGGGLVQPGGSLRLSCAASGSIFGINAMGWYRQAPGKQRELVALVTGSGRTNLA | 60 |
| NRPL2_NRP0042A44F | QVQLQESGGGLVQPGGSLRLSCAASGSIVSINAMGWYRQAPGKQRELVAAIHSGGSTNYA | 60 |
| NRPL1_NRP_JA737723 | QVQLQESGGGLVQPGGSLRLSCAASGSIFSINTMGWYRQAPGKQRELVAAIHSGGSTNYA | 60 |
| EPOP_JA737798 | QVQLQESGGGLVQPGGSLRLSCAASGSIFSINTMGWYRQAPGKQRELVAAIHSGGSTNYA | 60 |
| EPOP_JA737723 | QVQLQESGGGLVQPGGSLRLSCAASGSIFSINTMGWYRQAPGKQRELVAAIHSGGSTNYA | 60 |
| NRPL2_NRP002CCF96 | QVQLQESGGGLVQPGGSLRLSCAASGSIFSINRMGWYRQAPGKQRELVAAITYGGSTNYA | 60 |
| NRPL2_NRP_HC254852 | QVQLQESGGGLVQPGGSLRLSCAASGSIFSINRMGWYRQAPGKQRELVAAITYGGSTNYA | 60 |
| JPOP_DL500873 | QVQLQESGGGLVQPGGSLRLSCAASGSIFSINRMGWYRQAPGKQRELVAAITYGGSTNYA | 60 |
| EPOP_HC254852 | QVQLQESGGGLVQPGGSLRLSCAASGSIFSINAMGWYRQAPGKQRELVAAISSGGSTNYA | 60 |
| NRPL2_NRP002DD9B4 | QVQLQESGGGLVQPGGSLRLSCAASGSIFSINAMGWYRQAPGKQRELVAAISSGGSTNYA | 60 |
| NRPL1_NRP_HC254854 | QVQLQESGGGLVQPGGSLRLSCAASGSIFSINAMGWYRQAPGKQRELVAAISSGGSTNYA | 60 |
| EPOP_HC254854 | QVQLQESGGGLVQPGGSLRLSCAASGSIFSINAMGWYRQAPGKQRELVAAISSGGSTNYA | 60 |
| NRPL2_NRP002D7845 | QVQLQQSGGGLVQPGGSLRLSCAASGSIFSINAMGWYRQAPGKQRELVAHITSGGSTNYA | 60 |
| NRPL1_NRP_HC252013 | QVQLQQSGGGLVQPGGSLRLSCAASGSIFSINAMGWYRQAPGKQRELVAHITSGGSTNYA | 60 |
| JPOP_DJ998044 | EVQLVESGGGLVQPGGSLRLSCAASGSIFSINAMGWYRQAPGKQRELVAHITSGGSTNYA | 60 |
| EPOP_HC252013 | EVQLVESGGGLVQPGGSLRLSCAASGSIFSINAMGWYRQAPGKQRELVAHITSGGSTNYA | 60 |
| EPOP_JC291691 | EVQLVESGGGLVQPGGSLRLSCAASGSILGINAMGWYRQAPGKQRELVAVINSGGSTNYA | 60 |
| EPOP_JB816376 | EVQLVESGGGLVQPGGSLRLSCAASGSIFSFNAMAWYRQAPGKQRELVAAISSGGSTNYA | 60 |
| EPOP_JC984531 | QVQLQESGGGLVQPGGSLRLSCAASGTIFSIKTMGWYRQAPGKQRELVATISNGGSTNYA | 60 |
| NRPL2_NRP000483DA | EVQLVESGGGLVQPGGSLRLSCAASGSIFRINTMAWYRQAPGKQRELVATITNGGNTNYA | 60 |
| NRPL1_NRP_CS585372 | EVQLVESGGGLVQPGGSLRLSCAASGSIFRINTMAWYRQAPGKQRELVATITNGGNTNYA | 60 |
| JPOP_DD893816 | EVQLVESGGGLVQPGGSLRLSCAASGSIFRINTMAWYRQAPGKQRELVATITNGGNTNYA | 60 |
| EPOP_CS585372 | EVQLVESGGGLVQPGGSLRLSCVTSGSIRSINTMGWYRQAPGNERELVATITSGGTTNYA | 60 |
| EPOP_JC984551 | QVQLQASGGGLAQPGGSLRLSVTVSGSIDVINNMAWYRQAPGNARELVATITSGFSTNYA | 60 |
| VHHA12 | | |

*FIG. 9 (CONT.)*

| | | | |
|---|---|---|---|
| EPOP_JA737802 | DSVKGRFTISRDNAKNTVYLQMNSLKPEDTAVYYCNAVVAGTFS------------TYDYWGQGTQVTVSS---- | 119 |
| EPOP_JA737727 | DSVKGRFTISRDNAKNTVYLQMNSLKPEDTAVYYCNAVVAGTFS------------TYDYWGQGTQVTVSS---- | 119 |
| NRPL1_NRP_JA737727 | DSVKGRFTISRDNAKNTVYLQMNSLKPEDTAVYYCNAVVAGTFS------------TYDYWGQGTQVTVSS---- | 119 |
| NRPL2_NRP00429CBB | DSVKGRFTISRDNAKNTVYLQMNSLKPEDTAVYYCNAVVAGTFS------------TYDYWGQGTQVTVSS---- | 119 |
| NRPL2_NRP0042A2EC | DSVKGRFTISRDNAKNTVYLQMNSLKPEDTAVYYCNAVVAGTFS------------TYDYWGQGTQVTVSS---- | 119 |
| NRPL1_NRP_JA737728 | DSVKGRFTISRDNAKNTVYLQMNSLKPEDTAVYYCNAVVAGTFS------------TYDYWGQGTQVTVSS---- | 119 |
| EPOP_JA737803 | DSVKGRFTISRDNAKNTVYLQMNSLKPEDTAVYYCNAVVAGTFS------------TYDYWGQGTQVTVSS---- | 119 |
| EPOP_JA737728 | DSVKGRFTISRDNAKNTVYLQMNSLKPEDTAVYYCNAVVAGTFS------------TYDYWGQGTQVTVSS---- | 119 |
| NRPL2_NRP0042909A | DSVKGRFTISRDNAKNTVYLQMNSLKPEDTAVYYCNAVVAGTFS------------TYDYWGQGTQVTVSS---- | 119 |
| NRPL1_NRP_JA737730 | DSVKGRFTISRDNAKNTVYLQMNSLKPEDTAVYYCNAVVAGTFS------------TYDYWGQGTQVTVSS---- | 119 |
| EPOP_JA737805 | DSVKGRFTISRDNAKNTVYLQMNSLKPEDTAVYYCNAVVAGTFS------------TYDYWGQGTQVTVSS---- | 119 |
| EPOP_JA737730 | DSVKGRFTISRDNAKNTVYLQMNSLKPEDTAVYYCNAVVAGTFS------------TYDYWGQGTQVTVSS---- | 119 |
| NRPL2_NRP00429FF4 | DSVKGRFTISRDNAKNTVYLQMNSLKPEDTAVYYCNAKVAGTFS------------TYDYWGQGTQVTVSS---- | 119 |
| NRPL1_NRP_JA737736 | DSVKGRFTISRDNAKNTVYLQMNSLKPEDTAVYYCNAKVAGTFS------------TYDYWGQGTQVTVSS---- | 119 |
| EPOP_JA737811 | DSVKGRFTISRDNAKNTVYLQMNSLKPEDTAVYYCNAKVAGTFS------------TYDYWGQGTQVTVSS---- | 119 |
| EPOP_JA737736 | DSVKGRFTISRDNAKNTVYLQMNSLKPEDTAVYYCNAKVAGTFS------------IYDYWGQGTQVTVSS---- | 119 |
| NRPL2_NRP00429GA4 | DSVKGRFTISRDNAKNTVYLQMNSLKPEDTAVYYCNAKVAGTFS------------IYDYWGQGTQVTVSS---- | 119 |
| NRPL1_NRP_JA737737 | DSVKGRFTISRDNAKNTVYLQMNSLKPEDTAVYYCNAKVAGTFS------------IYDYWGQGTQVTVSS---- | 119 |
| EPOP_JA737812 | DSVKGRFTISRDNAKNTVYLQMNSLKPEDTAVYYCNAKVAGTFS------------IYDYWGQGTQVTVSS---- | 119 |
| EPOP_JA737737 | DSVKGRFTVSRDNAKNTVYLQMNSLKPEDTAVYYCNAKVAGTFS------------IYDYWGQGTQVTVSS---- | 119 |
| NRPL2_NRP0042A715 | DSVKGRFTISRDNAKNTVYLQMNSLKAEDTAVYYCNAKVAGTFS------------IYDYWGQGTQVTVSS---- | 119 |
| NRPL1_NRP_JA737732 | DSVKGRFTISRDNAKNTVYLQMNSLKAEDTAVYYCNAKVAGTFS------------IYDYWGQGTQVTVSS---- | 119 |
| EPOP_JA737807 | DSVKGRFTISRDNAKNTVYLQMNSLKAEDTAVYYCNAKVAGTFS------------IYDYWGQGTQVTVSS---- | 119 |
| EPOP_JA737732 | DSVKGRFTISRDNAKNTVYLQMNSLKPEDTAVYYCNAKVAGTFS------------IYDYWGQGTQVTVSS---- | 119 |
| NRPL2_NRP0042A07C | DSVKGRFTISRDNAKNTVYLQMNSLKPEDTAVYYCNAKVAGTFS------------IYDYWGQGTQVTVSS---- | 119 |
| NRPL1_NRP_JA737733 | DSVKGRFTISRDNAKNTVYLQMNSLKPEDTAVYYCNAKVAGTFS------------IYDYWGQGTQVTVSS---- | 119 |
| EPOP_JA737808 | DSVKGRFTISRDNAKNTVYLQMNSLKPEDTAVYYCNAKVAGTFS------------IYDYWGQGTQVTVSS---- | 119 |
| EPOP_JA737733 | DSVKGRFTISRDNAKNTVYLQMNSLKPEDTAVYYCNAKVAGTFS------------IYDYWGQGTQVTVSS---- | 119 |
| NRPL1_NRP_JA737731 | DSVKGRFTISRDNAKNTVYLQMNSLKPEDTAVYYCNADGIHYSDYDAPPIREYDYWGQGTQVTVSS---- | 127 |
| NRPL2_NRP003AC89C | DSVKGRFTISRDNAKNTVYLQMNSLKPEDTAVYYCNADGIHYSDYDAPPIREYDYWGQGTQVTVSS---- | 127 |
| NRPL1_NRP_JA381965 | DSVKGRFTISRDNAKNTVYLQMNSLKPEDTAVYYCNADGIHYSDYDAPPIREYDYWGQGTQVTVSS---- | 127 |
| EPOP_JA381965 | DSVKGRFTISRDNAKNTVYLQMNSLKPEDTAVYYCNAN--VKTWAGMTR-------DYWGQGTQVTVSS---- | 120 |
| NRPL2_NRP003AFFF2 | DSVKGRFTISRDNAKNTVYLQMNSLKPEDTAVYYCNAN--VKTWAGMTR-------DYWGQGTQVTVSS---- | 120 |
| NRPL1_NRP_JA381850 | DSVKGRFTISRDNAKNTVYLQMNSLKPEDTAVYYCNAN--VKTWAGMTR-------DYWGQGTQVTVSS---- | 120 |
| EPOP_JA381872 | DSVKGRFTISRDNAKNTVYLQMNSLKPEDTAVYYCNAN--VKTWAGMTR-------DYWGQGTQVTVSS---- | 120 |
| EPOP_JA381850 | DSVKGRFTISRDNAKNTVYLQMNSLKPEDTAVYYCNAAIVTMTSP-----------YSDYWGQGTQVTVSS---- | 120 |
| EPOP_JC104783 | DSVKGRFTISRDNAKNTVYLQMNSLKPEDTAVYYCNAAIVTMTSP-----------YSDYWGQGTQVTVSS---- | 120 |

FIG. 9 (CONT. 1)

| | | |
|---|---|---|
| USPOP_ACE10965 | DSLKGRFTISRDNAKNAVYLQMNNLKPEDTAVYYCNAHITPAGSSN------------YVIGYWGHGTKVTVTVSSEPKTPKPQP | 131 |
| NRPL2_NRP002147C2 | DSLKGRFTISRDNAKNAVYLQMNNLKPEDTAVYYCNAHITPAGSSN------------YVYGYWGHGTKVTVSSEPKTPKPQP | 131 |
| NRPL1_NRP_ACE10965 | DSLKGRFTISRDNAKNAVYLQMNNLKPEDTAVYYCNAHITPAGSSN------------YVIGYWGHGTKVTVSSEPKTPKPQP | 131 |
| NRPL2_NRP0042A6EF | DSVKGRFTISRDNAKNTVYLQMNSLKPEDTAVYYCNVQGTGPSSWLFN---------EYDYWGQGTQVTVSS----------- | 123 |
| NRPL1_NRP_JA737747 | DSVKGRFTISRDNAKNTVYLQMNSLKPEDTAVYYCNVQGTGPSSWLFN---------EYDYWGQGTQVTVSS----------- | 123 |
| EPOP_JA737822 | DSVKGRFTISRDNAKNTVYLQMNSLKPEDTAVYYCNVQGTGPSSWLFN---------EYDYWGQGTQVTVSS----------- | 123 |
| EPOP_JA737747 | DSVKGRFTISRDNAKNTVYLQMNSLKPEDTAVYYCNVQGTGPSSWLFN---------EYDYWGQGTQVTVSS----------- | 123 |
| NRPL2_NRP00310074B | NSVKGRFTISRDNAKNTVYLQMNSLKPEDTAVYYCNVKSHFPPNWGGP---------TPDYWGQGTQVTVSS----------- | 123 |
| NRPL1_NRP_HC481076 | NSVKGRFTISRDNAKNTVYLQMNSLKPEDTAVYYCNVKSHFPPNWGGP---------TPDYWGQGTQVTVSS----------- | 123 |
| EPOP_HC481076 | NSVKGRFTISRDNAKNTVYLQMNSLKPEDTAVYYCNVKSHFPPNWGGP---------TPDYWGQGTQVTVSS----------- | 123 |
| EPOP_JC104795 | DSVKGRFTISRDNAKNTVYLQMNSLKPEDTAVYYCNVLVIGPLEG------------YDYWGQGTQVTVSS------------ | 119 |
| NRPL2_NRP0042A44F | NSVKGRFTISRDNAANTVYLQMNSLKPEDTAVYYCNVKDYGAVLY------------EYDYWGQGTQVTVSS------------ | 120 |
| NRPL1_NRP_JA737723 | NSVKGRFTISRDNAANTVYLQMNSLKPEDTAVYYCNVKDYGAVLY------------EYDYWGQGTQVTVSS------------ | 120 |
| EPOP_JA737798 | NSVKGRFTISRDNAKNTVYLQMNSLKPEDTAVYYCNVKDYGAVLY------------EYDYWGQGTQVTVSS------------ | 120 |
| EPOP_JA737723 | NSVKGRFTISRDNAKNTVYLQMNSLKPEDTAVYYCNVKDYGAVLY------------EYDYWGQGTQVTVSS------------ | 120 |
| NRPL2_NRP002CCF96 | DSVKGRFTISRDNAKNTVYLQMNSLKPEDTAVYYCNAGSTYSPFG------------DKYDYWGQGTQVTVSS----------- | 121 |
| NRPL1_NRP_HC254852 | DSVKGRFTISRDNAKNTVYLQMNSLKPEDTAVYYCNAGSTYSPFG------------DKYDYWGQGTQVTVSS----------- | 121 |
| JPOP_DL500873 | DSVKGRFTISRDNAKNTVYLQMNSLKPEDTAVYYCNAGSTYSPFG------------DKYDYWGQGTQVTVSS----------- | 121 |
| EPOP_HC254852 | DSVKGRFTISRDNAKNTVYLQMNSLKPEDTAVYYCNAGSRFNPFG------------SAYDYWGQGTQVTVSS----------- | 121 |
| NRPL2_NRP002DD9B4 | DSVKGRFTISRDNAKNTVYLQMNSLKPEDTAVYYCNAGSRFNPFG------------SAYDYWGQGTQVTVSS----------- | 121 |
| NRPL1_NRP_HC254854 | DSVKGRFTISRDNAKNTVYLQMNSLKPEDTAVYYCNAGSRFNPFG------------SAYDYWGQGTQVTVSS----------- | 121 |
| JPOP_DL500875 | DSVKGRFTISRDNAKNTVYLQMNSLKPEDTAVYYCNAGSRFNPFG------------SAYDYWGQGTQVTVSS----------- | 121 |
| EPOP_HC254854 | DSVKGRFTISRDNAKNTVYLQMNSLKPEDTAVYYCNAGSRFNPFG------------SAYDYWGQGTQVTVSS----------- | 121 |
| NRPL2_NRP002D7845 | DSVKGRFTISRDNAKNTVYLQMNSLKPEDTAVYYCNHRGAGAH--------------RVDDYWGQGTQVTVSS------------ | 119 |
| NRPL1_NRP_HC252013 | DSVKGRFTISRDNAKNTVYLQMNSLKPEDTAVYYCNHRGAGAH--------------RVDDYWGQGTQVTVSS------------ | 119 |
| JPOP_DJ998044 | DSVKGRFTISRDNAKNTVYLQMNSLKPEDTAVYYCNHRGAGAH--------------RVDDYWGQGTQVTVSS------------ | 119 |
| EPOP_HC252013 | DSVKGRFTISRDNAKNTVYLQMNSLKPEDTAVYYCNADEWGDYPG------------QVYDYWGQGTQVTVSS------------ | 121 |
| EPOP_JC291691 | DSVKGRFTISRDNAKNTVYLQMNSLKPEDTADYYCN---LWHTDFV-----------SFYDYWGQGTQVTVSS----------- | 119 |
| EPOP_JB816376 | DSVKGRFTISRDNAKNTVYLQMNSLKPEDTAVYYCNARQQFIGAP------------YEYWGQGTQVTVSS------------ | 119 |
| EPOP_JC984531 | DSVKGRFTISRDNAKNTVYLQMNSLKPEDTAVYYCKAEIGSTRIRDTY-----YYRDYWGQGIQVTVSS--------------- | 124 |
| NRPL2_NRP000483DA | DSVKGRFTISRDNAKNTVYLQMNSLKPEDTAVYYCKAEIGSTRIRDTY-----YYRDYWGQGIQVTVSS--------------- | 124 |
| NRPL1_NRP_CS585372 | DSVKGRFTISRDNAKNTVYLQMNSLKPEDTAVYYCKAEIGSTRIRDTY-----YYRDYWGQGIQVTVSS--------------- | 124 |
| JPOP_DD893816 | DSVKGRFTISRDNAKNTVYLQMNSLKPEDTAVYYCKAEIGSTRIRDTY-----YYRDYWGQGIQVTVSS--------------- | 124 |
| EPOP_CS585372 | DSVKGRFTISRDNAKNTVYLQMNSLKPEDTAVYYCNLHQRAWARS-----------YVYWGQGTQVTVSS------------ | 119 |
| EPOP_JC984551 | DSVKNRFTISRDNAKKAVYLQMNSLKPEDTADYYSKVHLIRLGAAR------AYDYWGQGTQVTVSS---------- | 120 |
| VHHAl2 | :.*.*.:****.::.:*..:.****.*..* :..... : :..:.:**:. | |

*FIG. 9 (CONT. 2)*

SEQUENCE LISTING

```
<160> NUMBER OF SEQ ID NOS: 49

<210> SEQ ID NO 1
<211> LENGTH: 29
<212> TYPE: PRT
<213> ORGANISM: Artificial Sequence
<220> FEATURE:
<223> OTHER INFORMATION: Synthetic sequence

<400> SEQUENCE: 1

Tyr Thr Ile Trp Met Pro Glu Asn Pro Arg Leu Gly Met Ser Cys Asp
1               5                   10                  15

Ile Phe Thr Asn Ser Arg Gly Lys Arg Ala Ser Lys Gly
```

```
                    20                  25
```

<210> SEQ ID NO 2
<211> LENGTH: 87
<212> TYPE: DNA
<213> ORGANISM: Artificial Sequence
<220> FEATURE:
<223> OTHER INFORMATION: Synthetic sequence

<400> SEQUENCE: 2

```
tatacgattt ggatgccgga aaatccacgt ctgggcatgt cgtgcgatat ctttaccaac    60
agtcgcggta aacgcgcgag caaaggg                                        87
```

<210> SEQ ID NO 3
<211> LENGTH: 120
<212> TYPE: PRT
<213> ORGANISM: Artificial Sequence
<220> FEATURE:
<223> OTHER INFORMATION: Synthetic sequence

<400> SEQUENCE: 3

```
Glu Val Gln Leu Gln Ala Ser Gly Gly Gly Leu Ala Gln Pro Gly Gly
1               5                   10                  15

Ser Leu Arg Leu Ser Val Thr Val Ser Gly Ser Ile Asp Val Ile Asn
            20                  25                  30

Asn Met Ala Trp Tyr Arg Gln Ala Pro Gly Asn Ala Arg Glu Leu Val
        35                  40                  45

Ala Thr Ile Thr Ser Gly Phe Ser Thr Asn Tyr Ala Ser Ser Val Lys
    50                  55                  60

Gly Arg Phe Thr Ile Ser Arg Asp Asn Ala Lys Lys Ala Val Tyr Leu
65                  70                  75                  80

Gln Met Asn Ser Leu Lys Pro Glu Asp Thr Ala Asp Tyr Tyr Ser Lys
                85                  90                  95

Val His Leu Ile Arg Leu Gly Ala Ala Arg Ala Tyr Asp Tyr Trp Gly
            100                 105                 110

Gln Gly Thr Gln Val Thr Val Ser
        115                 120
```

<210> SEQ ID NO 4
<211> LENGTH: 360
<212> TYPE: DNA
<213> ORGANISM: Artificial Sequence
<220> FEATURE:
<223> OTHER INFORMATION: Synthetic sequence

<400> SEQUENCE: 4

```
gaggtgcagc tgcaggcgtc tgggggaggc ttggcgcagc ctgggggtc cctgagactc     60 tccgtaacag tctctggaag tatcgatgtt attaataaca tggcctggta ccgccaggct   120
ccagggaatg cgcgcgagtt ggtcgccaca attactagtg gttttagcac aaactatgca   180
agctccgtga agggccgatt caccatctcc agagacaacg ccaagaaagc ggtatatcta   240
cagatgaaca gcctgaaacc tgaggacacg gccgattatt actctaaggt tcacttaata   300
cgtcttgggg ccgcgcgggc gtatgactac tggggccagg gacccaggt caccgtctcc   360
```

<210> SEQ ID NO 5
<211> LENGTH: 16
<212> TYPE: PRT
<213> ORGANISM: Artificial Sequence
<220> FEATURE:
<223> OTHER INFORMATION: Synthetic sequence

<400> SEQUENCE: 5

Gly Gly Gly Ser Ala Trp Ser His Pro Gln Phe Glu Lys Ala Ala Ala
1               5                   10                  15

<210> SEQ ID NO 6
<211> LENGTH: 48
<212> TYPE: DNA
<213> ORGANISM: Artificial Sequence
<220> FEATURE:
<223> OTHER INFORMATION: Synthetic sequence

<400> SEQUENCE: 6
ggtggaggct cagcttggag ccacccgcag ttcgaaaaag cggccgca            48

<210> SEQ ID NO 7
<211> LENGTH: 42
<212> TYPE: PRT
<213> ORGANISM: Artificial Sequence
<220> FEATURE:
<223> OTHER INFORMATION: Synthetic sequence

<400> SEQUENCE: 7

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30

Trp Glu Val His Gly Gln Gln Thr Arg Leu
        35                  40

<210> SEQ ID NO 8
<211> LENGTH: 126
<212> TYPE: DNA
<213> ORGANISM: Artificial Sequence
<220> FEATURE:
<223> OTHER INFORMATION: Synthetic sequence

<400> SEQUENCE: 8
cgccgggtaa accgcagtga accgacccag cacaatctgc gtgggactgg tcgtgaggtg      60
tccgttacgc cacagtctgg caaaatcatt agctcgtggg aagtacatgg ccagcaaacc     120
cgctta                                                                126

<210> SEQ ID NO 9
<211> LENGTH: 38
<212> TYPE: PRT
<213> ORGANISM: Artificial Sequence
<220> FEATURE:
<223> OTHER INFORMATION: Synthetic sequence

<400> SEQUENCE: 9

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30

Trp Glu Val His Gly Gln
        35

<210> SEQ ID NO 10
<211> LENGTH: 114
<212> TYPE: DNA
<213> ORGANISM: Artificial Sequence
<220> FEATURE:
<223> OTHER INFORMATION: Synthetic sequence

<400> SEQUENCE: 10
cgccgggtaa accgcagtga accgacccag cacaatctgc gtgggactgg tcgtgaggtg    60
tccgttacgc cacagtctgg caaaatcatt agctcgtggg aagtacatgg ccag         114

<210> SEQ ID NO 11
<211> LENGTH: 209
<212> TYPE: PRT
<213> ORGANISM: Artificial Sequence
<220> FEATURE:
<223> OTHER INFORMATION: Synthetic sequence

<400> SEQUENCE: 11

Met Ala Tyr Thr Ile Trp Met Pro Glu Asn Pro Arg Leu Gly Met Ser
1               5                   10                  15

Cys Asp Ile Phe Thr Asn Ser Arg Gly Lys Arg Ala Ser Lys Gly Glu
            20                  25                  30

Val Gln Leu Gln Ala Ser Gly Gly Leu Ala Gln Pro Gly Gly Ser
        35                  40                  45

Leu Arg Leu Ser Val Thr Val Ser Gly Ser Ile Asp Val Ile Asn Asn
    50                  55                  60

Met Ala Trp Tyr Arg Gln Ala Pro Gly Asn Ala Arg Glu Leu Val Ala
65                  70                  75                  80

Thr Ile Thr Ser Gly Phe Ser Thr Asn Tyr Ala Ser Ser Val Lys Gly
                85                  90                  95

Arg Phe Thr Ile Ser Arg Asp Asn Ala Lys Lys Ala Val Tyr Leu Gln
            100                 105                 110

Met Asn Ser Leu Lys Pro Glu Asp Thr Ala Asp Tyr Tyr Ser Lys Val
        115                 120                 125

His Leu Ile Arg Leu Gly Ala Ala Arg Ala Tyr Asp Tyr Trp Gly Gln
    130                 135                 140

Gly Thr Gln Val Thr Val Ser Gly Gly Gly Ser Ala Trp Ser His Pro
145                 150                 155                 160

Gln Phe Glu Lys Ala Ala Ala Arg Arg Val Asn Arg Ser Glu Pro Thr
                165                 170                 175

Gln His Asn Leu Arg Gly Thr Gly Arg Glu Val Ser Val Thr Pro Gln
            180                 185                 190

Ser Gly Lys Ile Ile Ser Ser Trp Glu Val His Gly Gln Gln Thr Arg
        195                 200                 205

Leu

<210> SEQ ID NO 12
<211> LENGTH: 633
<212> TYPE: DNA
<213> ORGANISM: Artificial Sequence
<220> FEATURE:
<223> OTHER INFORMATION: Synthetic sequence

<400> SEQUENCE: 12
atggcctata cgatttggat gccggaaaat ccacgtctgg gcatgtcgtg cgatatcttt    60
accaacagtc gcggtaaacg cgcgagcaaa ggggaggtgc agctgcaggc gtctggggga   120
ggcttggcgc agcctggggg gtccctgaga ctctccgtaa cagtctctgg aagtatcgat   180
gttattaata acatggcctg gtaccgccag gctccaggga atgcgcgcga gttggtcgcc   240
acaattacta gtggttttag cacaaactat gcaagctccg tgaagggccg attcaccatc   300
tccagagaca acgccaagaa agcggtatat ctacagatga acagcctgaa acctgaggac   360

```
acggccgatt attactctaa ggttcactta atacgtcttg gggccgcgcg ggcgtatgac      420
tactggggcc aggggaccca ggtcaccgtc tccggtggag gctcagcttg gagccacccg      480
cagttcgaaa aagcggccgc acgccgggta aaccgcagtg aaccgaccca gcacaatctg      540
cgtgggactg gtcgtgaggt gtccgttacg ccacagtctg gcaaaatcat tagctcgtgg      600
gaagtacatg gccagcaaac ccgcttatga taa                                  633
```

```
<210> SEQ ID NO 13
<211> LENGTH: 180
<212> TYPE: PRT
<213> ORGANISM: Artificial Sequence
<220> FEATURE:
<223> OTHER INFORMATION: Synthetic sequence

<400> SEQUENCE: 13
```

Met Ala Glu Val Gln Leu Gln Ala Ser Gly Gly Leu Ala Gln Pro
1               5                   10                  15

Gly Gly Ser Leu Arg Leu Ser Val Thr Val Ser Gly Ser Ile Asp Val
            20                  25                  30

Ile Asn Asn Met Ala Trp Tyr Arg Gln Ala Pro Gly Asn Ala Arg Glu
        35                  40                  45

Leu Val Ala Thr Ile Thr Ser Gly Phe Ser Thr Asn Tyr Ala Ser Ser
    50                  55                  60

Val Lys Gly Arg Phe Thr Ile Ser Arg Asp Asn Ala Lys Lys Ala Val
65                  70                  75                  80

Tyr Leu Gln Met Asn Ser Leu Lys Pro Glu Asp Thr Ala Asp Tyr Tyr
                85                  90                  95

Ser Lys Val His Leu Ile Arg Leu Gly Ala Ala Arg Ala Tyr Asp Tyr
            100                 105                 110

Trp Gly Gln Gly Thr Gln Val Thr Val Ser Gly Gly Ser Ala Trp
        115                 120                 125

Ser His Pro Gln Phe Glu Lys Ala Ala Ala Arg Val Asn Arg Ser
    130                 135                 140

Glu Pro Thr Gln His Asn Leu Arg Gly Thr Gly Arg Glu Val Ser Val
145                 150                 155                 160

Thr Pro Gln Ser Gly Lys Ile Ile Ser Ser Trp Glu Val His Gly Gln
                165                 170                 175

Gln Thr Arg Leu
            180

```
<210> SEQ ID NO 14
<211> LENGTH: 546
<212> TYPE: DNA
<213> ORGANISM: Artificial Sequence
<220> FEATURE:
<223> OTHER INFORMATION: Synthetic sequence

<400> SEQUENCE: 14
atggccgagg tgcagctgca ggcgtctggg ggaggcttgg cgcagcctgg ggggtccctg       60
agactctccg taacagtctc tggaagtatc gatgttatta ataacatggc ctggtaccgc      120
caggctccag ggaatgcgcg cgagttggtc gccacaatta ctagtggttt tagcacaaac      180
tatgcaagct ccgtgaaggg ccgattcacc atctccagag acaacgccaa gaaagcggta      240
tatctacaga tgaacagcct gaaacctgag gacacggccg attattactc taaggttcac      300
ttaatacgtc ttggggccgc gcgggcgtat gactactggg gccaggggac ccaggtcacc      360
```

```
gtctccggtg gaggctcagc ttggagccac ccgcagttcg aaaaagcggc cgcacgccgg    420
gtaaaccgca gtgaaccgac ccagcacaat ctgcgtggga ctggtcgtga ggtgtccgtt    480
acgccacagt ctggcaaaat cattagctcg tgggaagtac atggccagca aacccgctta    540
tgataa                                                               546
```

<210> SEQ ID NO 15
<211> LENGTH: 205
<212> TYPE: PRT
<213> ORGANISM: Artificial Sequence
<220> FEATURE:
<223> OTHER INFORMATION: Synthetic sequence

<400> SEQUENCE: 15

```
Met Ala Tyr Thr Ile Trp Met Pro Glu Asn Pro Arg Leu Gly Met Ser
1               5                   10                  15

Cys Asp Ile Phe Thr Asn Ser Arg Gly Lys Arg Ala Ser Lys Gly Glu
            20                  25                  30

Val Gln Leu Gln Ala Ser Gly Gly Leu Ala Gln Pro Gly Gly Ser
        35                  40                  45

Leu Arg Leu Ser Val Thr Val Ser Gly Ser Ile Asp Val Ile Asn Asn
    50                  55                  60

Met Ala Trp Tyr Arg Gln Ala Pro Gly Asn Ala Arg Glu Leu Val Ala
65                  70                  75                  80

Thr Ile Thr Ser Gly Phe Ser Thr Asn Tyr Ala Ser Ser Val Lys Gly
                85                  90                  95

Arg Phe Thr Ile Ser Arg Asp Asn Ala Lys Lys Ala Val Tyr Leu Gln
            100                 105                 110

Met Asn Ser Leu Lys Pro Glu Asp Thr Ala Asp Tyr Tyr Ser Lys Val
        115                 120                 125

His Leu Ile Arg Leu Gly Ala Ala Arg Ala Tyr Asp Tyr Trp Gly Gln
    130                 135                 140

Gly Thr Gln Val Thr Val Ser Gly Gly Gly Ser Ala Trp Ser His Pro
145                 150                 155                 160

Gln Phe Glu Lys Ala Ala Ala Arg Arg Val Asn Arg Ser Glu Pro Thr
                165                 170                 175

Gln His Asn Leu Arg Gly Thr Gly Arg Glu Val Ser Val Thr Pro Gln
            180                 185                 190

Ser Gly Lys Ile Ile Ser Ser Trp Glu Val His Gly Gln
        195                 200                 205
```

<210> SEQ ID NO 16
<211> LENGTH: 621
<212> TYPE: DNA
<213> ORGANISM: Artificial Sequence
<220> FEATURE:
<223> OTHER INFORMATION: Synthetic sequence

<400> SEQUENCE: 16

```
atggcctata cgatttggat gccggaaaat ccacgtctgg gcatgtcgtg cgatatcttt     60
accaacagtc gcggtaaacg cgcgagcaaa ggggaggtgc agctgcaggc gtctggggga    120
ggcttggcgc agcctggggg gtccctgaga ctctccgtaa cagtctctgg aagtatcgat    180
gttattaata acatggcctg gtaccgccag gctccaggga atgcgcgcga gttggtcgcc    240
acaattacta gtggttttag cacaaactat gcaagctccg tgaagggccg attcaccatc    300
tccagagaca cgccaagaa agcggtatat ctacagatga cagcctgaa acctgaggac    360
```

```
acggccgatt attactctaa ggttcactta atacgtcttg gggccgcgcg ggcgtatgac     420
tactggggcc aggggaccca ggtcaccgtc tccggtggag gctcagcttg gagccacccg     480
cagttcgaaa agcggccgc acgccgggta aaccgcagtg aaccgaccca gcacaatctg     540
cgtgggactg tcgtgaggt gtccgttacg ccacagtctg gcaaaatcat tagctcgtgg     600
gaagtacatg gccagtgata a                                              621
```

<210> SEQ ID NO 17
<211> LENGTH: 31
<212> TYPE: PRT
<213> ORGANISM: Artificial Sequence
<220> FEATURE:
<223> OTHER INFORMATION: Synthetic sequence

<400> SEQUENCE: 17

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: Synthetic sequence

<400> SEQUENCE: 18

Arg Arg Val Asn Arg Ser Glu Pro Thr Gln Leu Asn Leu Arg Gly Thr
1               5                   10                  15

Gly Arg Glu Val Ser Val Thr Pro Gln Ser Gly Lys Ile Ile Ser
            20                  25                  30

<210> SEQ ID NO 19
<211> LENGTH: 13
<212> TYPE: PRT
<213> ORGANISM: Artificial Sequence
<220> FEATURE:
<223> OTHER INFORMATION: Synthetic sequence

<400> SEQUENCE: 19

Ser Trp Glu Ser His Lys Ser Gly Gly Gln Thr Arg Leu
1               5                   10

<210> SEQ ID NO 20
<211> LENGTH: 44
<212> TYPE: PRT
<213> ORGANISM: Artificial Sequence
<220> FEATURE:
<223> OTHER INFORMATION: Synthetic sequence

<400> SEQUENCE: 20

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30

Trp Glu Ser His Lys Ser Gly Gly Gln Thr Arg Leu
        35                  40

<210> SEQ ID NO 21
<211> LENGTH: 11
<212> TYPE: PRT
<213> ORGANISM: Artificial Sequence

```
<220> FEATURE:
<223> OTHER INFORMATION: Synthetic sequence
<220> FEATURE:
<221> NAME/KEY: misc_feature
<222> LOCATION: (3)..(7)
<223> OTHER INFORMATION: Xaa can be any naturally occurring amino acid

<400> SEQUENCE: 21

Ser Trp Xaa Xaa Xaa Xaa Xaa Gln Thr Arg Leu
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(8)
<223> OTHER INFORMATION: Xaa can be any naturally occurring amino acid

<400> SEQUENCE: 22

Ser Trp Xaa Xaa Xaa Xaa Xaa Xaa Gln Thr Arg Leu
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(9)
<223> OTHER INFORMATION: Xaa can be any naturally occurring amino acid

<400> SEQUENCE: 23

Ser Trp Xaa Xaa Xaa Xaa Xaa Xaa Xaa Gln Thr Arg Leu
1               5                   10

<210> SEQ ID NO 24
<211> LENGTH: 42
<212> TYPE: PRT
<213> ORGANISM: Artificial Sequence
<220> FEATURE:
<223> OTHER INFORMATION: Synthetic sequence

<400> SEQUENCE: 24

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30

Trp Glu Val His Gly Gly Gln Thr Arg Leu
        35                  40

<210> SEQ ID NO 25
<211> LENGTH: 42
<212> TYPE: PRT
<213> ORGANISM: Artificial Sequence
<220> FEATURE:
<223> OTHER INFORMATION: Synthetic sequence

<400> SEQUENCE: 25

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
```

```
                    20                  25                  30

Trp Glu Val Ala Thr Gln Gln Thr Arg Leu
        35                  40

<210> SEQ ID NO 26
<211> LENGTH: 42
<212> TYPE: PRT
<213> ORGANISM: Artificial Sequence
<220> FEATURE:
<223> OTHER INFORMATION: Synthetic sequence

<400> SEQUENCE: 26

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30

Trp Glu Val Tyr Thr Gly Gln Thr Arg Leu
        35                  40

<210> SEQ ID NO 27
<211> LENGTH: 42
<212> TYPE: PRT
<213> ORGANISM: Artificial Sequence
<220> FEATURE:
<223> OTHER INFORMATION: Synthetic sequence

<400> SEQUENCE: 27

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30

Trp Glu Val His Thr Gly Gln Thr Arg Leu
        35                  40

<210> SEQ ID NO 28
<211> LENGTH: 42
<212> TYPE: PRT
<213> ORGANISM: Artificial Sequence
<220> FEATURE:
<223> OTHER INFORMATION: Synthetic sequence

<400> SEQUENCE: 28

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30

Trp Glu Val His Thr Gln Gln Thr Arg Leu
        35                  40

<210> SEQ ID NO 29
<211> LENGTH: 42
<212> TYPE: PRT
<213> ORGANISM: Artificial Sequence
<220> FEATURE:
<223> OTHER INFORMATION: Synthetic sequence

<400> SEQUENCE: 29

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30

Trp Glu Val Ala Gly Gly Gln Thr Arg Leu
```

<210> SEQ ID NO 30
<211> LENGTH: 44
<212> TYPE: PRT
<213> ORGANISM: Artificial Sequence
<220> FEATURE:
<223> OTHER INFORMATION: Synthetic sequence

<400> SEQUENCE: 30

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30

Trp Ala Glu Ala Gln His Thr Gln Gln Thr Arg Leu
        35                  40

<210> SEQ ID NO 31
<211> LENGTH: 44
<212> TYPE: PRT
<213> ORGANISM: Artificial Sequence
<220> FEATURE:
<223> OTHER INFORMATION: Synthetic sequence

<400> SEQUENCE: 31

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30

Trp Glu Val His Ala Ser Gly Gly Gln Thr Arg Leu
        35                  40

<210> SEQ ID NO 32
<211> LENGTH: 30
<212> TYPE: PRT
<213> ORGANISM: Artificial Sequence
<220> FEATURE:
<223> OTHER INFORMATION: Synthetic sequence

<400> SEQUENCE: 32

Lys Ser Val Arg Thr Trp Asn Glu Ile Leu Pro Ser Lys Gly Cys Leu
1               5                   10                  15

Arg Val Gly Gly Arg Cys His Pro His Val Asn Gly Gly Gly
            20                  25                  30

<210> SEQ ID NO 33
<211> LENGTH: 25
<212> TYPE: PRT
<213> ORGANISM: Artificial Sequence
<220> FEATURE:
<223> OTHER INFORMATION: Synthetic sequence

<400> SEQUENCE: 33

Lys Ser Val Arg Thr Trp Asn Glu Ile Ile Pro Ser Lys Gly Cys Leu
1               5                   10                  15

Arg Val Gly Gly Arg Cys His Pro His
            20                  25

<210> SEQ ID NO 34
<211> LENGTH: 29
<212> TYPE: PRT
<213> ORGANISM: Artificial Sequence
<220> FEATURE:
<223> OTHER INFORMATION: Synthetic sequence

<400> SEQUENCE: 34

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25

<210> SEQ ID NO 35
<211> LENGTH: 24
<212> TYPE: PRT
<213> ORGANISM: Artificial Sequence
<220> FEATURE:
<223> OTHER INFORMATION: Synthetic sequence

<400> SEQUENCE: 35

Gly Gly Thr Ala Thr Ala Gly Thr Cys Ala Ala Thr Thr Cys Thr Thr
1               5                   10                  15

Ala Thr Thr Thr Gly Ala Ala Thr
            20

<210> SEQ ID NO 36
<211> LENGTH: 24
<212> TYPE: PRT
<213> ORGANISM: Artificial Sequence
<220> FEATURE:
<223> OTHER INFORMATION: Synthetic sequence

<400> SEQUENCE: 36

Cys Thr Thr Gly Ala Ala Thr Cys Thr Cys Ala Ala Thr Ala Gly Gly
1               5                   10                  15

Thr Gly Cys Cys Cys Thr Thr Ala
            20

<210> SEQ ID NO 37
<211> LENGTH: 23
<212> TYPE: PRT
<213> ORGANISM: Artificial Sequence
<220> FEATURE:
<223> OTHER INFORMATION: Synthetic sequence

<400> SEQUENCE: 37

Thr Thr Ala Ala Cys Ala Cys Thr Thr Cys Ala Thr Gly Gly Cys Cys
1               5                   10                  15

Thr Gly Thr Ala Ala Gly Ala
            20

<210> SEQ ID NO 38
<211> LENGTH: 24
<212> TYPE: PRT
<213> ORGANISM: Artificial Sequence
<220> FEATURE:
<223> OTHER INFORMATION: Synthetic sequence

<400> SEQUENCE: 38

Thr Gly Thr Gly Cys Cys Ala Thr Gly Cys Thr Cys Cys Ala Gly
1               5                   10                  15

Thr Ala Thr Thr Cys Thr Thr Gly
            20

<210> SEQ ID NO 39
<211> LENGTH: 24
<212> TYPE: PRT
<213> ORGANISM: Artificial Sequence
<220> FEATURE:

<223> OTHER INFORMATION: Synthetic sequence

<400> SEQUENCE: 39

Cys Thr Gly Cys Thr Thr Cys Thr Thr Ala Ala Cys Cys Cys Cys Ala
1               5                   10                  15

Gly Thr Ala Ala Gly Cys Cys Ala
            20

<210> SEQ ID NO 40
<211> LENGTH: 24
<212> TYPE: PRT
<213> ORGANISM: Artificial Sequence
<220> FEATURE:
<223> OTHER INFORMATION: Synthetic sequence

<400> SEQUENCE: 40

Cys Ala Gly Cys Ala Gly Thr Gly Cys Cys Thr Gly Ala Ala Gly
1               5                   10                  15

Ala Thr Thr Ala Gly Cys Ala Gly
            20

<210> SEQ ID NO 41
<211> LENGTH: 24
<212> TYPE: PRT
<213> ORGANISM: Artificial Sequence
<220> FEATURE:
<223> OTHER INFORMATION: Synthetic sequence

<400> SEQUENCE: 41

Cys Cys Cys Cys Ala Gly Gly Cys Gly Ala Thr Gly Gly Ala Cys Ala
1               5                   10                  15

Ala Thr Thr Ala Thr Gly Ala Thr
            20

<210> SEQ ID NO 42
<211> LENGTH: 24
<212> TYPE: PRT
<213> ORGANISM: Artificial Sequence
<220> FEATURE:
<223> OTHER INFORMATION: Synthetic sequence

<400> SEQUENCE: 42

Cys Ala Cys Thr Thr Gly Gly Thr Thr Thr Thr Ala Thr Thr Gly Cys
1               5                   10                  15

Ala Cys Ala Gly Ala Ala Gly Cys
            20

<210> SEQ ID NO 43
<211> LENGTH: 24
<212> TYPE: PRT
<213> ORGANISM: Artificial Sequence
<220> FEATURE:
<223> OTHER INFORMATION: Synthetic sequence

<400> SEQUENCE: 43

Thr Cys Cys Thr Gly Cys Thr Gly Thr Gly Thr Cys Cys Thr Gly Ala
1               5                   10                  15

Gly Gly Thr Gly Cys Ala Thr Thr
            20

<210> SEQ ID NO 44
<211> LENGTH: 24
<212> TYPE: PRT
<213> ORGANISM: Artificial Sequence

```
<220> FEATURE:
<223> OTHER INFORMATION: Synthetic sequence

<400> SEQUENCE: 44

Gly Cys Cys Cys Ala Gly Ala Thr Cys Cys Ala Gly Cys Ala Thr Gly
1               5                   10                  15
Cys Ala Ala Gly Gly Thr Gly Cys
            20

<210> SEQ ID NO 45
<211> LENGTH: 193
<212> TYPE: PRT
<213> ORGANISM: Artificial Sequence
<220> FEATURE:
<223> OTHER INFORMATION: Synthetic sequences

<400> SEQUENCE: 45

Met Ala Tyr Thr Ile Trp Met Pro Glu Asn Pro Arg Leu Gly Met Ser
1               5                   10                  15

Cys Asp Ile Phe Thr Asn Ser Arg Gly Lys Arg Ala Ser Lys Gly Glu
            20                  25                  30

Val Gln Leu Gln Ala Ser Gly Gly Leu Ala Gln Pro Gly Gly Ser
        35                  40                  45

Leu Arg Leu Ser Val Thr Val Ser Gly Ser Ile Asp Val Ile Asn Asn
    50                  55                  60

Met Ala Trp Tyr Arg Gln Ala Pro Gly Asn Ala Arg Glu Leu Val Ala
65                  70                  75                  80

Thr Ile Thr Ser Gly Phe Ser Thr Asn Tyr Ala Ser Ser Val Lys Gly
                85                  90                  95

Arg Phe Thr Ile Ser Arg Asp Asn Ala Lys Lys Ala Val Tyr Leu Gln
            100                 105                 110

Met Asn Ser Leu Lys Pro Glu Asp Thr Ala Asp Tyr Tyr Ser Lys Val
        115                 120                 125

His Leu Ile Arg Leu Gly Ala Ala Arg Ala Tyr Asp Tyr Trp Gly Gln
    130                 135                 140

Gly Thr Gln Val Thr Val Ser Arg Arg Val Asn Arg Ser Glu Pro Thr
145                 150                 155                 160

Gln His Asn Leu Arg Gly Thr Gly Arg Glu Val Ser Val Thr Pro Gln
                165                 170                 175

Ser Gly Lys Ile Ile Ser Ser Trp Glu Val His Gly Gln Gln Thr Arg
            180                 185                 190

Leu

<210> SEQ ID NO 46
<211> LENGTH: 585
<212> TYPE: DNA
<213> ORGANISM: Artificial Sequence
<220> FEATURE:
<223> OTHER INFORMATION: Synthetic sequences

<400> SEQUENCE: 46
atggcctata cgatttggat gccggaaaat ccacgtctgg gcatgtcgtg cgatatcttt     60
accaacagtc gcggtaaacg cgcgagcaaa ggggaggtgc agctgcaggc gtctggggga    120
ggcttggcgc agcctggggg gtccctgaga ctctccgtaa cagtctctgg aagtatcgat    180
gttattaata acatggcctg gtaccgccag gctccaggga atgcgcgcga gttggtcgcc    240
acaattacta gtggttttag cacaaactat gcaagctccg tgaagggccg attcaccatc    300
```

-continued

```
tccagagaca acgccaagaa agcggtatat ctacagatga acagcctgaa acctgaggac    360
acggccgatt attactctaa ggttcactta atacgtcttg gggccgcgcg ggcgtatgac    420
tactggggcc aggggaccca ggtcaccgtc tcccgccggg taaaccgcag tgaaccgacc    480
cagcacaatc tgcgtgggac tggtcgtgag gtgtccgtta cgccacagtc tggcaaaatc    540
attagctcgt gggaagtaca tggccagcaa acccgcttat gataa                   585

<210> SEQ ID NO 47
<211> LENGTH: 8
<212> TYPE: PRT
<213> ORGANISM: Artificial Sequence
<220> FEATURE:
<223> OTHER INFORMATION: Synthetic sequence

<400> SEQUENCE: 47

Ile Asp Val Ile Asn Asn Met Ala
1               5

<210> SEQ ID NO 48
<211> LENGTH: 10
<212> TYPE: PRT
<213> ORGANISM: Artificial Sequence
<220> FEATURE:
<223> OTHER INFORMATION: Synthetic sequence

<400> SEQUENCE: 48

Thr Ile Thr Ser Gly Phe Ser Thr Asn Tyr
1               5                   10

<210> SEQ ID NO 49
<211> LENGTH: 15
<212> TYPE: PRT
<213> ORGANISM: Artificial Sequence
<220> FEATURE:
<223> OTHER INFORMATION: Synthetic sequence

<400> SEQUENCE: 49

Lys Val His Leu Ile Arg Leu Gly Ala Ala Arg Ala Tyr Asp Tyr
1               5                   10                  15
```

IN VITRO BLOOD-BRAIN BARRIER MODEL

The invention is in the domain of delivery of molecules to brain cells across the blood-brain barrier. The invention relates to a novel polypeptide-based carrier that allows the efficient delivery of an effector peptide, to neuron cells across the blood-brain barrier, and to methods for the production and testing of such carrier, including a model for testing the capacity of such molecule to cross the blood-brain barrier and/or the toxicity of molecules on the blood brain barrier and/or the capacity of molecules that have crossed to target human brain cells (e/g. neurons, astrocytes and microglial cells).

BACKGROUND OF THE INVENTION

In the context of treatment development for diseases such as neurodegenerative diseases and brain trauma, drug access and availability to the brain are still unmet needs. Indeed, the brain is isolated from the systemic blood flow by a structure called the blood-brain barrier (BBB). The BBB is mostly composed of cerebral endothelial cells that dynamically interact with the neighbouring cells: astrocytes, pericytes, perivascular microglia and neurons. The three major functions of the BBB are the creation and maintenance of ionic homeostasis for neuronal functions, supply of the central nervous system (CNS) with nutrients, and protection from toxic injuries or some infectious agents. The delivery of therapeutic substances to the brain has to overcome the BBB, and turn it into an entry gate. Despite efforts to overcome the junctional or efflux barriers or to circumvent the BBB, most of the newly developed neuropharmaceuticals fail due to poor CNS pharmokinetics.

In the context of delivering molecules across the blood brain barrier (BBB), a type of highly soluble carriers derived from camelid heavy chain-only antibodies (HcAbs) was described. The variable heavy chain domains (VHH) of these antibodies show antigen specificity and affinity similar to conventional antibody constructs consisting of light and heavy chain heterodimers, and display a smaller size of roughly 15 kDa. A VHH is also designated "VHH fragment" to reflect that it is a portion of an antibody. VHH were shown, in specific contexts, to cross the BBB. Although for the time being no specific structural characteristic of VHH were determined to convey permeability across the BBB, an important parameter seems to be the isoelectric point (pI): permeable VHH are thought to usually be basic (especially with a pI higher than 8.5). In addition, size is considered an important factor of VHH permeability and transport capacity and in particular its low molecular weight monomeric structure is considered to contribute to these capacities. It was contemplated that targeting specific cell-surface antigens might induce endocytosis and improve the permeability of such VHH across the BBB. It was also contemplated to use a VHH specific for a brain antigen as a vehicle to target a cargo molecule to a specific site in the brain, across the BBB (Li et al., 2012, WO 2010/004432 A1, U.S. Pat. No. 8,460, 888 B2). Such vehicle-cargo constructs, however, may have reduced efficiency or reduced application scope, in particular due to their binding to the brain antigen, which might result in sequestration of a majority of the cargo molecule away from its site of action.

BRIEF SUMMARY OF THE INVENTION

The inventors have surprisingly identified a basic VHH, which does not recognize any brain-specific antigen and is useful as a vehicle to transport a peptide (so-called cargo peptide) across the blood-brain barrier. The cargo molecule, typically a peptide with specific activity on a brain component, having crossed the BBB, may retain its biological activity and have access to the site of its activity.

The invention therefore provides a novel polypeptide comprising or consisting in a VHH of a camelid heavy-chain antibody, said VHH having the sequence of SEQ ID NO:3. The invention further provides a polypeptide comprising or consisting of a VHH having a sequence variant of SEQ ID NO:3, such variant being as described below. The invention further provides a polypeptide comprising or consisting of a VHH having a portion of the sequence of SEQ ID NO:3 or of a sequence variant thereof, as described below. The VHH and/or polypeptide comprising a VHH of the invention is permeable across the BBB and does not recognize any brain antigen, in particular any human brain antigen, and/or does not specifically bind to any human brain protein. In particular embodiments, the VHH and/or polypeptide comprising a VHH of the invention has a basic pI.

The invention also provides, as described below, VHH-comprising polypeptides consisting of chimeric (or fusion) polypeptides, comprising or consisting in a VHH as defined herein with additional fused peptides/polypeptides, including peptides targeting neuron cells, peptides used as tags and/or spacers and/or effector peptides having an intended and advantageous biological effect on brain cells.

Also provided are polynucleotides coding for such VHH or VHH-comprising polypeptides, vectors comprising said polynucleotides, cells containing such vectors, polynucleotides, VHH or VHH-comprising polypeptides and pharmaceutical compositions comprising such cells, vectors, polynucleotides, VHH or VHH-comprising polypeptide. Also provided are methods for the production of such VHH or VHH-comprising polypeptides or polynucleotides, including methods and devices for testing whether a polypeptide or any other molecule is permeable across the BBB. Also provided are uses of the VHH or polypeptides of the invention, including therapeutic uses.

In particular, the inventors have discovered that targeting of such a VHH or VHH-comprising polypeptide may be improved through a neuron cell-targeting peptide, e.g. fused with the VHH sequence, preferably at the N-terminal extremity. Such peptides are preferably derived from the sequence of a Rabies Virus G protein (RVG), especially one of the novel Rabies Derived Peptides (RDP) disclosed herein. Such peptides are permeable across the BBB by themselves, and their use has been contemplated to transport cargo molecules across the BBB (Fu et al., 2012). However, unlike the VHH or VHH-comprising polypeptide of the invention, they have not been shown to allow the stabilization (increase the half-life) of effector peptides such as the neurovita peptides described herein. In particular embodiments, therefore, the VHH is fused to a neuron-cell targeting peptide, in particular an RDP, preferably with the sequence of (SEQ ID NO:1 or SEQ ID NO:32).

VHH usually display 2 cysteine amino acid residues (hereafter cysteines) that could form intramolecular disulphide bond. They do not contain an odd number of cysteines that could form intermolecular disulphide bonds and generally speaking do not have the capacity to form homodimers. It has been contemplated to generate fusion proteins of VHH or otherwise produce multimeric VHH. However, in the prior art only dimerization strategies involving the C-terminal region of the VHH (or VHH-derived) protein have been reported and disulphide bond formation has been reported to result in dramatically reduced production yields and VHH solubility (Simmons et al., 2006). In addition, since the small size of VHH is believed to play an important role in their permeability through the BBB, in setups where VHH are used as trans-BBB carriers, dimerization and/or multimerization have not been contemplated. The inventors have surprisingly discovered, and report herein, that it may be advantageous to design the VHH or VHH-comprising polypeptide of the invention so that is has dimerization capacity. In particular, disulphide bond-forming cysteines may be included, especially in the N-terminal region of the VHH or VHH-comprising polypeptide, e.g. in the sequence of the neuron cell-targeting peptide mentioned above. This does not result in decreased expression in bacteria used for their production and results in enhanced activity of the construct. VHH or VHH-comprising polypeptides forming disulphide bonds are readily expressed as dimers in the periplasm of bacteria and the recovery of the construct is easy. It is also possible that the formation of dimers increases the half-life of the VHH or VHH-comprising polypeptide of the invention. In particular embodiments, therefore, the VHH or VHH-comprising polypeptide of the invention has dimerization, especially homodimerization capacity, preferably through the formation of disulphide bonds and/or through domains in the N-terminal region of the VHH or VHH-comprising polypeptide of the invention. In preferred embodiments, disulphide-bond forming cysteines are comprised in the sequence of the neuron cell-targeting peptide fused in N-terminal position of the VHH-comprising polypeptide. Besides, in particular embodiments, the VHH or VHH-comprising polypeptide of the invention is expressed in bacteria in the periplasm and is recovered, and optionally purified, from the periplasm of said bacteria, preferably in the form of homodimers.

The VHH or VHH-comprising polypeptide of the invention is usually for use in applications where one wants to exert a biological effect on brain cells without requiring the direct administration of a product in the brain. The biological effect (e.g. increased survival, proliferation, neurite outgrowth) can sometimes be obtained through known peptides, but these peptides may not have the capacity to permeate across the BBB and/or to target their site of action (e.g. specific cells, cellular compartments, proteins or protein complexes, . . . ) by themselves. When bound to the VHH or VHH-comprising polypeptides described herein, the peptide may be able to retain its activity, while being permeable across the BBB and/or targeted to a specific site of action. The invention therefore provides a VHH or VHH-comprising polypeptide as defined herein, bound to an effector peptide with biological activity on brain cells, particularly fused with said peptide.

A specific family of polypeptides, comprising a MAST-2 binding domain, the Neurovita family, has been described as having neurosurvival and neuroprotective effect and/or to promote neurite outgrowth (WO 2010/116258 A1, WO 2013/068430 A2). Although the use of such Neurovita peptides has been contemplated for therapeutic applications, they are unable to permeate across the BBB efficiently by themselves, which hinders their use in applications where the CNS must be targeted. It has been disclosed to use a delivery system based on expression vectors (e.g. transduced ex vivo in an individual's cells) to express the peptides in the brain, but this has numerous drawbacks, including safety considerations related to the use of expression vectors, as well as pharmacokinetic considerations, since the time from administration to actual efficient expression with this type of delivery is expressed in days, which is too slow for many applications (such as repair/recovery of neurons after an injury or stroke), while the half-life of the vector, of the order of weeks, may be much too long. Lentiviral vector based-delivery, in particular, has been disclosed and although mRNA is readily detected, the short half-life of the peptide leads to hardly detectable protein levels. Delivery systems based on cell-penetrating systems such as the HIV-1 derived TAT peptide for neurovita peptides have also been disclosed. However, the low efficiency and/or short-half life of the fusion peptide required the use of high doses of peptide, with potential toxic effects (Préhaud et al., 2010).

The inventors have surprisingly discovered that Neurovita peptides may retain their biological activity when fused at the C-terminal extremity of a VHH or VHH-comprising polypeptide of the invention and are efficiently delivered across the BBB, e.g. when injected intravenously, and that such fusions promote neurite outgrowth and/or neurosurvival and/or neuroprotection and allow the repair/recovery of neuron cells after a lesion. Therefore, the invention provides with Neurovita peptides, fused in C-terminal with a VHH or VHH-comprising polypeptide as described herein, thereby providing a VHH-comprising polypeptide of the invention having specific activity on neurons. In particular embodiments, the Neurovita peptide has the sequence of SEQ ID NO:7.

The efficient delivery across the BBB of a cargo peptide, bound to (or included in) a VHH or VHH-comprising polypeptide of the invention allows to envision the use of such a construct for therapy, especially of diseases involving the CNS, such as neurodegenerative diseases, or of brain cell damage-associated conditions such as brain stroke or injury, or of the evolution of such disease or condition. Such uses may involve compositions suitable for in vivo administration, especially for intravenous injection, comprising a VHH or VHH-comprising polypeptide of the invention and optionally other pharmaceutically acceptable constituents. The invention therefore provides such compositions. The invention also provides therapeutic methods using the VHH, VHH-comprising polypeptides, and/or composition of the invention. The invention also provides such VHH, VHH-comprising polypeptides, and/or compositions of the invention for use as a medicament or in the manufacture of a medicament, especially a medicament for use in the therapy of neurodegenerative diseases or brain cell damage-associated conditions. In particular embodiments, the therapy comprises the intravenous injection of the VHH, VHH-comprising polypeptides, and/or compositions of the invention.

Methods to produce a VHH or VHH-comprising polypeptides of the invention, polynucleotides encoding these polypeptides are described herein and are part of the invention. The VHH stands among the essential elements of the products of the invention. The main feature of said VHH is its permeability across the BBB, or capacity to cross the BBB, preferably in the context of a VHH-comprising polypeptide. In preferred embodiments, the VHH of the invention does not recognize any brain antigen, particularly any human brain antigen, and/or the VHH, VHH-comprising polypeptide and/or VHH of the VHH-comprising polypeptide do/does not bind specifically to any brain protein, particularly any human brain protein. Methods to prepare VHH bearing said feature are described in detail. In specific embodiments, the selected VHH or VHH-comprising polypeptide has a basic pI. In specific embodiments, the selected VHH and/or preferably the VHH-comprising polypeptide efficiently permeates across (or is able to cross) the BBB, especially efficiently permeates across the endothelial cell layer mimicking the BBB in an in vitro model of the BBB.

In specific embodiments, the VHH or VHH-comprising polypeptide of the invention may form homodimers. In specific embodiments of the methods to produce a VHH or VHH-comprising polypeptide of the invention, said VHH or VHH-comprising polypeptide is expressed in cells, preferably in bacterial cells. In specific embodiments of said methods, said VHH or VHH-comprising polypeptide is recovered in the periplasm of bacteria.

Despite efforts to overcome the junctional or efflux barriers or to circumvent the BBB, most of the newly developed neuropharmaceuticals fail due to poor CNS pharmokinetics. Therefore, the early screening of these molecules on a pertinent and reliable BBB model for their penetration and their interaction with the barrier is crucial. Due to changes in legislation and ethical issues related to animal experimentation, the development of in vitro human BBB model is of major interest for basic research and industrial companies. In vitro models to test for permeability across the BBB present great interest in the development of substances intended to permeate across the BBB, especially substances for use in therapy and/or diagnostics, especially of diseases affecting the CNS. Such models also present interest for research and development related to the BBB. Currently, in vitro models used in such applications include models where the BBB itself is mimicked by a confluent layer (monolayer, or several layers) of endothelial cells, which may be grown e.g. on a filter. The filter may be placed in a cell culture container, in such a way that it separates the cell culture container in two compartments, preventing passive diffusion of macromolecules from one compartment to the other. In such models, a substance may be incubated in one of the compartments, and its permeability can be measured by measuring the quantity of substance found in the other compartment after a given time and/or its effect on the BBB can be measured by measuring i.e. the viability of endothelial cells constituting the confluent layer (Weksler et al., 2005, U.S. Pat. No. 8,084,254 B2, WO 2006/056879).

However, it is recognized that such simple models cannot accurately reflect the in vivo behaviour of the BBB. In particular, it is recognized that, in addition to endothelial cells constituting the BBB itself, the effect of environing cells, particularly of cells found in the brain, is significant. More sophisticated models have therefore been developed, which comprise, in addition to the layer(s) of endothelial cells, neuronal cells and/or glial cells, including e.g. astrocytes (Bicker et al., 2014, EP 1 964 915 A1). However, such models usually make use of rodent/bovine cells, while it is recognized that a reliable model should consist in cells from human origin. Microglial cells constitute important components of the BBB environment. However, most models of the prior art are devoid of such cells, in particular because of their inflammatory effect, which is thought to be damageable to the model. Indeed, activated microglial cells have been shown to induce dysfunction of the BBB (in particular of endothelial cells), while their activation may result from numerous stimuli and is difficult to avoid in in vitro culture (Sumi et al., 2010). Moreover, while models consisting of immortalized cells have been described as showing poor barrier properties (Lippmann et al., 2013), such models would have, essentially practical, advantages. The inventors have surprisingly found that an in vitro brain model as described above consisting of human immortalized cells comprising, in addition to the confluent (mono)layer(s) of endothelial cells, neurons, astrocytes and microglial cells in one compartment, is readily usable for in vitro studies related to the BBB, such as assessing permeability across, or effect on the BBB of a substance, and the targeting and effect to brain parenchyma cells (neurons, astrocytes, microglia) of molecules or microorganisms that have been able to cross previously the BBB.

The invention therefore comprises devices, especially devices suitable for use as in vitro models of the BBB, which comprise or consist in a cell culture container, separated in two compartments by one or more confluent layers of human endothelial cells impermeable to passive diffusion of macromolecules, and comprising human microglial cells in at least one compartment (the "brain compartment" as defined herein). In particular embodiments, the brain compartment comprises other cells, in particular non-microglial human brain cells, in addition to microglial cells, and microglial cells preferably represent 1.5% to 24% of cells in the compartment containing them (the brain compartment). In particular embodiments, the non-microglial brain cells are human neuron cells and/or astrocytes. In preferred embodiments, the endothelial cells, the microglial cells and/or the other cells are human cells, preferably immortalized human cells. The invention provides in particular the use of Ntera-2clD/1 cells in the manufacturing of a BBB and BBBs comprising such cells, as neurons and/or astrocytes in the brain compartment. The invention also provides a cell line, SK-N-SHD, which may be grown in conventional cell culture medium and differentiates to neuronal cells when seeded in NeuroGRO™ or similar media. This cell line is provided in particular for seeding the brain compartment of a BBB model, and models comprising such cells are also provided. The invention further provides methods for the preparation of such devices, including optimal culture media that would be compatible for all the cells types that are present. The invention also provides uses for such devices, especially as an in vitro model of the BBB. Particular embodiments include methods for testing the permeability of a test substance across the BBB and/or methods for testing the toxicity of a test substance on the BBB, said methods including the incubation of said test substance in the devices of the invention. These methods will usually include incubating said tests substance in a compartment of said device and, after a given incubation time, i) measuring the quantity of test substance in the other compartment and/or ii) measuring the viability of cells, including the endothelial cells and/or the "target cells" (neurons, astrocytes, microglia).

BRIEF DESCRIPTION OF DRAWINGS

FIG. 1. Schematic representation and expression of specific VHH-COMPRISING polypeptides A. Structure of VHH1, VHH2 and VHH3. RDP=neuron cell targeting peptide (SEQ ID NO:1); VHH (SEQ ID NO:3); StrepTag=Strep tag (SEQ ID NO:5); PDZ-BS=Neurovita peptide (SEQ ID NO:7); delta-PDZ-BS (in VHH3)=Neurovita peptide devoid of PDZ-BS and thus inactive (SEQ ID NO:9). The black line connecting "S" symbols depicts a disulphide bridge between cysteine residues of the RDP. B. The VHH-comprising polypeptides of the invention were produced and purified by immunoaffinity with an anti-strep antibody and their expression assessed in Western blot. 1=VHH1, 2=VHH2, 3=VHH3. C. PAGE (polyacrylamide gel electrophoresis) analysis of the Neurovita-Neurocargo construction of the invention (VHH1) in denaturating (lane 1) and non-denaturating (lane 2) conditions, showing the dimeric presentation of the polypeptide. To the left of lane 1, approximate molecular weights are indicated. To the right of lane 2, the monomeric form is indicated by "M", and the dimeric form by "D". D. The VHH A12 was shown by western blotting not to recognize any brain protein. Western blotting was performed with VHH A12 or H8/E9 on human brain extract (Sg tau 4697; lane 1), a mouse brain extract (Tg 4510; lane 2) and on a purified protein, GFAP, a specific marker of astrocytes (lane 3). E. The VHH A12 was shown by immunohistochemistry not to recognize any brain protein. Immunohistochemical staining was performed using VHH A12 or AT8 mAb on tg 4510 paraffin-embedded mouse brain sections, shown at 1.25× and 20×. AT8 recognized NFTs present in brain tissues. Scale is indicated by the thick black bar.

Binding of VHH-comprising polypeptides to AchR alpha 7 expressing HEK293 cells was assessed by FACS after 30 min at 4° C., in the presence of competitors. A. Rabies virus (RABV) competition. Horizontal axis: Cy5 intensity (logarithmic scale). Vertical axis: cell counts. The "C" curve is the control curve. In the absence of RABV ("–", top row), VHH1 readily binds cells, while VHH2 (devoid of neuron cell-targeting peptide) binding is not distinguishable from the control (the graph actually does not allow to distinguish curves of VHH2 and the control). The black arrows show the shift of the peak. In the presence of RABV ("+", bottom row), a 54% decrease of VHH1 binding is observed. B. alpha-bungarotoxin competition. Axis and arrows as in panel A. The presence of alpha-bungarotoxin ("+" curve) does not modify binding of VHH2, while it reduces binding of VHH1 by 58%. C. Comparison of binding of VHH1, VHH2, VHH3. Binding of the VHH-comprising polypeptides was tested in the absence (–) or presence (+) of Rabies virus (RABV), expressed in relative units (RU). "**" denotes a p-value<0.004 in Student's t-test.

Figure 3A:
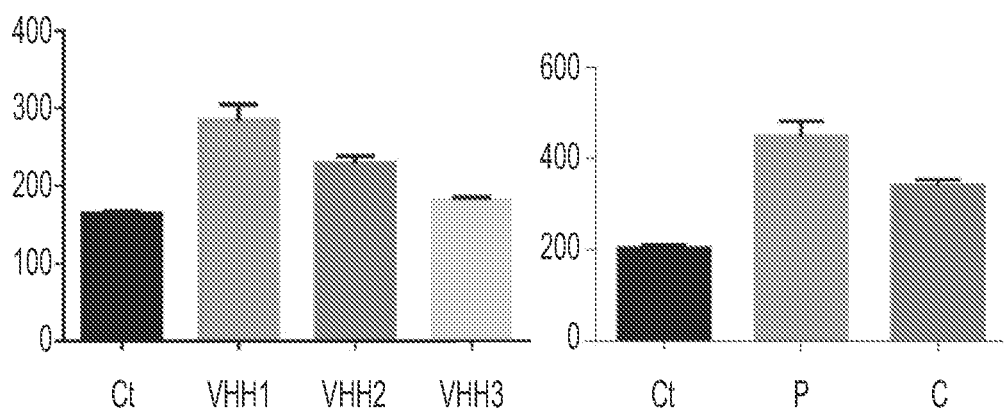
Figure 3B:
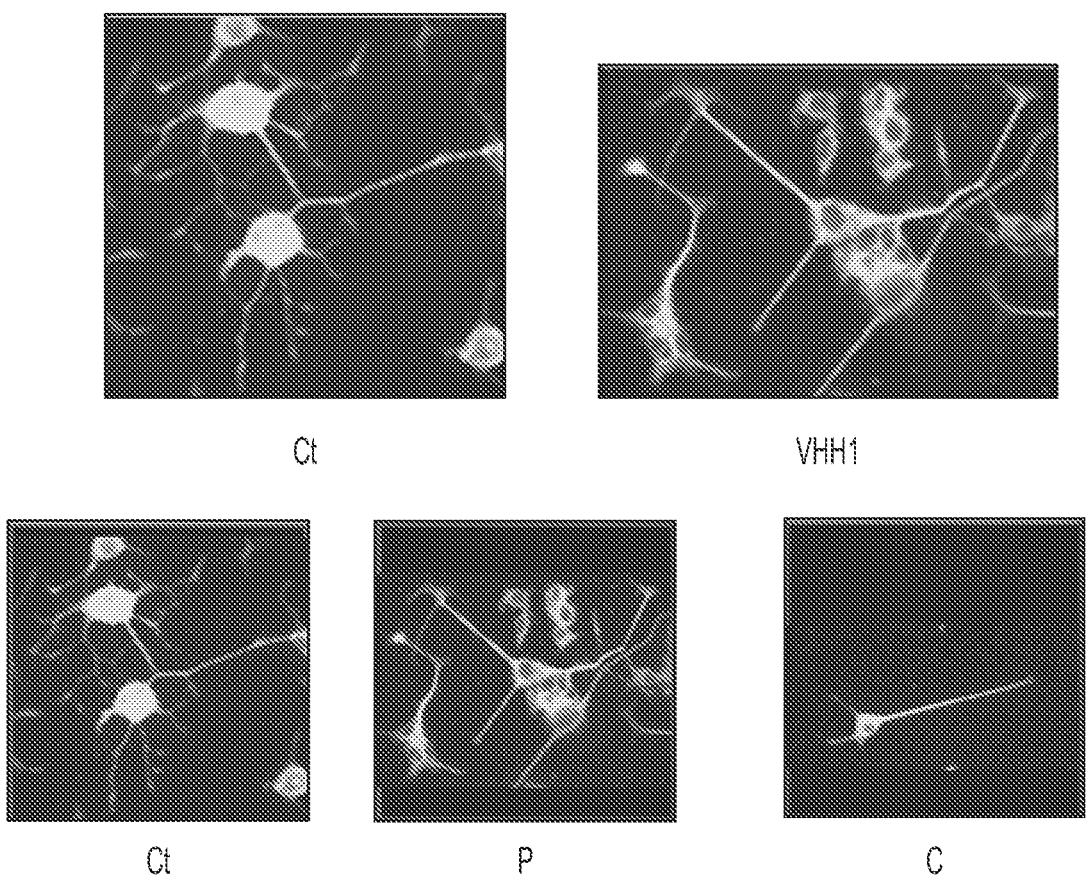

FIG. 3. Stimulation of neurite outgrowth by VHH-comprising polypeptides

A. Neurite outgrowth assays for Control cells (Ct) or cells in the presence of VHH-comprising polypeptides of the invention VHH1, VHH2 and VHH3 (left panel) or the periplasmic (P) or cytoplasmic (C) fractions of VHH1 expressed in bacteria (right panel) were performed as described in the Examples section. VHH1 is produced in the cytoplasm as a monomer. Vertical axis: average neurite length per neuron in μm. An ANOVA test showed a p-value<0,0001 in every case. B. Microscopy images corresponding to experiments in panel A (at 72 h incubation). VHH1 in the cytoplasmic fraction (monomeric) stimulates neurites outgrowth but less than VHH1 in the periplasmic fraction (homodimeric) and does not trigger large growth cone expansion.

Figure 4A:
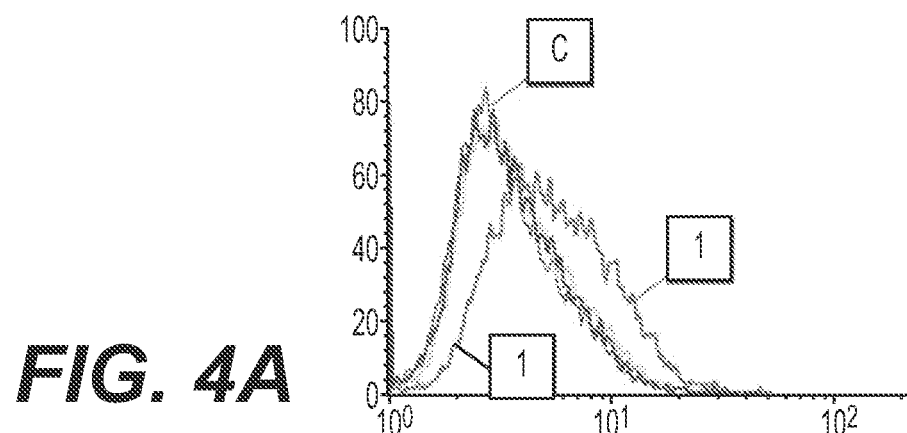
Figure 4B:
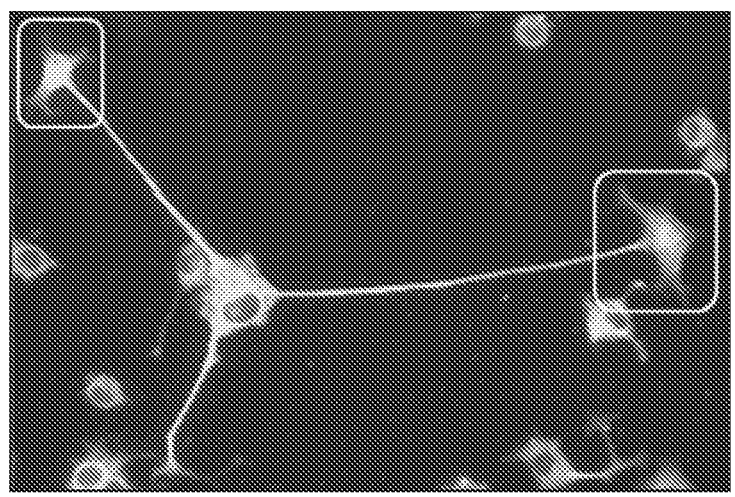
Figure 4C:
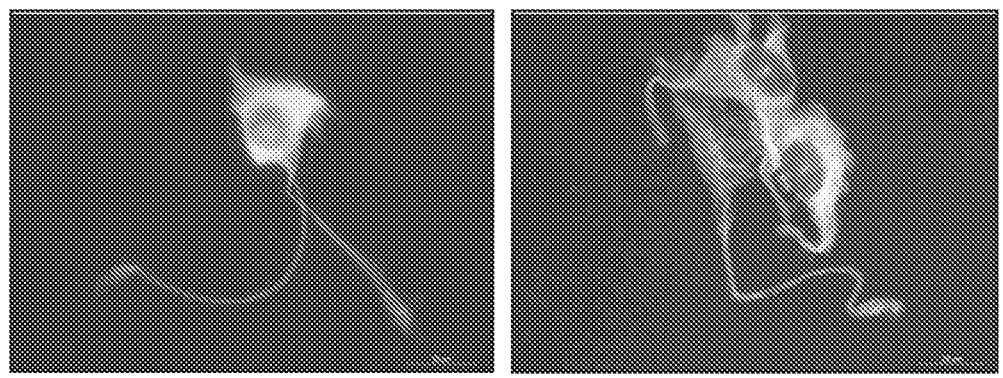

FIG. 4. VHH-comprising polypeptides binding and entry in neurons

A. Binding and entry of VHH-comprising polypeptides to differentiated NS cells was assessed by FACS after 30 min at 4° C. Horizontal axis: Alexa 488 intensity (logarithmic scale). Vertical axis: cell counts. The "C" curve is the control curve, the "1" curve is the VHH1 curve. VHH1 readily binds cells, while VHH2 and VHH3 binding is hardly distinguishable from the control (the graph actually hardly allows to distinguish curves of VHH2, VHH3 and the control). B. Immunofluorescence of VHH1 in NS cells treated for 72 h with VHH1. The boxes show the neuron growth cone C. Immunofluorescence of actin in control (Ct) and VHH1-treated (48 h, VHH1) of differentiated NS cells. Arrowheads show intense staining corresponding to actin clearly visible in the original color images. VHH1 stimulates growth cone motility.

Figure 5A:
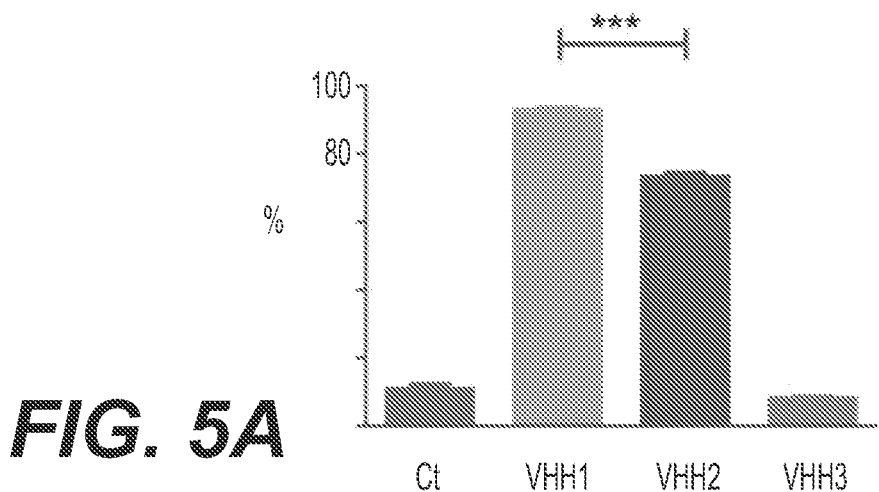
Figure 5B:
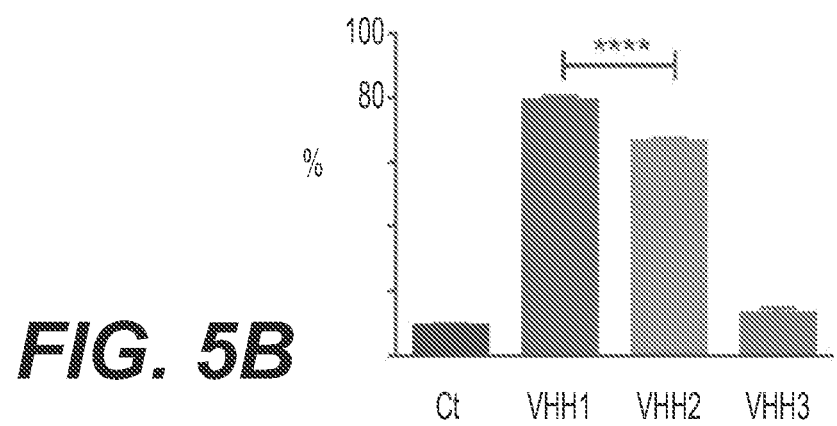
Figure 5C:
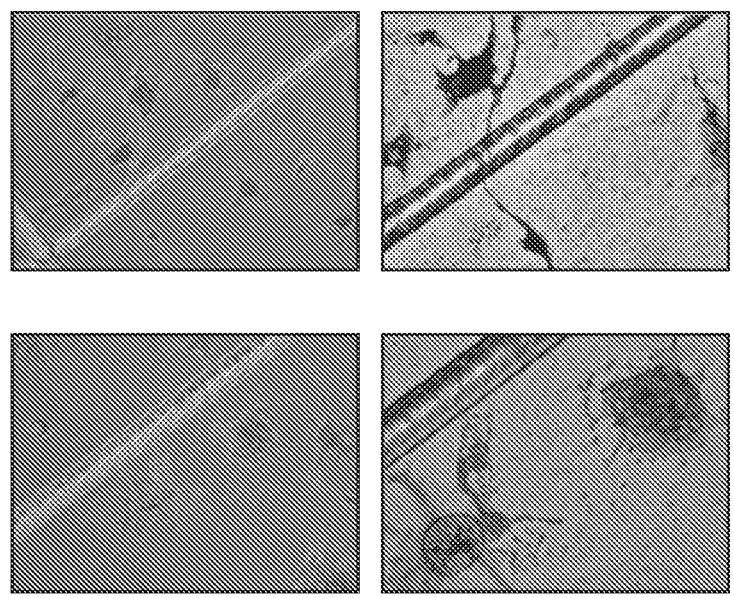

FIG. 5. Triggering of axon regeneration post wounding by VHH-comprising polypeptides A. A scratch assay was performed where NT2-N were preincubated without (Ct) or with a VHH-comprising polypeptide (VHH1, VHH2 or VHH3) for 4 hours prior to wounding the cells. The assay was read after 72 h of incubation (i.e. 68 h after wounding). Vertical axis: average percentage of neurons in regeneration. (*) or (**) denotes a p-value<0.0001 in a Student's t-test B. Similar experiment and symbols as in panel A, but the wounding was performed 1 h before the addition of the VHH-comprising polypeptide and the reading 72 h after wounding (i.e. after 71 h of incubation of the polypeptide). C. Typical images showing regeneration (top row) or lack of regeneration and cell destruction (bottom row) 3 days post-scratching.

Figure 6A:
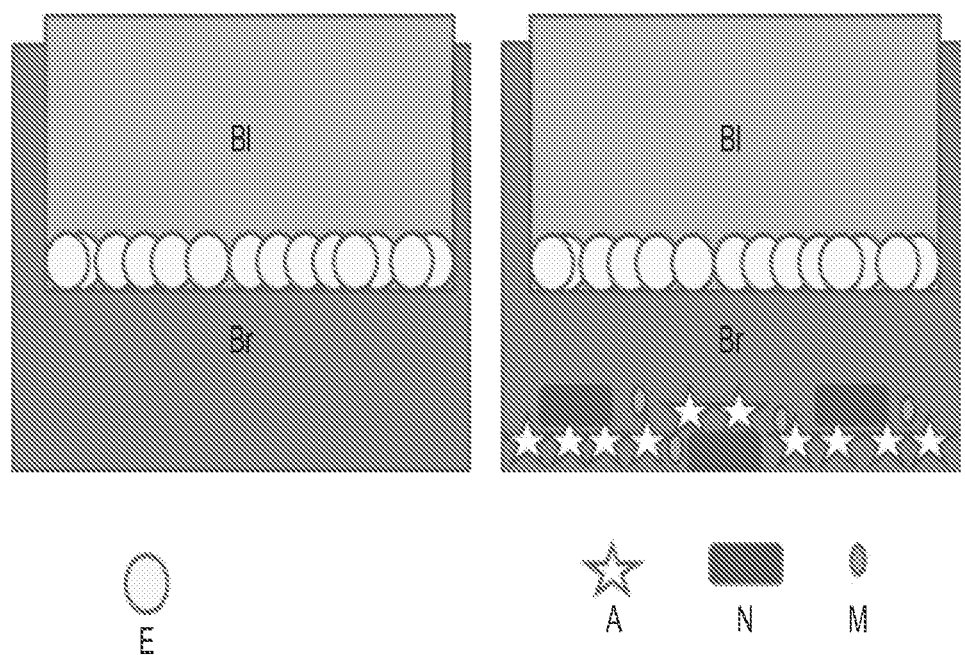
Figure 6B:
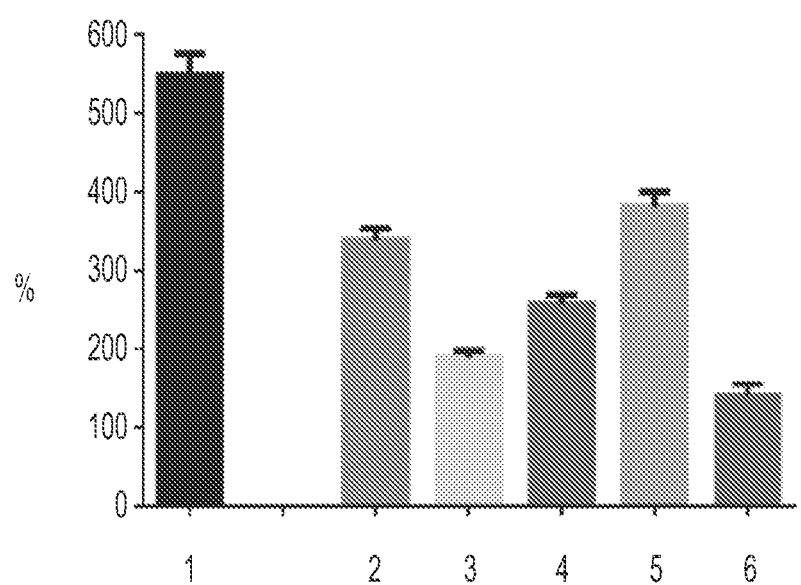

FIG. 6. In vitro model of the human Minibrain-BBB

A. Schematic representation of in vitro models, shown as a cross-section of a cell culture well. Left panel, models of the prior art, devoid of cells in the brain compartment; right panel: model of the invention. Br: brain compartment; BI: injection compartment, corresponding to the "blood" side of the BBB; E: endothelial cells; A: astrocytes; N: neurons; M: microglial cells. B. Phenotype of minibrain cells, 24 h after addition of the well containing the endothelial cells. mRNA expression of several genes was measured in cells forming part of the model of the invention, in NT2-N cells: 1=tyrosine hydroxylase (TH), a marker of neuron cells, or in NT2-N, NT2-A and CHME cells: 2=neurofilament protein H (NEFH), a marker of neuron cells; 3=glial fibrillary astrocytic protein (GFAP), 4=aquaporin 4 (AQP4), and 5=glycogen phosphorylase B (PYGB), markers of astrocytes; 6=CD 200 receptor (CD200R), a marker of microglial cells. Vertical axis: % of mRNA expression compared to control.

Figure 7A:
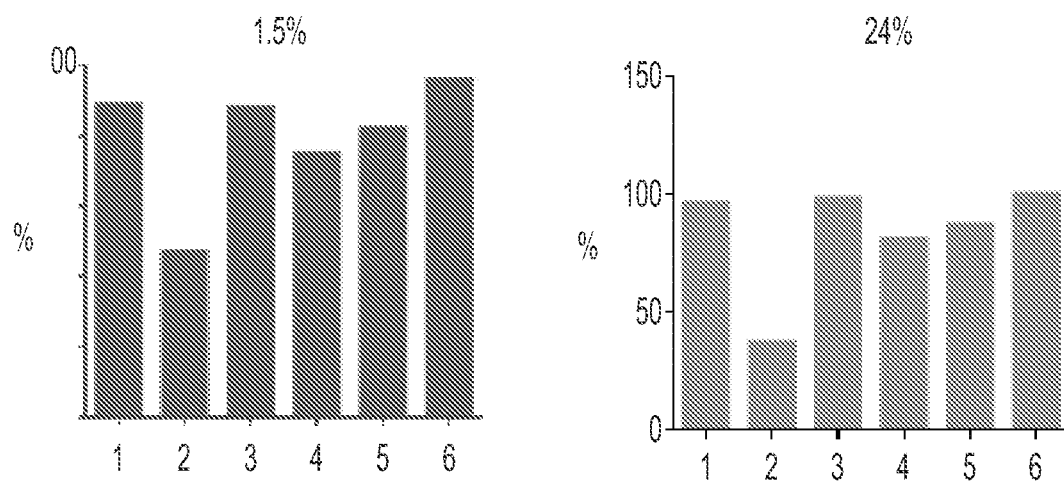
Figure 7B:
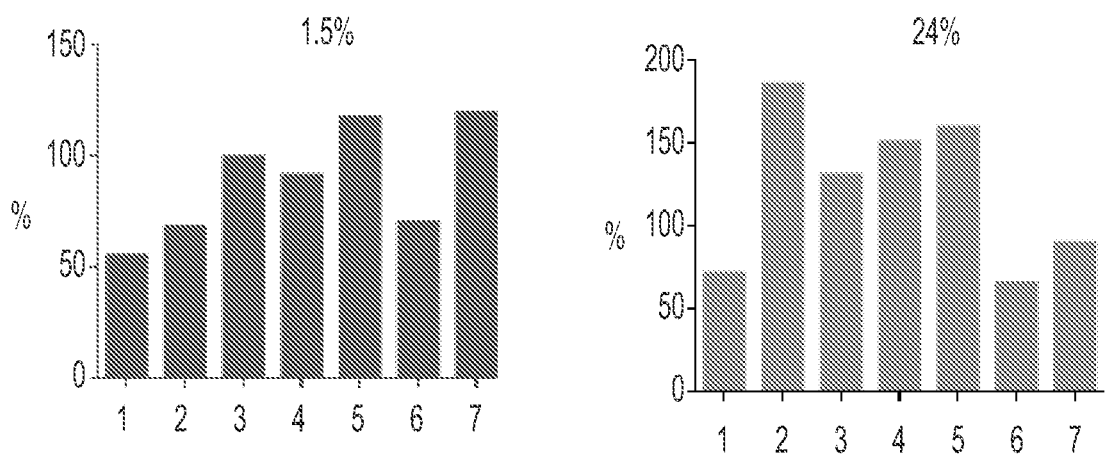
Figure 7C:
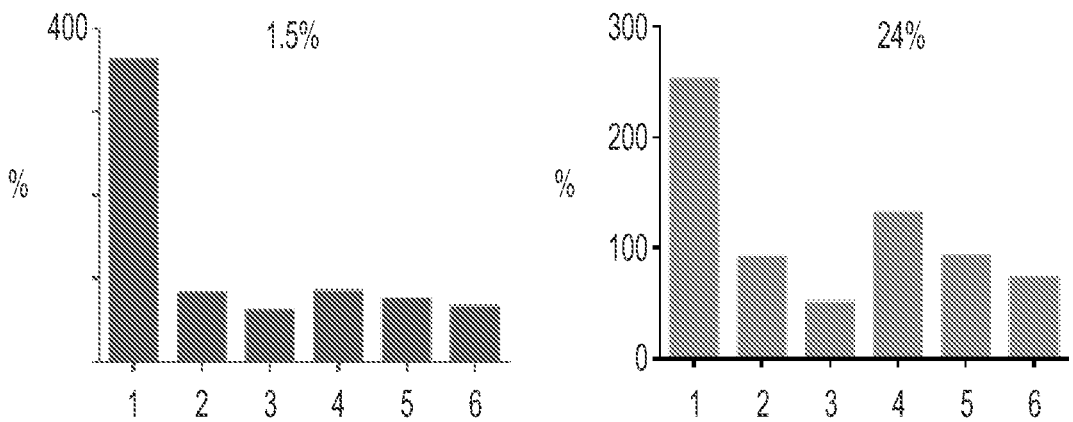
Figure 8A:
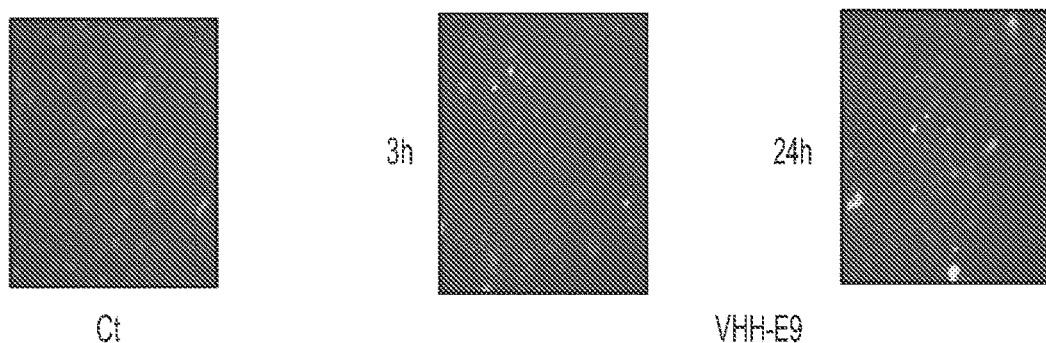
Figure 8B:
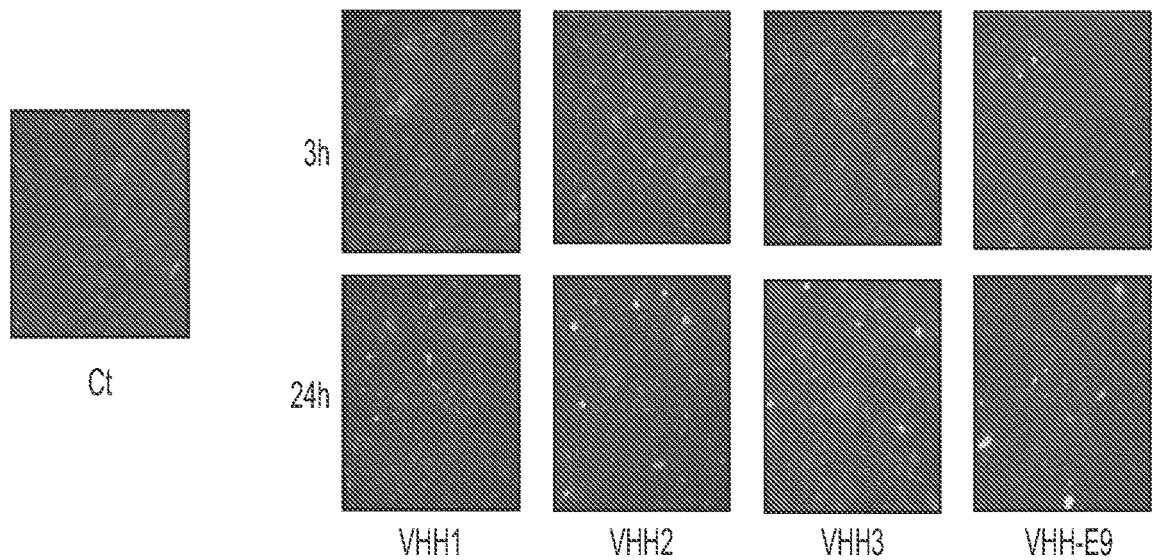
Figure 8C:
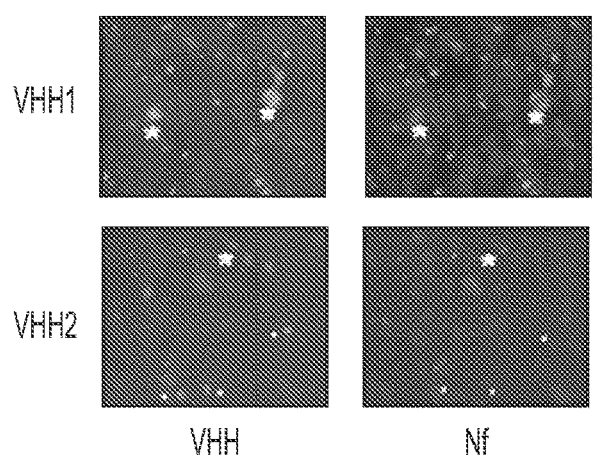
Figure 8D:
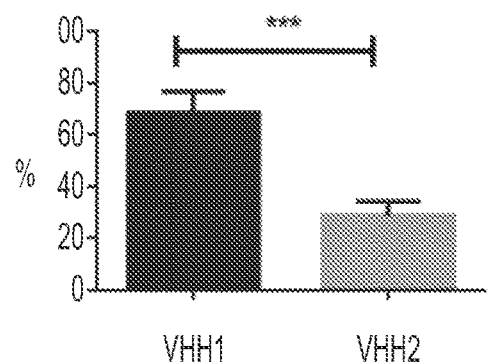

FIG. 7. Q-PCR Characterisation of endothelial cells in the Minibrain-BBB model mRNA expression of several genes was measured in endothelial cells forming part of the model of the invention, 24 h after they were added to the cell culture container containing the brain cells, said model being prepared with either 1.5% (left panels) or 24% (right panels) of microglial cells. Vertical axis % of mRNA expression compared to control. A. Efflux transporters: 1=ABCB1 protein, 2=ABCG2 protein, 3=multidrug-resistance associated protein (ABCC1), 4=ABCC2 protein, 5=ABCC4 protein, 6=ABCC5 protein. B. Receptors: 1=low density lipoprotein receptor (LDLR), 2=low density lipoprotein receptor related protein 1 (LRP1), 3=insulin receptor (INSR), 4=leptin receptor (LEPR), 5=basal cell adhesion molecule (LU), 6=CD71 antigen (TFRC), 7=advanced glycosylation end-product receptor (AGER). C. Transporters: 1=stimulated byretinoic acid gene 6 protein (STRA6, 2=glucose transporter type 1 (SLC2A1), 3=large neutral amino acid transporter 1 (SLC7A5), 4=solute carrier family 1 protein (SLC1A1), 5=solute carrier family 38 member 5 protein (SLC38A5), 6=monocarboxylate transport protein 1 (SLC16A1). STRA6 is highly expressed and LU is overexpressed in all conditions.

FIG. 8. Targeting of VHH-comprising polypeptides to neurons of the Minibrain-BBB model Fluorescence microscopy assays to determine the capacity of VHH-E9 or of a VHH-comprising polypeptides of the invention to cross the BBB were performed using the device of the invention with 1.5% microglial cells, said VHH-E9 or VHH-comprising polypeptide being incubated for either 3 h or 24 h. VHH-E9 was has been previously shown to cross the BBB in vivo (Li et al., 2012). Ct=control, i.e. secondary antibody only. A. Fluorescence images showing the presence of VHH-E9 (which is A488-conjugated) in the brain compartment after 3 h or 24 h. B. Fluorescence showing the presence of VHH-E9 (A488-conjugated) or of the VHH-comprising polypeptides of the invention VHH1, VHH2, VHH3 (using an anti-strep-tag antibody) in the brain compartment after 3 h or 24 h of incubation. VHH-E9 and the VHH-comprising polypeptides of the invention VHH1, VHH2 and VHH3 cross the BBB in vitro model of the invention. C. Fluorescence images showing the targeting of VHH-comprising polypeptides of the invention (VHH1 or VHH2) to neurons of the brain compartment after crossing the BBB. Images obtained as in B, after 24 h incubation, and with simultaneous staining of neurofilament 200 kDa (Nf), which is a marker of neurons. Left images: VHH staining (green channel); right images: Nf staining (red channel). The white stars denote neurons stained with the VHH-comprising polypeptide (i.e. staining is detected in both channels), while the white dots denote cells with VHH2 staining and no Nf staining. No such cells are present in the VHH1 images. D. In the experiment described in C, the efficiency of neuron targeting was measured for VHH1 and VHH2. Vertical axis: percentage of Nf stained cells (neuron cells) among cells stained for the corresponding VHH-comprising polypeptide. (***) denotes a p-value<0.0002 in Student's t-test. VHH1 targets neurons after crossing the BBB.

FIG. 9. Sequence alignment of the VHH A12 with VHHs of the prior art

The sequence of the VHH moiety of the VHH-comprising peptides disclosed herein (VHH A12) was aligned with the sequences available from public databases for VHHs (EMBL: uniprotkb, uniprotkb_swissprot, uniprotkb_swissprotsv, uniprotkb_trembl, epop, jpop, kpop, uspop, nrpl1, nrpl2, uniparc). All VHHs with an alignment score higher than 419 are included in the alignment. The residues of the CDR regions are in bold font and double underlined. As can be seen, exemplary features of the VHH of the invention include a GF sequence in positions 5-6 of CDR2, where most VHHs have GG and others have GR; a DV sequence in positions 2-3 of CDR1, where position 2 is most often F (R, V and L are all represented once) and position 3 is most often S, sometimes G or R; and similarly unique features are found in CDR3 and in the framework regions.

Figure 10A:
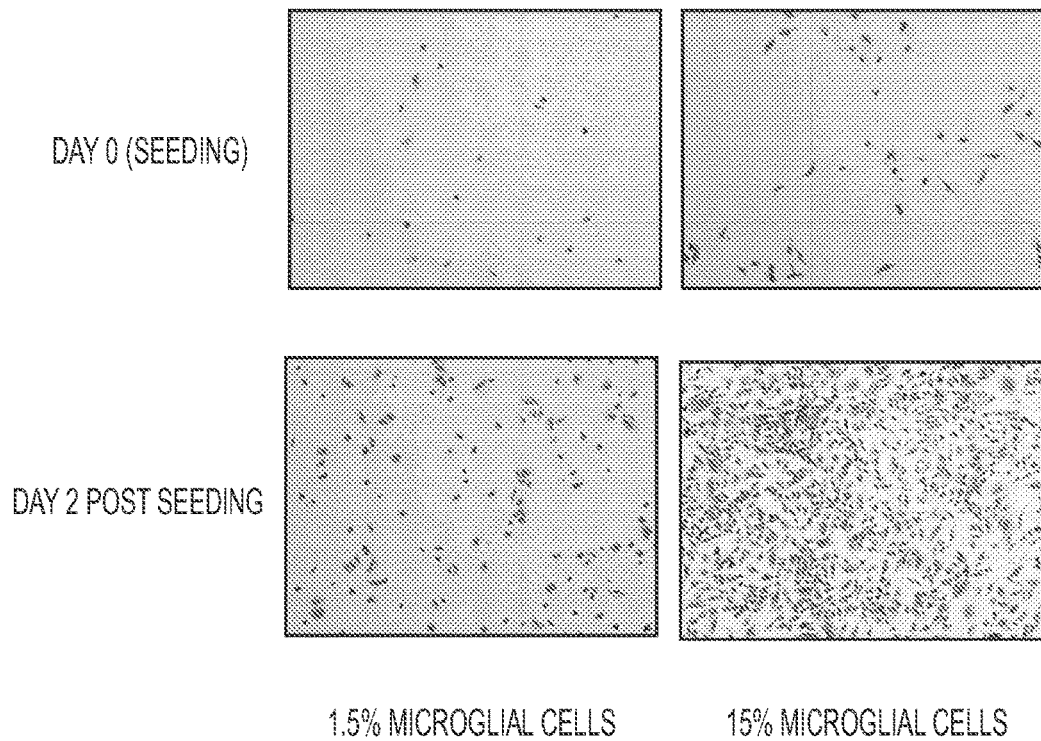
Figure 10B:
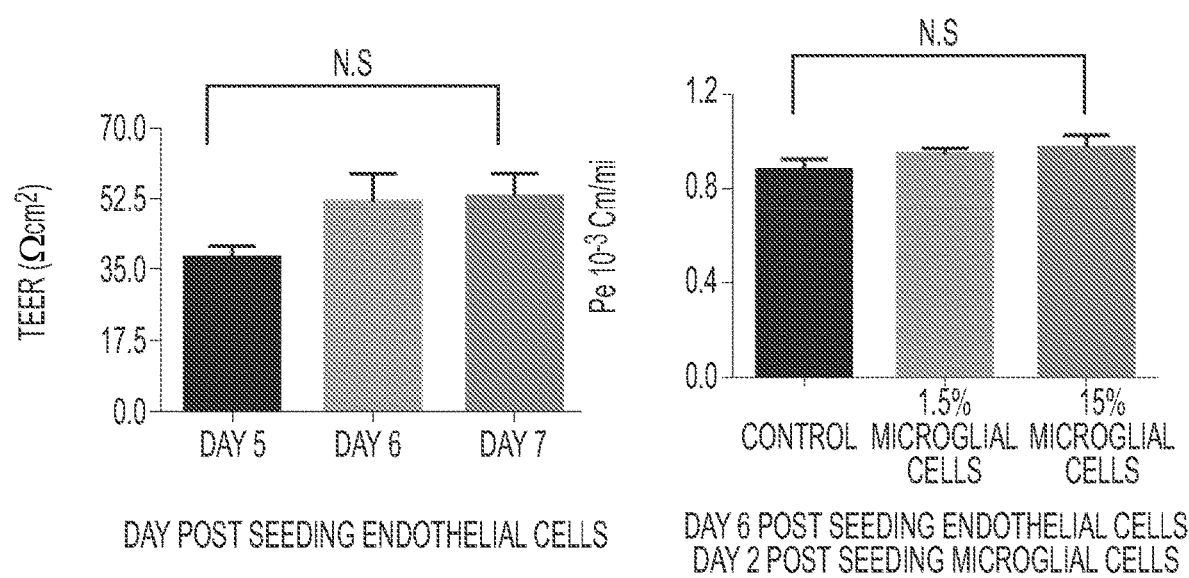

FIG. 10. Test of the device of the invention with various ratios of microglial cells A. Microscopy images showing the cells of the brain compartment at the day of seeding (day 0) and two days later (day 2), when the BBB model described herein is seeded with 1.5% microglial cells (left) or 15% microlglial cells (right). In the BBB seeded with 15% microglial cells, such cells appear to constitute 80% of cells two days after seeding. B. Restrictive paracellular permeability of the BBB model seeded with 1.5% or 15% of microglial cells. Permeability, measured by transendothelial electrical resistance (TEER, left) and by endothelial permeability coefficient ($P_e$, right) is shown for the BBB model seeded with 15% microglial cells at various time points after seeding of endothelial cells (left) and for the model seeded without microglial cells or with 1.5% or 15% microglial cells 2 days after seeding of microglial cells (right). As is observed, in the BBB disclosed herein, the presence of microglial cells even at high ratio does not have any deleterious effect on the permeability of the barrier.

Figure 11A:
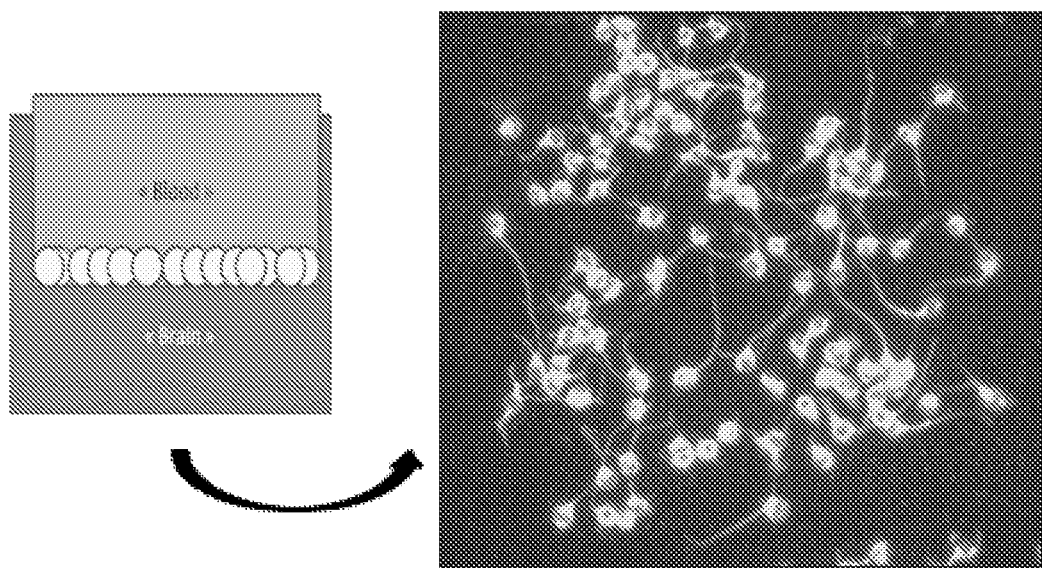
Figure 11B:
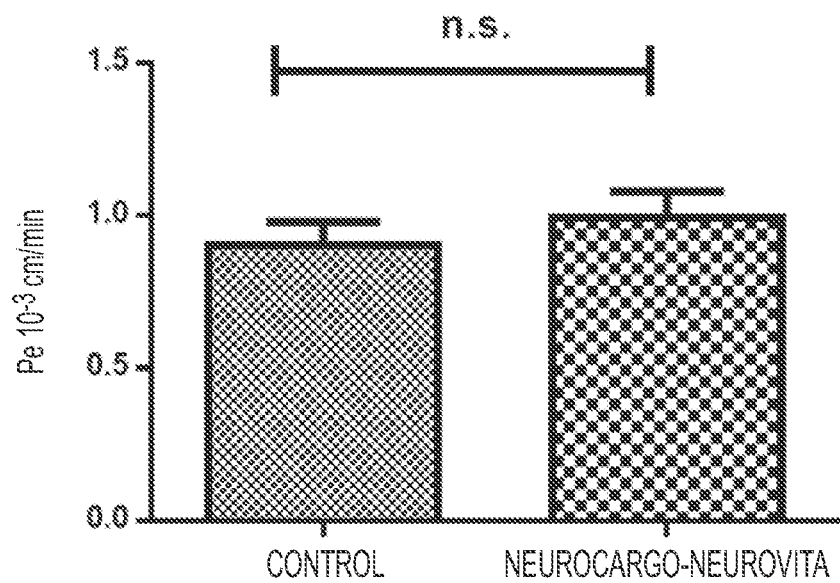

FIG. 11. "Mini-minibrain"

The "mini-minibrain" device, i.e. the BBB model disclosed herein was produced using the SK-N-SHD cell line as the source of neuron cells in the brain compartment. A. schematic representation of the device and fluorescence microscopy image of the brain compartment, showing strong B3 tubulin labelling. B. Permeability coefficient ($P_e$) of the mini-minibrain measured in the absence (control) or presence of neurocargo-neurovita, demonstrating that the permeability is not altered by the VHH-comprising polypeptide disclosed herein. Fluorescence microscopy confirmed that in these conditions, neurocargo-neurovita is transported across the BBB and is targeted to the cells of the brain compartment.

DETAILED DESCRIPTION OF THE INVENTION

General Definitions Relating to the Features of the Invention and Disclosure of Embodiments Thereof Peptide or Polypeptide A peptide or polypeptide is a macromolecule consisting in amino acid residues linked by peptide bonds. The terms peptide and polypeptide are used herein interchangeably, although peptide usually designates shorter sequences (typically less than 50, or less than 30, or less than 20 amino acid residues) while polypeptides usually designates longer sequences (typically more than 20, 30 or 50 amino acid residues). The term protein is used herein interchangeably with the term polypeptide. The amino acid residues may be selected among the 20 naturally occurring amino acids, and/or among non-naturally occurring amino acids, which are known to the skilled person. The amino acid residues may be modified, either by naturally-occurring modifications or by non-naturally occurring modifications. Naturally-occurring modifications comprise phosphorylation, especially of serine, threonine and/or tyrosine residues, glycosylation, including N-linked and O-linked glycosylation, ubiquitination, especially of lysine residues, SUMOylation or other modification by Ubiquitin-like proteins, etc.

In particular embodiments, the polypeptides of the invention are non-naturally occurring, i.e. they are not found in nature and/or are not products of nature and are significantly different from products of nature. Such difference may arise from the amino acid sequence of said polypeptide. As an example, a polypeptide consisting in or comprising a fusion of at least two polypeptides found in different species, especially species from different families (e.g. a camelid and a virus) will usually have a sequence that is not found in naturally-occurring polypeptides. As another example, the polypeptide may have at least one mutation in a conserved amino acid residue of its sequence, i.e. the amino acid in a given position may be one that is not found in this position in naturally occurring polypeptides. The difference may also arise from the presence of non-naturally occurring amino acids. The difference may also arise from a modification in at least one amino acid residue which is a non-naturally occurring modification. The difference may also arise from the addition of molecular moieties which are not found appended to naturally-occurring polypeptides. The difference may also arise from the presentation of the polypeptide, i.e. the macroscopic format in which the polypeptide is produced, presented or used. In particular, the polypeptide of the invention may be in a format suitable for convenient manipulation, e.g. in a test tube or other artificial container, especially when no biological membrane separates the polypeptide from other components in the tube, i.e. direct molecular contact may occur without delay between the polypeptide and other molecules and macromolecules added in the container before or after the polypeptide. Fusion proteins/fusion polypeptides are terms used herein in their usual meaning of a polypeptide comprising or consisting of at least two peptides linked by a peptide bound. In practice, such a fusion is a single polypeptide with a sequence corresponding to the concatenated sequences of the peptides comprised in the fusion. When a fusion protein/polypeptide is described herein, and except where explicitly excluded or technically irrelevant (as appreciated by the skilled person in the specific context where it appears), the fusion may comprise a spacer peptide (as described herein) or any number of spacer or other peptides intercalated between the peptides explicitly described. As will usually be clear from the context, "a fusion polypeptide comprising polypeptide A and polypeptide B" designates herein "a fusion polypeptide of polypeptide A and polypeptide B and optionally other polypeptides (including spacer peptides)" and "a fusion polypeptide consisting of polypeptide A and polypeptide B" designates herein "a fusion polypeptide of polypeptide A and polypeptide B and an optional spacer peptide". When stated herein that "a polypeptide A is fused with a polypeptide B", it is not implied, unless explicitly stated, that both polypeptides are necessarily fused directly to each other or through a spacer peptide, i.e. the peptides may be separated by any number of peptides and may be in any order. When stated herein that "a polypeptide A is fused C-terminally to a polypeptide B", it is not implied, unless explicitly stated, that both polypeptides are fused directly to each other or through a spacer peptide, i.e. A and B may be separated by any number of peptides and residues, provided A is closer to the C-terminal extremity of the fusion polypeptide. Similarly, "a polypeptide fused N-terminally to polypeptide B" is closer to the N-terminal extremity of the fusion polypeptide, but may be separated by any number of peptides and residues from the polypeptide B.

In a first aspect, the invention thus relates to a polypeptide having a sequence comprising or consisting of a VHH of a camelid heavy-chain antibody with the sequence of SEQ ID NO:3, or a variant or a portion thereof as detailed below, wherein said VHH is permeable across the blood-brain barrier and does not recognize any brain antigen and/or does not bind specifically, especially through antibody/antigen interaction, to any brain protein.

As will be exposed in more detail below, the invention includes polypeptides comprising a VHH as defined herein, with additional optional peptides fused with the VHH and adding desired features. Such polypeptides are described throughout the document as VHH-comprising polypeptide of the invention. However, for clarity, reference to a VHH of the invention or to a VHH-comprising polypeptide of the invention has sometimes been omitted, where in fact the skilled person will appreciate that both the VHH and VHH-comprising polypeptide may be concerned. Therefore, except where irrelevant technically or logically, when a "VHH of the invention" is mentioned, a "VHH-comprising polypeptide of the invention" is also concerned and vice-versa, i.e. one phrase may be substituted by another. The term polypeptide of the invention is sometimes also used to designate both a VHH of the invention and a VHH-comprising polypeptide of the invention.

In particular, the description of features relative to the VHH of the invention also can apply, in most cases, to the VHH-comprising polypeptide, including to a polypeptide comprising or consisting of a sequence variant or portion of the VHH with SEQ ID NO:3 as defined herein, which variant or portion is also encompassed within the invention. More specifically, a VHH-comprising polypeptide of the invention advantageously has a basic pI, and/or is permeable across the BBB; and/or does not recognize any brain antigen and/or does not bind specifically to any human brain protein, and/or does not bind through antibody/antigen interaction to any brain antigen and/or does not bind to any brain antigen through the VHH moiety.

VHH

A VHH is the variable domain of a heavy-chain-only antibody from a camelid (HcAb) or a molecule derived from such a VHH and having substantially the same properties as the original VHH in particular in respect of antigen recognition capacity (including when having no antigen recognition capacity). All the species of the Camelidea family have heavy-chain-only antibodies. In a preferred embodiment, the VHH of the invention is obtained from an alpaca (*Lama pacos*).

The VHH of the invention preferably has the sequence of SEQ ID NO:3. The VHH may also have a variant sequence having at least 70% or at least 80% identity, preferably at least 90% identity, more preferably at least 95% identity and even more preferably at least 99% identity with said sequence. If the VHH of the invention comprises only a portion of the sequence of SEQ ID NO:3, the identity level is calculated on the sequence of said portion. The length of said portion is at least 70%, preferably at least 80%, more preferably at least 90% and even more preferably at least 95% of the length of SEQ ID NO:3. In preferred embodiments, the length of said portion is at least 60 amino acids, at least 80 amino acids, preferably at least 100 amino acids, more preferably at least 110 amino acids and even more preferably at least 115 amino acids. In particular embodiments, the VHH of the invention comprises at least the three CDR regions of the VHH with the sequence of SEQ ID NO:3. In particular embodiments, the VHH comprises a CDR1 with the sequence IDVINNMA (SEQ ID NO:47), a CDR2 with the sequence TITSGFSTNY (SEQ ID NO:48) and a CDR3 with the sequence KVHLIRLGAARAYDY (SEQ ID NO:49). However, the skilled person will appreciate that it may be preferable to introduce mutations in the CDRs e.g. for de-immunization if the VHH is to be administered. Therefore, limited mutations, which preserve the features of the VHH, are also considered. In a particular embodiment, the CDRs of the VHH have limited substitutions in their amino acid sequence, preferably limited to two residues in each CDR and even more preferably to one residue. In a particular embodiment, the VHH of the invention has at least 70% identity (or more, as detailed above) with SEQ ID NO:3 and comprises a CDR1 with a sequence having no more than 2 mismatches, preferably no more than one mismatch, with the sequence of SEQ ID NO:47, and preferably a CDR1 with the sequence of SEQ ID NO:47; a CDR2 with a sequence having no more than 2 mismatches, preferably no more than one mismatch, with the sequence of SEQ ID NO:48, and preferably a CDR2 with the sequence of SEQ ID NO:48; and a CDR3 with a sequence having no more than 2 mismatches, preferably no more than one mismatch, with the sequence of SEQ ID NO:49, and preferably a CDR3 with the sequence of SEQ ID NO:49. A mismatch as meant above is preferably an amino acid substitution, in particular for CDR1 and CDR2, but may be a deletion or insertion of a single amino acid. A mismatch as meant above is preferably a conservative substitution of an amino acid, i.e. a substitution of an amino acid with another amino acid which the skilled person would realize has similar features. Portions, as defined above, of such a VHH also constitute particular embodiments. In a particular embodiment, the VHH of the invention comprises framework sequences as depicted in the sequence alignments of FIG. 9 (the framework sequences correspond to the non-underlined amino acids). In particular, the VHH of the invention may comprise the framework regions of the VHH with the sequence of SEQ ID NO:3, or with at least 80% identity and preferably at least 90% identity to the sequence of these framework regions.

The VHH which is a variant of the VHH with the sequence of SEQ ID NO:3 or a portion thereof shares the essential features of the latter VHH regarding antigen recognition (and in particular does not recognize any brain antigen), binding of brain proteins (and in particular does not specifically bind to any human brain protein), permeability across or capacity to cross the BBB (and in particular is permeable across or is able to cross the BBB, as defined herein) and/or pI (and in particular has a basic pI as defined herein) and embodiments relating to the VHH or VHH-comprising polypeptides of the invention apply to a VHH which is a variant of the VHH with the sequence of SEQ ID NO:3 or a portion thereof. Tests for these features are readily accessible to the skilled person and in particular such tests are disclosed herein, in particular in the Examples section. For the avoidance of doubt, although they might not be strictly sensu VHH fragments of an HcAb of an antibody from a camelidae, or obtainable from a camelidae, the sequence variant and portion of VHH (including of a sequence variant) are included in the term VHH as used herein, except where irrelevant technically or logically. In some embodiments, especially when it has a sequence which is a variant from SEQ ID NO:3, the VHH of the invention is not a naturally-occurring VHH and is preferably not a naturally-occurring protein.

A VHH or VHH-Comprising Polypeptide of the Invention is Permeable Across the BBB.

A substance (e.g. a protein), and in particular a VHH of the invention, which is permeable across the BBB can be defined as one that, when administered outside the part of the brain which is protected by the BBB, can be found in the brain in significant quantity after a reasonable amount of time. In other terms, which are used herein with the same meaning as "is permeable across the BBB", the substance "has the capacity to cross the BBB", or "is able to cross the BBB", the term permeability being used herein with the meaning of "capacity to cross the BBB". Generally, when tested in vivo, the administration is made by intravenous injection, especially in the carotid of an animal, especially a non-human mammal, in particular a mouse or rodent.

Testing the permeability across the BBB in vivo presents with multiple difficulties. A substance, and in particular a VHH or VHH-comprising polypeptide of the invention, which is permeable across the BBB can therefore alternatively be defined by reference to an in vitro BBB model. In particular, in the case of in vitro BBB models comprising two cell culture compartments separated by a confluent layer of cells mimicking the BBB, a substance which is permeable across the BBB may be defined as one that, when applied to and/or incubated in one compartment for a reasonable amount of time, is found in significant quantity in the other compartment.

In the definitions above, amounts higher than 0.01% or 0.1%, preferably higher than 0.5%, 1% or 1.5% and even more preferably higher than 2.5%, 5% or 10% of the initially applied and/or administered substance can be considered, for example, significant quantity. Especially for an in vivo determination of whether a substance is permeable, it may prove difficult or impossible to quantify the amount of substance that has passed the BBB. Since, in particular in vivo, the BBB very efficiently prevents penetration in the brain of most molecules (of sufficient size), the skilled person will appreciate that, with most conventional cellular and/or molecular detection methods, the detection of any quantity of such substance in the brain (or the compartment mimicking the brain) can be considered significant and is a sign of permeability. It will also be appreciated that trace amounts (e.g. amounts detectable only by highly sensitive techniques such as mass spectrometry) of the substance that have crossed the BBB, especially if detected using an in vitro model, will usually not be considered significant. Given the usually observed kinetics of penetration across the BBB of permeable proteins, the skilled person will appreciate that a reasonable amount of time in this context is usually of the order of magnitude of tens of minutes to a few hours. Therefore, the amount of time between administration and testing for the presence of the substance in the brain (or compartment mimicking the brain) can range, for example from 10 min to 12 hours. Typical times for testing in vivo range preferably from 30 min to 12 hours, preferably 30 min, 1 h, 90 min, 2 h, 4 h, 8 h or 12 h. Typical times for testing in vitro range preferably from 10 min to 4 hours, preferably 10 min, 30 min, 45 min, 1 h, 90 min, 2 h, 3 h or 4 h. Longer times are also contemplated, however, factors such as the half-life of the substance may influence the results dramatically when extended incubation times are used, since the substance may be degraded before it is tested and thus may remain undetected, although it effectively crossed the BBB.

In particular embodiments, when tested with the in vitro models described in Weksler et al., 2005, U.S. Pat. No. 8,084,254 B2 or WO 2006/056879 and/or with the in vitro models described in Bicker et al., 2014 or EP 1 964 915 A1 and/or with the novel in vitro BBB model described herein, more than 0.1% of the VHH or VHH-comprising polypeptide of the invention which was initially incubated is found in the "brain" compartment after 4 hours of incubation. In preferred embodiments, more than 0.5%, preferably more than 1% is found after 4 hours of incubation. In further preferred embodiments, more than 0.5%, preferably more than 1% is found after 1 hour of incubation. In yet further preferred embodiments, more than 1.5% preferably more than 2.5% is found after 1 hour of incubation. In particular embodiments, when tested using any of these models containing brain cells, in particular neuron cells, in the "brain" compartment, the VHH or VHH-comprising polypeptide of the invention is readily detected in immunofluorescence experiments in said brain cells, in particular neuron cells, after 3 hours of incubation of 10 pg of the VHH or VHH-comprising polypeptide applied in the other compartment.

The permeability across the BBB of the entire construct (i.e. the entire VHH-comprising polypeptide of the invention, including the "cargo" effector peptide if any) is usually the advantageous feature in applications. However, since the permeability of a fraction of the entire construct, e.g. the VHH or the VHH-comprising polypeptide excluding the effector peptide, is relevant to the permeability of the entire construct, the permeability may alternatively, or in addition, be assessed (measured and/or calculated) for the entire construct or a fraction thereof, especially the VHH and/or VHH-comprising polypeptide excluding the effector peptide.

In a particular embodiment of the invention, the polypeptide, in particular the VHH or the VHH-comprising polypeptide is basic.

In Particular Embodiments, the Polypeptide of the Invention is Basic.

A protein, particularly a VHH, is said to be basic when its isoelectric point (pI) is higher than 7, more preferably equal to or higher than 8 and even more preferably equal to or higher than 8.5 or equal to or higher than 9. The pI of a protein is defined as the pH at which the protein carries no net charge (i.e. the negative charges compensates the positive charges). Methods to determine the pI of a protein, either through experimental determination or through theoretical calculation based on the sequence of the protein, are known to the skilled person. In particular, the pI can be measured experimentally using isoelectric focusing. Alternatively, or in addition, the pI may be calculated using a computer program such as the EMBOSS iep software, available from the European Bioinformatics Institute, Genome Campus, Hinxton, Cambridge CB10 1SD, UK and/or the Compute PI tool from the Expasy software, available from the Swiss Institute of Bioinformatics, Quartier Sorge—Batiment Genopode, 1015 Lausanne, Switzerland. Since the pI of the entire construct (i.e. the entire VHH-comprising polypeptide of the invention, including the "cargo" effector peptide if any), as well as the pI of a fraction thereof, e.g. the VHH or the VHH-comprising polypeptide excluding the effector peptide, is relevant to the permeability of the entire construct across the BBB, the pI may alternatively, or in addition, be assessed (measured and/or calculated) for the entire construct or a fraction thereof, especially the VHH and/or the VHH-comprising polypeptide excluding the effector peptide.

In particular embodiments, the VHH of the invention, possibly excluding other peptides forming the VHH-comprising polypeptide of the invention, has a pI equal to or higher than 8, more preferably equal to or higher than 8.5 and even more preferably equal to or higher than 9. In particular embodiments, the VHH-comprising polypeptide of the invention, preferably including the cargo peptide, has a pI equal to or higher than 8, more preferably equal to or higher than 8.5 and even more preferably equal to or higher than 9.

A peptide with a high pI is likely to bind cells non-specifically, thus preventing its targeting to specific cells. In a particular embodiment, the VHH of the invention, possibly excluding other peptides forming the VHH-comprising polypeptide of the invention, has a pI equal to or lower than 11, more preferably equal to or lower than 10.5 and even more preferably equal to or lower than 10. In particular embodiments, the VHH-comprising polypeptide of the invention, preferably including the cargo peptide, has a pI equal to or lower than 12, more preferably equal to or lower than 11 and even more preferably equal to or higher than 10.5. Preferred ranges for the pI of the VHH of the invention, possibly excluding other peptides forming the VHH-comprising polypeptide of the invention are 8.5-11, 8.5-10, 9-10 and 9-10.5. Preferred ranges for the pI of the VHH-comprising polypeptide of the invention are 8.5-12, 8.5-11, 9-11, 9-10.5, 9.5-10.5 and 10-10.5.

The inventors provide herein a VHH obtained from an alpaca. This VHH has the sequence of SEQ ID NO:3 and is encoded by a polynucleotide with the sequence of SEQ ID NO:4. This VHH was shown by the inventors not to recognize any brain antigen, to have a basic pI (pI>9), to be permeable across the BBB at least in the form of VHH-comprising polypeptides as detailed in the examples section (in particular VHH1, VHH2, VHH3).

In a particular embodiment, the polypeptide of the invention targets neuron cells. In particular the polypeptide is a fusion polypeptide wherein the VHH is fused to a molecule that targets neuron cells.

The VHH of the Invention May be Fused with a Neuron Cell-Targeting Peptide.

Some peptides have the capacity to target a polypeptide of the invention to specific cell types, i.e. the polypeptide comprising them is preferably associated to and/or transported to and/or bound to specific cells. In particular, such peptides targeting neurons are known in the art. Such peptides may originate from a Rabies virus G protein. Such peptides, with the sequence of SEQ ID NO:1 are within the scope of the invention to illustrate them. Variants of these sequences are also encompassed within the invention as neuron cell-targeting peptide provided they exhibit the same targeting properties and are derived from the above sequences by point mutation(s) affecting 10% or less of amino acid residues, for example by conservative substitution of amino acid residues. Other suitable neuron cell-targeting peptides derived from a Rabies virus G protein include peptides with a sequence chosen among the group of SEQ ID NO:32, SEQ ID NO:33 and SEQ ID NO:34.

In particular embodiments, the VHH or VHH-comprising polypeptide of the invention is targeted to neuron cells, in particular is targeted to neuron cells in the device of the invention after crossing the layer of endothelial cells. The targeting may be reflected by the presence of said polypeptide at the surface of and/or inside neuron cells, either exclusively or in higher quantities relatively to other cell types and/or polypeptide in solution (not bound to cells).

Of note, in the art, as discussed below, the introduction of a cysteine in a chimeric construction comprising a VHH would usually be avoided in order to preserve the monomeric presentation of the VHH, thought to be required for its activity. However, the cysteine in neuron cell-targeting peptides derived from a Rabies virus G protein is required to maintain its biological activity (Lentz et al., 1987). Therefore, in a preferred embodiment, the VHH-comprising fusion polypeptide of the invention comprises a peptide, in particular such a neuron cell-targeting peptide, comprising a cysteine residue, in particular such a peptide fused N-terminally to the VHH moiety, and in particular such a cysteine residue is found 5 to 25, preferably 10 to 20 and most preferably 16 residues N-terminally to the first (N-terminal) residue of the VHH moiety.

According to a particular embodiment, the polypeptide of the invention has dimerization capacity, in particular homodimerization capacity and preferably wherein homodimerization results from disulphide bridge(s).

The VHH or VHH-Comprising Polypeptide of the Invention May have Dimerization Capacity.

The invention thus encompasses a VHH or VHH-comprising polypeptide as a dimer construct. A VHH obtained from Camelidea itself usually cannot form dimers, in particular homodimers, which is thought to be one of their characteristics and required features to exert biological function. Therefore, the skilled person designing a VHH or VHH-comprising polypeptides would usually design it to preserve its monomeric structure. However, in the case of the presently disclosed VHH-comprising polypeptide, the inventors have surprisingly found that the biological activity differed between monomeric and dimeric forms (presentations) and that the latter was preferable.

Methods to allow for the formation of dimers are known to the skilled person. In particular, such methods comprise the addition of dimerization domains, especially homodimerization domains of known dimeric proteins. Alternatively (or in addition), the presence of cysteine residues in the sequence of the VHH (e.g. by mutation of another amino acid in the sequence) or the presence of cysteines in one or more peptides bound to said VHH in the polypeptide of the invention may enable the VHH or VHH-comprising polypeptide of the invention to form dimers, especially homodimers. The skilled person will appreciate that said cysteines must be comprised in a region of the sequence such that they are accessible to binding by another polypeptide when the polypeptide is in its folded conformation. In particular embodiments, the VHH or VHH-comprising polypeptide of the invention is provided as a dimer and in particular homodimer. In particular embodiments, the VHH or VHH-comprising polypeptide of the invention comprises one or more cysteine residues which can form intermolecular disulphide bonds. In particular embodiments, the dimer-forming (especially homodimer-forming) cysteine(s) lies in the N-terminal extremity of the VHH or VHH-comprising polypeptide, and in particular it/they lie(s) in a peptide N-terminal to the VHH and in particular in a neuron-targeting peptide fused N-terminally to the VHH, such as the RDP disclosed herein.

According to a particular embodiment, the polypeptide of the invention is a VHH-comprising polypeptide and accordingly is a fusion polypeptide comprising any of the VHH defined herein, possibly fused with the molecules disclosed herein and comprising additionally a fused effector polypeptide.

The VHH-Comprising Polypeptide of the Invention May Comprise a Neurovita Peptide.

The VHH or VHH-comprising polypeptides (particularly comprising a neuron cell-targeting peptide and/or a tag as described herein) of the invention was designed to be used as a vehicle to transport a neurovita peptide (also called herein cargo or effector molecule or peptide) across the blood-brain barrier (and possibly to target the cargo peptide to a given cell, cellular compartment, . . . ).

The preferred linkage to the VHH-comprising polypeptide of the invention acting as vehicle is through the generation of a fusion polypeptide comprising the VHH or VHH-comprising polypeptide vehicle and the effector peptide. The term VHH-comprising polypeptide therefore includes, except where excluded by the context or technically irrelevant, and the invention encompasses, fusion polypeptides comprising a VHH of the invention and a neurovita peptide. In preferred embodiments, the cargo peptide has less than 40, less than 30 and preferably less than 20 amino acids. The skilled person will also appreciate that the pI of the cargo peptide may influence the pI of the fusion polypeptide comprising the vehicle and cargo. As stated elsewhere herein, the resulting VHH-comprising polypeptide of the invention is preferably basic.

Peptides derived from the G protein of a Rabies virus, which have an effect on the survival and/or protection and/or motility of neurons and/or which promote neurite outgrowth are cargo molecules according to the invention. They have been disclosed in WO 2013/068430. These peptides are disclosed as cytoplasmic domains of peptides, said cytoplasmic domains consisting of a cytoplasmic domain upstream of the MAST2-binding domain and a MAST-2 binding domains in said publication. The term "Neurovita peptides" as used herein designates such a cytoplasmic peptide, comprising or consisting of a MAST2-binding domain and a sequence upstream thereof (i.e. N-terminal, the MAST2-binding domain being fused C-terminally to said upstream sequence). In particular embodiments, a Neurovita peptide is a 30 to 55 amino acid peptide derived from the cytoplasmic domain of a G protein of a Rabies virus, comprising the MAST2-binding domain of said G protein and having an effect on the survival, protection and/or mobility of neurons and/or which promotes neurite outgrowth. An example of such a peptide to carry out the invention is the peptide with the sequence of SEQ ID NO:7. Such peptides are preferably fused C-terminally to the VHH of the invention, and preferably to any other peptide forming part of the VHH-comprising polypeptide, so that the MAST2-binding domain is at the C-terminal extremity of the VHH-comprising polypeptide of the invention. In particular embodiments, the VHH-comprising polypeptide of the invention comprises fusion polypeptides comprising VHH and a Neurovita peptide, preferably fused C-terminally to the VHH, more preferably at the C-terminal extremity of the polypeptide of the invention.

The Neurovita peptides, and in particular the preferred Neurovita peptide with the sequence of SEQ ID NO:7, have a basic pI. In particular, the pI of the Neurovita may be 12 or more. The skilled person would appreciate that a peptide with such a basic pI is likely to bind cells non specifically, and would therefore not consider using such a peptide in particular if it is meant to be targeted to specific cells. The inventors have found, however, that when used in fusion with a VHH which is less basic, in particular with a pI in the 9.5 to 10 range and particularly with pI=9.86, no non-specific binding of the VHH-comprising polypeptide, having a pI in the 10-10.5 range, and particularly with pI=10.36, is observed, and the polypeptide is specifically targeted. In particular embodiments, the Neurovita peptide has a pI of 12 or more. In particular embodiments, the VHH-comprising polypeptide, comprising a Neurovita peptide, has a pI of 12 or less, preferably of 11 or less, more preferably of 10.5 or less, and in particular a pI comprised in the 8.5 to 11 range, preferably in the 9 to 10.5 range and most preferably in the 10-10.5 range. In particular, the VHH-comprising polypeptide, comprising a Neurovita peptide, has a pI of 10.36.

Neurovita peptides may carry any of the MAST2-binding domains disclosed in pages 12-22 of WO 2013/068430 A1, and each group disclosed therein constitutes a group from which to select the MAST2-binding domain of the Neurovita peptide of particular embodiments. Similarly, the MAST2-binding domain of Neurovita peptides in particular embodiments of the present invention may be selected among the MAST2-binding domain of Neurovita peptides defined in particular embodiments in p. 12-22 of WO 2013/068430. In preferred embodiments, VHH-comprising polypeptide comprises the Neurovita peptide having the sequence of SEQ ID NO:7. The MAST2-binding domain of Neurovita peptides individually disclosed in pages 15, 16, 18, 20 and 21 of WO 2013/068430 each are included in a preferred embodiment. In particular, the MAST-2 binding domain of the neurovita polypeptide of the invention consists of a sequence, whose size is from 11 to 13 residues, the first two residues of which are S and W, and the fourth last residues of which are Q, T, R and L (these 4 last amino acid residues represent the so-called PDZ-BS).

The MAST-2 binding domain is defined according to one of the following groups, knowing that, whatever the group, the first two amino acid residues of the MAST-2 binding domain are S and W and the last four amino acid residues of the MAST-2 binding domain are Q, T, R and L: (A) in a first group, the MAST-2 binding domain consists of a sequence, whose size is 11 residues, the first two residues of which are S and W, and the last four residues of which are Q, T, R and L, consisting of SWX1X2X3X4X5QTRL, wherein each of X1, X2, X3, X4 and X5 is any amino acid residue (SEQ ID NO:21); (B) in a second group, the MAST-2 binding domain consists of a sequence, whose size is 11 residues, the first two residues of which are S and W, and the last four residues of which are Q, T, R and L, which may be obtained by deletion of two amino acid residues, consecutive or not, from the SWESHKSGGQTRL sequence (SEQ ID NO:19) (C) In a third group, the MAST-2 binding domain consists of a sequence, whose size is 12 residues, the first two residues of which are S and W, and the last four residues of which are Q, T, R and L, consisting of SWX1X2X3X4X5X6QTRL, wherein each of X1, X2, X3, X4, X5 and X6 is any amino acid residue (SEQ ID NO:22); (D) in a fourth group, the MAST-2 binding domain consists of a sequence, whose size is 12 residues, the first two residues of which are S and W, and the last four residues of which are Q, T, R and L, which may be obtained by deletion of one amino acid residue from the SWESHKSGGQTRL sequence (SEQ ID NO:19) and (E) In a fifth group, the MAST-2 binding domain consists of a sequence, whose size is 13 residues, the first two residues of which are S and W, and the last four residues of which are Q, T, R and L, consisting of SWX1X2X3X4X5X6X7QTRL, wherein each of X1, X2, X3, X4, X5, X6 and X7, is any amino acid residue (SEQ ID NO:23).

The sequence of the binding domain upstream of the MAST2-binding domain in the neurovita peptide of the invention can be any of the sequences disclosed in pages 22 to 24 of WO 2013/068430 for the equivalent purpose in said application. In particular, such a sequence may contain 20 to 40 amino acid residues, preferably 25 to 45 residues, and particularly 31 residues. In particular embodiments, the sequence of the cytoplasmic domain upstream of the MAST-2 binding domain is a fragment of the cytoplasmic domain of a rabies virus G protein, in particular a fragment of the cytoplasmic domain of a G protein from an attenuated rabies virus strain or a fragment of the cytoplasmic domain of a G protein from a virulent rabies virus strain; more particularly, the sequence of the cytoplasmic domain upstream of the MAST-2 binding domain consists of the following sequence RRVNRSEPTQHNLRGTGREVSVTPQSGKIIS (SEQ ID NO:17) or a variant thereof as described in the above-cited publication, in particular RRVNRSEPTQLNLRGTGREVSVTPQSGKIIS (SEQ ID NO:18).

Particular examples of neurovita polypeptides of the invention are selected in the group consisting of:

```
                                    (SEQ ID NO: 20)
RRVNRSEPTQHNLRGTGREVSVTPQSGKIISSWESHKSGGQTRL
(Neurovita 1);

(SEQ ID NO: 24)
RRVNRSEPTQHNLRGTGREVSVTPQSGKIISSWEVHGGQTRL
(Neurovita 2);

(SEQ ID NO: 7)
RRVNRSEPTQHNLRGTGREVSVTPQSGKIISSWEVHGQQTRL
(Neurovita 3);

(SEQ ID NO: 25)
RRVNRSEPTQHNLRGTGREVSVTPQSGKIISSWEVATQQTRL;

(SEQ ID NO: 26)
RRVNRSEPTQHNLRGTGREVSVTPQSGKIISSWEVYTGQTRL;

(SEQ ID NO: 27)
RRVNRSEPTQHNLRGTGREVSVTPQSGKIISSWEVHTGQTRL;

(SEQ ID NO: 28)
RRVNRSEPTQHNLRGTGREVSVTPQSGKIISSWEVHTQQTRL;

(SEQ ID NO: 29)
RRVNRSEPTQHNLRGTGREVSVTPQSGKIISSWEVAGGQTRL;

(SEQ ID NO: 30)
RRVNRSEPTQHNLRGTGREVSVTPQSGKIISSWAEAQHTQQTRL;
and (SEQ ID NO: 31)
RRVNRSEPTQHNLRGTGREVSVTPQSGKIISSWEVHASGGQTRL.
```

In particular embodiments, the neurovita peptide of the VHH-comprising polypeptide of the invention may also be rendered inactive by the deletion of its PDZ-BS sequence (the last four amino acid residues of the MAST2-binding domain). Such a neurovita peptide has either reduced or no biological activity and may be used e.g. as a reference to test the specific effect of a neurovita peptide in a VHH-comprising polypeptide of the invention. A particular inactivated neurovita peptide is NV delta-PDZ-BS with the sequence of RRVNRSEPTQHNLRGTGREVSVTPQSGKIISSW-EVHGQ SEQ ID NO:9).

In a particular embodiment, the polypeptide of the invention additionally comprises a tagging peptide and/or additionally comprises a peptide spacer, in particular inserted between the VHH and the effector polypeptide, and/or additionally comprises an affinity peptide.

The VHH or VHH-Comprising Polypeptide of the Invention May Comprise Additional Peptides Such as Tags or Spacers.

The skilled person will appreciate that the inclusion in the VHH-comprising polypeptide of peptides with specific functions, in addition to the targeting peptide and/or effector peptide described herein, can be advantageous. These comprise e.g. spacer peptides, tagging peptides and affinity peptides (and peptides having the features of both spacer peptides and tagging peptides). The VHH-comprising polypeptide of the invention may comprise one or more of such peptides. Such peptides are well known to the skilled person and only a brief description is provided herein. The skilled person will appreciate that the choice of peptide and of their position in the fusion protein should be made so that essential features of the fusion polypeptide in respect of the invention are not significantly altered. In particular, the pI should preferably remain basic, wherever possible the additional peptide should not modify the size range of the resulting polypeptide, and the addition of the peptide should not result in aggregation or sequestration (e.g. by binding to a specific cellular component) of the resulting VHH-comprising polypeptide.

A spacer peptide consists in a few amino acids which are intercalated between two defined peptides or polypeptides in a fusion protein, usually in order to allow each peptide/polypeptide to fold independently of the other, or relatively independently, i.e. in order to allow each peptide/polypeptide to adopt a conformation similar to its conformation when it is not fused to the other peptide/polypeptide. A spacer peptide in may consist in a single amino acid, or a stretch of 2, 3, 4 or 5 amino acids, or 6 to 10 amino acids or 11 to 20 amino acids.

A tagging peptide, is usually used to facilitate purification and/or detection of the fusion polypeptide. In some cases, the tagging peptide is detectable by itself (e.g. fluorescent tags such as GFP) while in other cases the tagging peptide is detectable because it specifically binds a detectable molecule (in turn, the detectable molecule may be directly detectable, e.g. fluorescent, or it may be detected by specific binding to it of a detectable molecule, i.e. a scaffold of molecules may be required for detection). If used for purification and/or indirect detection, such a peptide is usually designed (or found) to have a high affinity to a readily available molecule. Such peptides are often derived from a species unrelated to the species where the polypeptides is intended to be used to avoid any cross reaction, especially during detection. The molecule binding the tagging peptide may be selected for its detectability and/or for ease of immobilization and/or recovery in purification processes. Common tagging peptide include HA-tag (a short peptide from human influenza hemagglutinin), Flag-tag, His-tag (comprising at least 6 histidine residues) and the Strep-tag (comprising eight amino acids and which is readily bound by commercially available Strep-tactin and antibodies). In particular embodiments, the VHH-comprising polypeptide of the invention comprises a Strep-tag with the sequence of SEQ ID NO:5, in particular fused C-terminally to the VHH, particularly intercalated between the VHH and effector peptide.

In a particular embodiment, the invention thus relates to a VHH-comprising polypeptides which comprises the fusion of an RDP sequence, such as SEQ ID NO:1, a VHH sequence, such as SEQ ID NO:3, a tag sequence, such as SEQ ID NO:5 and a Neurovita sequence, such as SEQ ID NO:7.

In a particular embodiment, the polypeptide of the invention has the sequence of SEQ ID NO:11 or of SEQ ID NO:45.

It should be noted that, while the fusion of a peptide presents some advantages in particular in terms of ease of production, the functions of a tagging peptide may also be obtained by linking a non-peptidic moiety to a polypeptide and the use of such moiety is contemplated herein and the invention encompasses polypeptides bound to such moieties. The term "tag" therefore comprises tagging peptides as well as non-peptidic moieties with similar functions. The skilled person will appreciate that the term "tag" specifically in the context of a polypeptide should be interpreted as "tagging peptide", while in contexts where it is technically relevant reference to a "tagging peptide" must be understood to comprise a non-peptidic tag.

Methods for the preparation of VHH and VHH-comprising polypeptides of the invention are disclosed herein and are part of the invention. In particular embodiments, the method for producing a VHH of the invention comprises the steps of:

A—obtaining a VHH, in particular with the sequence of SEQ ID NO:3 or a sequence variant thereof or a portion thereof as defined herein, or a polynucleotide encoding such VHH;

B—designing or selecting a polypeptide or a subset of polypeptides consisting of or comprising said VHH which has/have a basic pI and optionally designing or obtaining a [subset of] polynucleotide(s) encoding said polypeptide(s) and/or selecting a VHH which does not recognize any brain antigen, or does not bind any brain protein, in particular human brain antigens and proteins;

C—designing or selecting a polypeptide or a subset of polypeptides consisting of or comprising said VHH which is/are permeable across the BBB and optionally designing or obtaining a [subset of] polynucleotide(s) encoding said polypeptide(s).

Steps B, and C may alternatively be carried out in a different order.

A—Obtaining a VHH, with the sequence of SEQ ID NO:3 or a sequence variant thereof or a portion thereof as defined herein, or a polynucleotide encoding such VHH can be achieved according to methods known to the skilled person. In particular embodiments, obtaining such a VHH comprises the steps of:

obtaining the cDNAs with the sequence of SEQ ID NO:4, optionally obtaining fragments, in particular PCR fragments comprising portions of said cDNAs, especially portions comprising the CDR regions of the VHH with the sequence of SEQ ID NO:3, using said cDNAs as templates, optionally introducing mutations in said fragments, e.g. by introducing the desired mutations in the PCR primers;

cloning said fragments, in particular PCR fragments in vectors, in particular in plasmids suitable for expression in bacteria, optionally fusing said fragment in frame together with nucleic acid sequences encoding peptides, e.g. neuron cell-targeting peptides, effector peptides, and/or tagging/spacer peptides as described herein;

expressing the encoded polypeptide, especially fusion polypeptide in determined cells.

Subsequent selection steps may be performed in either order. With the objective to minimize cost and maximize success rate, the skilled person will appreciate that the more high-throughput selection steps should usually be performed before lower-throughput steps (as the subset will tend to comprise less possible clones after each selection step), and that the selection steps relative to the less frequent feature should be performed before selection steps for more common features (as it is more likely to find a common feature in a clone selected for a rare feature than the other way around). It will also appear that more common features, or features that are easier to select for, that increase the probability of finding a less common feature (or one less easy to select for) should be selected for first. Accordingly, it will appear to the skilled person that the selection for pI should usually be performed before the selection for permeability through the blood-brain barrier.

It must also be reiterated that, where relevant and not explicitly excluded, a VHH-comprising polypeptide of the invention can be substituted for a VHH of the invention in the described methods. In particular, the selection steps below may be performed on a VHH-comprising polypeptide instead of a VHH. The selection step may also be performed both on the VHH and on the VHH-comprising polypeptide in the course of preparing such a polypeptide. In a particular embodiment, a subset of VHH is selected that have a basic pI, then a subset of VHH-comprising polypeptides as described herein is prepared, that each comprises one of the selected VHH, preferably with the same additional peptides and/or modifications, and only then a step of selecting a VHH-comprising polypeptide that is permeable across the BBB is performed. The skilled person will appreciate that the step of selecting a VHH that does not recognize a brain antigen will usually be performed with the VHH alone (i.e. not fused to another peptide) and will usually not need to be repeated after modification, including fusion of other peptides, as the modifications are usually unlikely to generate the capacity for the VHH in the VHH-comprising peptide to recognize a brain antigen. In contrast, the skilled person will appreciate that, while it may be advantageous to include a step of selecting a VHH alone that is permeable across the BBB, further modifications of the VHH to generate the VHH-comprising polypeptide are likely to modify permeability so that is appears optional to perform the selection on the VHH alone, while this step will advantageously be performed (or performed again) on the VHH-comprising polypeptide.

B—Selecting or designing a polypeptide consisting of or comprising said VHH that has a basic PI can be performed by calculating the pI from the sequence of said VHH or VHH-comprising polypeptide, or by in vitro experiments such as isoelectric focusing. The skilled person can easily derive methods to test the pI of a polypeptide produced in bacteria in vitro. The preferred method, however, is based on the sequence of the polypeptide. The pI can be calculated according to algorithms known to the skilled person such as the EMBOSS iep software, available from the European Bioinformatics Institute, Genome Campus, Hinxton, Cambridge CB10 1SD, UK and/or the Compute PI tool from the Expasy software, available from the Swiss Institute of Bioinformatics, Quartier Sorge—Batiment Genopode, 1015 Lausanne, Switzerland.

Selecting a VHH which does not recognize any brain antigen, in particular any human brain antigen, or which does not specifically bind any brain protein, in particular any human brain protein, may be performed using methods known to the skilled person. As the skilled person would appreciate, an antigen which does not recognize any human brain antigen, or which does not bind any human brain protein, may be understood as one which does recognize an antigen or bind a protein which is found solely, or in majority, in the brain, vs. human cells of other origin. In particular, a VHH which recognizes an antigen outside the human brain may correspond to this definition. It will also appear to the skilled person that such absence of recognition and/or binding may be understood as the absence of significant recognition and/or binding, i.e. a recognition or binding the skilled person would consider biochemically relevant. In particular, said significant recognition and/or binding may be relative to antigens or proteins from non-brain origin, which may be formulated as a specific recognition/binding of/to a human brain antigen/protein. In particular embodiments, the VHH of the invention does not produce specific staining in western blotting assays using whole human brain extract (Sg tau 4697), mouse brain extracts (Tg 4510) and/or GFAP, in particular in conditions allowing brain-antigen specific VHHs to produce staining, in particular using the western blotting procedures disclosed herein and in particular using the VHH fused with a Strep tag. In particular embodiments, the VHH of the invention does not produce specific staining in immunohistochemistry assays using Tg 4510 mouse brain tissue, in conditions where a brain antigen-specific antibody produces significant staining, in particular in the conditions disclosed herein. In particular embodiments, the VHH of the invention does not produce specific staining by western blotting or by immunohistochemistry as above.

C—Selecting or designing a polypeptide consisting of or comprising said VHH that is permeable across the BBB will usually be performed initially through in vitro experiments. Indeed, no known sequence features or other directly accessible parameters of the polypeptide allows to predict the permeability across the BBB, while direct testing in vivo would likely appear unreasonable in terms of ethics and cost. Methods that allow to test for the permeability of the VHH or VHH-comprising polypeptide of the invention comprise methods mentioned above in the description of the VHH of the invention. In particular, these methods comprise the novel method of testing the permeability across the BBB disclosed in the present application which makes use of the novel device developed by the inventors and also disclosed herein. This method of testing, disclosed in more detail below, is encompassed in the invention, both by itself as a "testing method of the invention" and as a step in particular embodiments of the method of preparing a polypeptide of the invention. In selecting a VHH or VHH-comprising polypeptide of the invention, the skilled person will find guidance to use the method in the present application. In particular, specific technical features (including experimental conditions) of the method using the device of the invention are disclosed in the examples section below and constitute preferred embodiments of the method to prepare a VHH or VHH-comprising polypeptide of the invention. In using methods of the prior art, in particular based on devices of the prior art with similar presentation as the device of the invention, the skilled person will appreciate that similar experimental conditions are likely to be successful and make use of the teachings herein to perform the step of selecting a VHH or VHH-comprising polypeptide that is permeable across the BBB.

The invention also relates to a polynucleotide encoding the polypeptide disclosed herein and its components (VHH, peptide targeting molecule, neurovita, tag, spacer), in particular a polynucleotide comprising the sequence of SEQ ID NO:4 or a portion of said sequence.

Methods of obtaining nucleic acids encoding the VHH with the sequence of SEQ ID NO:3 are known to the skilled person as well as methods of obtaining nucleic acids encoding a portion of said VHH, a VHH with at least 80%, 90%, or 95% identity with said VHH, fusion proteins comprising said VHH (VHH-comprising polypeptides of the invention). Said nucleic acids encoding a VHH or VHH-comprising polypeptide of the invention, and said methods of obtaining said nucleic acids, are encompassed in the invention. In particular embodiments, the nucleic acids encoding the VHH or VHH-comprising polypeptide of the invention comprise or consist of:

the sequence of SEQ ID NO:4 or the sequence of another nucleic acid encoding a VHH of the invention;

optionally, the sequence of a nucleic acid encoding a neuron cell-targeting peptide, preferably the sequence of SEQ ID NO:2;

optionally the sequence of a nucleic acid encoding a tagging peptide, preferably the sequence of SEQ ID NO:6;

optionally, the sequence of a nucleic acid encoding a neurovita peptide, preferably the sequence of SEQ ID NO:8 or the sequence of any of the neurovita peptide-encoding nucleic acids disclosed in WO2013/068430, particularly on pages 32-35, or the sequence of an inactive neurovita peptide, preferably with the sequence of SEQ ID NO:10.

In preferred embodiments, the nucleic acid encoding a neuron cell-targeting peptide, if present, is in 5' of the nucleic acid encoding the VHH, and/or the nucleic acid encoding the neurovita peptide, if present, is in 3' of the nucleic acid encoding the VHH. In preferred embodiments, the nucleic acid encoding the VHH or VHH-comprising polypeptide of the invention has a sequence selected among SEQ ID NO:4, SEQ ID NO:12, SEQ ID NO:14, SEQ ID NO:16 or the sequence of SEQ ID NO:46. In particular embodiments, the nucleic acids encoding a VHH-comprising polypeptide of the invention exclude nucleic acids found in nature, in particular exclude nucleic acids found in camelids, in particular nucleic acids consisting of a nucleic acid encoding a VHH obtained or obtainable from a camelid. In particular embodiments, the sequence of the nucleic acid encoding a VHH or VHH-comprising polypeptide of the invention comprises, in addition to the sequence of a nucleic acid encoding a VHH, at least two nucleotides, preferably at least three nucleotides and more preferably at least 9, 18, 30, 60 or 120 in nucleotides, forming a sequence which is not found in camelid and/or otherwise in nature. In particular embodiments, the sequence of the nucleic acid encoding a VHH or VHH-comprising polypeptide of the invention comprises, in-frame and immediately adjacent to the sequence of a nucleic acid encoding a VHH, a stop codon forming a sequence which is not found in camelid and/or otherwise in nature and is significantly and/or functionally different from such a camelid or natural sequence, since in particular it encodes a protein which is truncated relative to naturally-occurring proteins. In particular embodiments, the sequence of the nucleic acid encoding a VHH or VHH-comprising polypeptide of the invention comprises in its coding sequence a codon which is not found in camelids.

The invention is also directed to vectors comprising nucleic acids encoding a VHH or VHH-comprising polypeptide of the invention. Such vectors are known to the skilled person and include expression vectors for expression of the VHH or VHH-comprising polypeptide in bacteria (including *E. coli*), or other prokaryotic cells or cell lines or yeast or other eukaryotic cells or cell lines, especially mammalian cells or cell lines and also include as cloning vectors, including plasmids and phagemids, designed for ease of genetic engineering (optimized e.g. for the cloning and/or maintenance of nucleic acid, especially cDNA, libraries, for the generation of nucleic acids encoding fusion proteins, . . . ). Particularly preferred vectors of the invention (or for use in the method of producing the polypeptide of the invention) are plasmids comprising a peptide signal such as ompA that direct the expressed protein into the periplasmic space and is cleaved off during the translocation process, such as the pASK-IBA2 plasmid available from IBA GmbH, Rudolf-Wissell-Str. 28, D-37079 Goettingen, Germany. The vectors of the invention also comprise virus-derived vectors, including lentiviral vectors. In particular embodiments, the vectors comprising nucleic acids encoding a VHH of the invention exclude phagemid vectors encoding a VHH obtained or obtainable from a camelid.

The invention is also directed to cells and cell lines comprising a VHH or VHH-comprising polypeptide of the invention, a nucleic acid of the invention encoding such a polypeptide or a vector of the invention comprising such a nucleic acid. These cells may be selected in the group of bacteria (including *E. coli*) or other prokaryotic cells or cell lines or yeast or other eukaryotic cells or cell lines, especially mammalian cells or cell lines.

The invention is also directed to compositions comprising any of the following compounds: a VHH or VHH-comprising polypeptide of the invention, a nucleic acid of the invention encoding such a polypeptide, a vector of the invention comprising such a nucleic acid and/or a cell or cell line of the invention comprising such a polypeptide, nucleic acid and/or vector. Compositions comprising a large number of different VHH, or VHH-encoding sequences, may not carry the technical effect of the invention, especially when a fraction of said VHH do not have the feature of the VHH of the invention. Therefore, in particular embodiments, the composition of the invention comprises a limited number of different VHH or VHH-comprising polypeptides, and/or nucleic acids encoding a limited number of different VHH, wherein a limited number is no more than 100, preferably no more than 20 or 10 and even more preferably no more than 5, 4, 3, 2 or 1. In a preferred embodiment, a composition of the invention is a solution comprising a VHH or VHH-comprising polypeptide of the invention and comprising no more than 1, 2, 3, 4 or 5 different VHH and/or VHH-comprising polypeptides. The cited compounds are in association with a physiologically acceptable vehicle suitable for in vivo administration in the composition.

The invention is also directed to pharmaceutical compositions, suitable for in vivo administration, in particular for intravenous injection or ophthalmic administration, comprising any of the following compounds: a VHH or VHH-comprising polypeptide of the invention, a nucleic acid of the invention encoding such a polypeptide, a vector of the invention comprising such a nucleic acid and/or a cell or cell line of the invention comprising such a polypeptide, nucleic acid and/or vector, wherein said compound is in association with pharmaceutically acceptable adjuvants and/or solvents and/or carriers. Compositions suitable for in vivo administration can be prepared according to methods known to the skilled person. In particular embodiments, the pharmaceutical composition of the invention is an injectable solution or an eye drop solution. In particular embodiments, the pharmaceutical composition of the invention comprises as active ingredient a VHH or a VHH-comprising polypeptide, wherein the VHH preferably has the sequence of SEQ ID NO:3, and a neurovita peptide, preferably with the sequence of SEQ ID NO:7, fused C-terminally to said VHH. In preferred embodiments, the pharmaceutical composition of the invention comprises as active ingredient a VHH-comprising polypeptide comprising a VHH, a Neurovita peptide and a neuron cell-targeting peptide, preferably with the sequence of SEQ ID NO:1 or SEQ ID NO:32, fused N-terminally to said VHH.

The invention is also directed to an agent (designated as "the agent of the invention") consisting of any of the following compounds: a VHH or VHH-comprising polypeptide of the invention, a nucleic acid encoding such a polypeptide, a vector comprising such a nucleic acid, a cell or cell line comprising such polypeptide, nucleic acid and/or vector, or a pharmaceutical composition comprising said polypeptide, nucleic acid, vector and/or cell or cell line, wherein said agent of the invention is for use as a medicament and/or in the preparation of a medicament. The invention also comprises methods of treating a host, especially a human patient, in need thereof using an agent of the invention. In particular embodiments, the VHH-comprising polypeptide for use of the invention comprises a VHH, preferably with the sequence of SEQ ID NO:3 and a Neurovita peptide, preferably with the sequence of SEQ ID NO:7, fused C-terminally to said VHH. In preferred embodiments, the VHH-comprising polypeptide for use of the invention comprises a VHH, a Neurovita peptide and a neuron cell-targeting peptide, preferably with the sequence of SEQ ID NO:1 or SEQ ID NO:32, fused N-terminally to said VHH.

In particular embodiments, the treatment of the invention comprises injecting intravenously the agent of the invention and/or the medicament is for intravenous injection. In particular embodiments, the treatment of the invention comprises administering the agent in the eye (ophthalmic administration) and/or the medicament is presented as eye drops. In particular embodiments, the agent of the invention is for use in (or for the preparation of a medicament for) the treatment of a human subject. In particular embodiments, the agent of the invention has an advantageous and/or therapeutic effect on brain cells. In particular embodiments, the agent of the invention is for use in, and/or for the preparation of a medicament for, the treatment of a CNS or brain disease or condition. Specific diseases contemplated include neuronal, in particular neurodegenerative diseases. Specific conditions contemplated include brain stroke, injury, glaucoma, trauma or lesion, induced by extrinsic or intrinsic (to the individual) factors. In preferred embodiments, the agent of the invention comprises a VHH-comprising polypeptide comprising or consisting of a VHH, preferably with the sequence of SEQ ID NO:3 and a Neurovita peptide, preferably with the sequence of SEQ ID NO:7, fused C-terminally to said VHH and optionally a neuron cell-targeting peptide, preferably with the sequence of SEQ ID NO:1 or SEQ ID NO:32, fused N-terminally to said VHH, and the agent is for use in the treatment of (or for the preparation of a medicament for) neuronal diseases, in particular neurodegenerative diseases or brain stroke, glaucoma, trauma, lesion or injury.

Further teachings regarding the production of camelid antibodies, and modifications thereof, in particular for use in therapeutic applications, are disclosed in Harmsen and De Haard, 2007.

The device of the invention is similar in presentation to devices disclosed in the prior art, e.g. in Weksler et al., 2005, U.S. Pat. No. 8,084,254 B2 and WO 2006/056879, in that it consists of or comprises a container suitable for cell culture comprising one or more confluent layers, preferably monolayers, of endothelial cells, said monolayers separating the cell culture container in two compartments. In contrast to devices of the prior art, the device of the invention is a blood-brain barrier in vitro model characterized in that the device comprises cells of human origin including, in one of the compartments, microglial cells. The cells comprised in the device are preferably all human cells. At least some of the cells of the device, particularly the endothelial cells, are preferably immortalized cells. Preferably, the cells of the device are all human immortalized cells.

As used herein, "human cells" designates cells of human origin, i.e. derived from cells initially found in a human. In preferred embodiments, the cells are not obtained by direct sampling of a human. Instead, cells sampled from a human are cultured in conditions allowing the production of cells suitable for in vitro studies, including in sufficient number and sufficiently homogenous for such studies, which share most characteristics of the cells found in a human and in particular of which the genomic DNA consists or essentially consists of sequences found in human genomic DNA. Thus, "human cells" may designate immortalized cells obtained from cells directly sampled in a human, possibly after a selection process. "Human cells" may also designate cells obtained from the culture and/or differentiation of stem cells, whether human embryonic stem cells, human adult stem cells, including pluripotent and/or undifferentiated cells obtained by techniques known to the skilled person. In particular embodiments, the provision of the cells of the device does not involve in vivo procedures on a human. In particular embodiments, the cells of the devices are not obtained through the destruction of human embryos. Likewise, "brain cells" designates cells of brain origin, i.e. derived from cells of samples from brain tissue and sharing essential characteristics with cells found in the brain.

The container for cell culture may be e.g. a cell culture tube, vial or flask or, preferably, the well of a multi-well plate for cell culture, especially 12-well and 24-well plates. In a particular embodiment, the device of the invention comprises a multi-well plate, preferably a 12-well or 24-well plate, for cell culture, each well constituting a container (comprising two compartments separated by a layer of endothelial cells, one compartment comprising microglial cells), such a device allowing to run separate experiments simultaneously. The container is preferably coated with conventional coatings used in the culture of adherent cells, preferably poly-D-lysine-laminin.

The monolayer of cells may be grown on a physical substrate which is permeable to liquids and macromolecules, such a as filter suitable for cell culture. The growing of cells on such a filter allows to position the layer of cells such that it separates the cell culture container in two compartments. Since the cell layer is intended to mimic the BBB, one of the compartments corresponds to the brain, while the other compartment corresponds to the general blood flow. The former is sometimes referred to herein as the "brain compartment", while the latter is referred to as the "injection compartment". The term "injection compartment" is used for simplicity and is not intended to limit the device or uses thereof to applications where a test substance is applied in said compartment, and in some setups it might be preferable to apply the test substance in the brain compartment.

The endothelial cells forming the separation layer in the device are preferably human cells, preferably immortalized human cells. In particular embodiments, the endothelial cells forming the separation layer are immortalized human cerebral endothelial cells. In particular, such cells may be obtained by immortalization of human cerebral microvascular endothelial cells as described in Weksler et al., 2005, and/or have similar properties to the hCMEC/D3 cell line disclosed in said publication, or the endothelial cells may be from the hCMEC/D3 cell line. Alternatively, other human immortalized BBB endothelial cell lines such as hBMEC, TY10, and BB19 could be used. The separation layer(s) is/are preferably monolayers and is/are confluent, i.e. no space is left between cells in the (mono)layer(s). In order to prepare a confluent layer of cells, cells should usually be seeded in smaller number than required for confluence and left to grow, usually for several days, until they reach confluence. The layer of cells is positioned in such a way that the separation between the compartments is impermeable to passive diffusion of macromolecules and/or so that any molecule transported from one compartment to the other must do so through the cell layer.

The microglial cells in the device of the invention are present in the brain compartment. Said cells are preferably human cells, preferably human immortalized cells. Such cells may consist of CHME-5 cells or similar cells obtained by immortalization of human foetal microglia by the T antigen of SV40 (as described in e.g. Peudenier et al., 1991). Alternatively, primary cells may be used (e.g. available commercially from ScienCell 6076 Corte Del Cedro, Carlsbad, Calif.—92011, USA). The cells in the brain compartment may either have no contact with the endothelial cells forming the separation layer, or may be cultivated in contact with said layer. According to a particular embodiment, the endothelial cells and the microglial cells are not in contact and the microglial cells are positioned opposite from the endothelial cells, in their compartment.

The brain compartment of the device may comprise other cell types in addition to microglial cells. The additional cells are preferably human, preferably human immortalized cells or cells obtained from human immortalized cells. In particular, other cell types such as other brain cells in particular neurons or astrocytes or both may be present in the brain compartment. Human Neurons and astrocytes may be obtained by differentiation of Ntera-2clD/1 cells (available from ATCC, with the reference CRL-1973) as described in PaquetDurand et al., 2003, Sandhu et al., 2003 and in the examples section. Alternatively, primary cells may be used.

An alternative source of cells, SK-N-SH D cells, in particular for the production of the device of the invention, is disclosed herein. These cells, a clone isolated from the neuroblastoma cell line SK-N-SH (ATCC HTB-11), acquire the features of neuron cells, in particular when cultivated in EndoGRO™ medium (EndoGRO™-LS # SCME 001 or EndoGRO™-MV # SCME004; Merck-millipore, France), while they are routinely grown and maintained in conventional cell culture medium such as DMEM Glutamax-I-High Glucose-Na Pyr. Such cells are therefore convenient to grow and maintain and may in a short time be differentiated into neuron cells by transferring them in the appropriate differentiation medium, such as EndoGRO™, which differentiation medium may also be used as the incubation medium of the model. The invention therefore provides the SK-N-SHD cell line, deposited at the CNCM (Collection Nationale de Culture de Microorganismes, Institut Pasteur, Paris, France) on 4 Sep. 2015, under the number CNCM 1-5010. These cells are provided in particular for use as neuron cell models, e.g. to assay the effect of pharmacological compounds on said cells. More particularly, these cells are provided for use in the manufacture of a device of the invention, particularly for seeding in the brain compartment. In any of the embodiments disclosed herein, the device of the invention may comprise, in its brain compartment, SK-N-SH D cells.

In the art, the use of microglial cells in the brain compartment of a BBB model is usually avoided, in particular due to their inflammatory nature and their BBB disruption capacity (see e.g. Carvalho da Fonseca et al., 2014). However, the inventors have surprisingly shown that a device of the invention may comprise (or be seeded with) 15% or more and even 24% or more of microglial cells in the brain compartment, without any significant impairment of its functions as a BBB. In particular, BBB models of the invention seeded with 1.5% to 24% of microglial cells have been shown to be functional. Such a model with 80% or more of microglial cells is also fully functional.

In the brain, microglial cells represent from 1.5% to 24% of cells, depending in particular on the region of the brain (Kettenmann and Ransom, 2012), and the device of the invention has been shown to be functional with 1.5% or 24% of microglial cells relative to the total cell content of the brain compartment. The quantification and mixing of cells is preferably performed when seeding the cells in the brain compartment, since at this stage cells need to be trypsinized to recover them from the cell culture and seed them. However, since little cell division or death is expected to occur during the period from the seeding of cells to experimental use of the device, the ratio established at the time of seeding may be a close approximation, or an underestimate, of the final ratio in the device.

In a particular embodiment, the microglial cells represent 1.5% of cells in said compartment. In a particular embodiment, the microglial cells represent 24% of cells in said compartment. In another particular embodiment, the microglial cells represent 15% of cells in said compartment. In particular embodiments, the microglial cells represent 1.5% to 15%, 1.5% to 24%, or from 5% to 20% or from 10% to 20% of cells in said compartment. In particular embodiments, the microglial cells represent 1.5% to 5% or 20% to 24% of cells in the brain compartment.

The skilled person will appreciate that the ratio of microglial cells in the brain compartment may vary as cells grow in said compartment, in particular since the different types of cells may have different growth and/or survival rates. In particular embodiments, the device of the invention contains the above ratio of microglial cells in the brain compartment at the time of addition of cells (in other words, brain compartment of the device of the invention is seeded with cells comprising microglial cells in the above-disclosed ratio to the total cell content). In particular embodiments, the ratio of microglial cells is 24% or more, 50% or more, 75% or more in the brain compartment when the device of the invention is used for an assay. The ratio may be measured at the beginning of the assay and/or the ratio may be assayed at the end of the assay. Preferably, the ratio stays in the following ranges during the entire assay: 10% to 100%, 15% to 100%, 24% to 100%, 50% to 100%, 70% to 100% or 80% to 100%. In a particular preferred embodiment, the device is seeded with a 15% ratio of microglial cells in the brain compartment and this ratio is 80% or higher two days after seeding.

Generally speaking, the methods to cultivate, manipulate and maintain cells required to prepare the device of the invention are readily known to the skilled person. Specifically, however, since co-culture of endothelial cells, such a hCMEC/D3, and of microglial cells, such as CHME, was never achieved in the prior art, the inventors have developed specific culture conditions. In particular embodiments, the cells of the device of the invention are in (or the cell culture container contains) a cell culture medium comprising EBM-2, supplemented with fetal bovine serum, hydrocortisone, bFGF, ascorbic acid, chemically defined lipids, HEPES and optionally penicillin-streptomycin, preferably in quantities which do not significantly differ from those disclosed in the examples section, particularly do not differ by more than 50%, preferably not by more than 25%, 10% or more preferably 5%. In particular embodiments, the brain or the injection compartment, or both compartments of the device of the invention contain EndoGRO™-LC or EndoGRO™-MV (Merck-millipore, France) medium, or any medium suitable for the differentiation of SK-N-SHD cells into neuronal cells. In preferred embodiments, both compartments contain the same culture medium. Additional guidance regarding cell culture and manipulations may be found in the publications cited herein and in the Examples section.

Specific technical features and experimental conditions disclosed in the Examples section define preferred embodiments of methods to prepare a device and/or of the device of the invention.

In a particular embodiment the microglial cells (and possibly other brain cells) are not in contact with the monolayer of endothelial cells and/or the filter on which such cells are seeded, or are not in close proximity to said cells or filter.

In another embodiment, the microglial cells are positioned under the endothelial cells and/or the filter or in close proximity thereof.

Methods of preparation of a device of the invention are encompassed in the invention.

Said methods will usually comprise the steps of:
Obtaining endothelial cells, preferably human immortalized endothelial brain cells;
Seeding said endothelial cells on a filter suitable for cell culture and then
Growing said cells to confluence on said filter;
And the steps of:
Obtaining microglial cells, preferably human immortalized microglial cells;
Optionally, obtaining other brain cells, especially neurons and/or astrocytes, especially neurons and astrocytes obtained by differentiation of human immortalized brain cells, in particular Ntera-2clD/1 and/or SK-N-SHD cells;
Seeding said microglial cells, optionally together with the other brain cells, in a container suitable for cell culture, and preferably filling said container with EBM-2 medium supplemented as described above;

And then the steps of:

Providing, in particular transporting the filter carrying the confluent layer(s) of endothelial cells in the container where the microglial cells were seeded;

positioning said filter so that it separates said container in two compartments, providing microglial cells and optionally other cells, in particular other brain cells in one of the compartment thus obtained in the container.

Uses of the device of the invention are encompassed in the invention. Such uses comprise any methods where the availability of an in vitro device mimicking the behaviour of the human BBB (an "in vitro model of the BBB" as used herein) can be considered advantageous. Such uses are known by the skilled person and are common in the field of drug development, especially for drugs or drug candidates intended to be used in the treatment of brain diseases or conditions and drugs or substances intended to be used in diagnostics procedures involving the brain, e.g. in brain imaging procedures. The invention therefore comprises the use of a device of the invention as an in vitro model of the BBB, in particular to test the ability of molecules that have crossed the BBB to target other brain parenchyma cells such as microglia, neurons or astrocytes. Particular embodiments are methods of testing, especially methods of testing the permeability of a test substance across the BBB and methods of testing the toxicity of a test substance on the BBB, comprising applying the test substance to the cell culture container of the device of the invention and/or incubating said test substance in the container of the device and determining whether said test substance permeates the BBB and/or has a toxic effect on the BBB and/or is targeted to specific cells of the brain compartment.

The test substance, as will clearly appear to the skilled person, can be any substance, especially one intended for in vivo use (especially in non-human mammalians and/or humans), especially a substance being developed for use a drug or as a diagnostics agent. Quantities of the test substance which may be applied to the device depend on the objective of the testing methods. In particular, since only a fraction of a permeable substance will usually permeate across the BBB in common experimental conditions, the amount initially applied should be such that a fraction (preferably more than 0.1%, more preferably more than 0.5%, 1%, 2.5% or 5% and even more preferably more than 10%) of said amount is readily detectable by methods available for detecting this substance, in testing methods of the permeability of said substance across the BBB. On the other hand, a very large amount of substance may lead to undesired effects, including the saturation of cellular transport mechanisms which allow substance to permeate the BBB or effects due to unspecific or low-affinity binding of the substance to cellular or extracellular components, of no biological or physiological relevance when reasonable amounts of the substance are used, but significant in the presence of large amounts.

For example, for testing permeability, typical amounts of proteins applied in the wells of a device of the invention based on a 12-well plate would be equal to or higher than 0.1 pg, preferably equal to or higher than 1 pg, 2 pg or 5 pg, more preferably equal to or higher than 10 pg and lower than 10 mg, 1 mg, 100 µg, 10 µg or 1 µg, preferably lower than 100 ng, 10 ng or 1 ng.

When testing toxicity, the skilled person will appreciate that the amount of test substance applied should usually reflect at least the highest amount of said substance the BBB is expected to be exposed to in the intended use of said substance. For example, in testing a brain-acting drug, toxicity on the BBB should be tested at amounts significantly higher than the amount that is expected to produce maximum therapeutic effect, in order for the test to allow concluding, when it revealed no toxicity, that the therapeutically efficient amount of substance is not toxic to the BBB. This also holds true when a substance is intended to be used for experimental purpose, including testing for its permeability: testing for toxicity beforehand, with amounts higher than the maximum amount intended to be used in the permeability testing, will allow, if the toxicity test reveals no toxicity, to conclude that the results of the permeability test are not related to a toxic effect. Typically, the amount of substance applied in the toxicity test is 10 times, 5 times, 2 times or 1 time the maximum amount of substance applied or intended to be applied, in permeability testing. In particular embodiments, a testing method of the invention comprises the steps of the method for testing toxicity of a test substance on the BBB and the steps of the method for testing the permeability of said test substance across the BBB, wherein at least the same amount, preferably at least 2 times or 5 times and more preferably at least 10 times the amount, of said test substance is applied to the device of the invention in the toxicity test, relative to the amount in the permeability test.

Testing the permeability of the test substance across the BBB (or the capacity of the test substance to cross the BBB) comprises the step of determining the presence of said test substance in the compartment where it was not applied initially (the "'trans' compartment"), especially the compartment comprising the microglial cells or brain compartment. A reasonable amount of time is usually allowed between the application of the test substance in a compartment and the determination of its presence in the other compartment. Typical times for testing range preferably from 10 min to 4 hours, preferably 10 min, 30 min, 45 min, 1 h, 90 min, 2 h, 3 h or 4 h. In preferred embodiments, the methods is for testing the permeability of said test substance from the general blood flow to the brain and, accordingly, the test substance is applied initially in the injection compartment (i.e. the compartment which does not comprise microglial cells) and its presence is detected in the brain compartment.

Determining the presence of the test substance may or may not involve quantification of the amount of said substance in the 'trans' compartment. Said determination may be performed in situ on the 'trans' compartment, i.e. the contents of the 'trans' compartment or a fraction of said contents are allowed to remain in said compartment for subsequent detection/quantification steps. Alternatively, said determination may be performed after recovery of the contents of said compartment or a sample of said contents, said recovery comprising or consisting of pipetting and/or aspirating and/or otherwise recovering the liquid media in said compartment and/or recovering cells in suspension in said medium and/or recovering, especially by trypsinization, adherent cells from said compartment and transferring said medium and/or cells in a separate container, such as a test tube, for subsequent detection/quantification steps. In particular embodiments, the determination of the presence of said test substance in the 'trans' compartment comprises a step of performing, on the 'trans' compartment or on the contents thereof or a sample of said contents, a method that detects significant amounts of said test substance (but does not detect insignificant amounts), preferably a method that detects non-trace amounts of said test substance (but does not detect trace amounts), and determining whether said test substance is detected or is not detected by said method in the 'trans' compartment. In these embodiments, the method leads to the conclusion that the test substance is permeable across the BBB if said test substance is detected in the 'trans' compartment and vice-versa.

Methods which allow the detection of non-trace amounts (and/or of significant amounts) and that do not allow the detection of trace amounts (and/or of insignificant amounts) include in particular immunohistochemistry, enzyme-linked immunosorbent assay (ELISA), western blotting, radioimmunoassays, PCR in the case of nucleic acids, etc. The skilled person will appreciate that most conventional molecular biology methods of detection may detect a test substance in non-trace amounts (and/or in significant amounts), when adapted through common knowledge in the field while trace amounts (and/or insignificant amounts) will usually not be detected. However, highly sensitive methods such as mass spectrometry or, in the case of nucleic acids, PCR and related methods, especially nested PCR and other methods known to successfully amplify minute amounts of nucleic acids, might lead to the detection of trace amounts and the skilled person will appreciate that such methods might lead to concluding that a substance is permeable when in fact it is not if no lower threshold of quantity is set for the detection. This also applies to some ELISA assays, radioimmunoassays, etc. which have been optimized for the detection of trace amounts of e.g. proteins.

In particular embodiments, the determination of the presence of said test substance in the 'trans' compartment comprises the steps of performing, on the 'trans' compartment or the contents thereof or a sample of said contents, a method that allows the quantification of the amount of said test substance. In such embodiments, quantification, preferably using the same method, may be performed, usually before application of the test substance to the device of the invention, to determine the amount of test substance initially applied and/or quantification, preferably using the same method may be performed to determine the amount of test substance remaining in the compartment where it was initially injected. When accurate measurement of quantity can be obtained through several methods, the same method need not be used to quantify the different fractions. When no suitable method is available or practicable to determine accurate measurement of quantities of the test substance in at least one of the fractions, the same method is preferably used in all fractions in order to estimate relative quantities as accurately as possible.

In such embodiments, the quantity of substance that permeated across the BBB may be expressed in relative terms, either related to the amount of substance initially injected or to the amount of substance that has not permeated. If two of these amounts have been determined, the third can be easily calculated, and both these ratios are easily calculated as well, unless the total amount of detectable substance is modified during the incubation time by e.g. degradation or amplification. If estimated values only can be established, it is usually preferable to overestimate the amount of initially injected substance and to underestimate the amount of permeated substance, so the ratio of permeated to initially injected substance can be expressed as "at least x %". Such embodiments lead to the conclusion that the test substance is permeable across the BBB if at least 0.1%, 0.2% or 0.5% of the initially injected amount of said substance permeated across the separation layer within a reasonable amount of time, preferably if at least 1%, 2% or 3% of said substance permeated, more preferably if at least 5%, 10% or 20% of said substance permeated. Methods that allow the quantification of a test substance are known to the skilled person and comprise western blotting, radioimmunoassays, quantitative ELISA, qPCR or semi-quantitative PCR in the case of nucleic acids, fluorescence-assisted cell sorting (FACS), etc.

Determining the presence of the test substance in the 'trans' compartment may, especially when said substance is applied in the injection compartment, additionally comprise the step of determining in which site of said compartment the substance is found. Site is used here in a broad sense with the meaning of any specific location or type of location or environment, or functional entity which can be described, possibly including the physiochemical state of the substance, e.g. "adsorbed to the surface (or the molecular coating) of the cell culture container", "in solution in the medium", "bound to the cell surface [of a given cell type]", "in a given cellular compartment, e.g. lysosomes", "in complexes containing a given protein", etc. In particular embodiments, the method comprises an additional step of determining whether said test substance is associated with a given cell type, especially is internalized in, and/or bound to the cell surface of, said cell type, especially of a cell type of the brain compartment. In particular embodiments, the method comprises the steps of determining by immunohistochemistry whether a substance is targeted to a given cell type, i.e. is associated with said cell type and not, or significantly less, with other cells in the compartment. Methods allowing to determine the site where a test substance is found are known to the skilled person and include microscopy-based methods (in particular immunohistochemistry, fluorescence microscopy, confocal microscopy, electron microscopy, etc), methods of determining association with a specific cellular compartment involving cellular disruption such as cellular fractionation and/or gradient centrifugation for the separation of said compartments, methods for determining presence of a protein in a multi-protein complex such as immunoprecipitation etc.

Testing the toxicity of the test substance on the BBB comprises the step of determining whether the test substance has a toxic effect on the endothelial cells constituting the separation layer of the device. In another embodiment, testing the toxicity of the test substance on the BBB comprises the step of determining whether the test substance has a toxic effect on the other brain cells present in the container. Said substance is applied to the injection compartment and/or the brain compartment and determination of the toxic effect is usually performed after incubation of the test substance for a given amount of time. Typical incubation times in such methods range preferably from 2 h to 7 days, more preferably from 6 h to 4 days. Incubation times are preferably equal to or longer than 1 h, more preferably equal to or longer than 2 h or 4 h and more preferably equal to or longer than 6 or 12 h. Incubation times are preferably equal to or shorter than 7 days, more preferably equal to or shorter than 6 days or 5 days and even more preferably equal to or shorter than 4 days, 3 days or 2 days. A toxic effect may be detected when cells present reduced viability compared to cells which were not incubated or were incubated in comparable experimental conditions but without application of the test substance (or with the application of a control substance which has no toxic effect on the BBB). Cell viability may be determined using methods known to the skilled person. Other methods of detecting a toxic effect are also known to the skilled person, including detecting and/or quantifying markers of cell death or apoptosis such as proteins and/or genes expressed in cells undergoing cell death or apoptosis and not in viable cells (or expressed in greater quantity than in viable cells).

Although details are given for a method to test for the existence of a toxic effect of a test substance on the endothelial cells or on other brain cells of the device, similar methods apply to test for other biological effect of a test substance on said cells and/or on other cells of the device, in particular the cells of the brain compartment.

EXAMPLES

Example 1: VHH and VHH-Comprising Polypeptide Sequences

The VHH with the sequence of SEQ ID NO:3, named VHH A12, was selected from a VHH immune library. VHH immune libraries have been previously created as described in 1997 by Ghahroudi et al. One Alpaca has been immunized with a human brain hippocampus extract, isolated from an Alzheimer disease patient. This extract contains different proteins. mRNA extracted from circulating B lymphocytes were retrotranscripted. To select cDNA coding only for VHH and not for conventional antibodies, they have been amplified thanks to primers complementary to FR1 and CH2 regions. VHH sequences were cloned in the phagemid pHEN1 in fusion with the phage coat protein III (pIII), and the phagemid used to transform E. coli TG1 bacteria. The expression of recombinant VHH was induced with IPTG. After panning by phage display technology, individual colonies were selected, cultured and tested. When we have selected specific VHH, we performed a digestion step by NcoI and NotI for 3H at 37° C. on the bacteria culture. Digestion products were loaded in an agarose gel and electrophoresis was performed at 180 V for 45 min to separate the insert from the plasmid pHEN1 vector. We recovered the 400 bp fraction corresponding to VHH sequences and performed a ligation with another plasmid pASK-Iba2, previously digested with NcoI and NotI, at 16° C. overnight. For the ligation, ration plasmid/insert was 1/5. Ultracompetent XL2 bacteria (Agilent technologies) were first treated by adding beta-mercaptoethanol and incubated 10 min at 4° C., swirling gently every 2 min. We add 1 μL of DNA (30 ng) and incubated for 30 min at 4° C. A heat-pulse was performed at 42° C. for 30 sec and bacteria were then incubated on ice for 2 min. 500 μL of 2YT were added and cultures were incubated for 1H at 37° C. under stirring. Two hundred of cultures were spread on Petri dishes and incubated overnight at 37° C. The same manipulation was realized to control good transformation of bacteria. A preculture was incubated overnight at 30° C. in 2YT+A. One mL of preculture was used to seed 100 mL of 2YT+A. When OD550 equals 0.5, we add 10 μL of anhydrotetracycline (final concentration: 200 ng/mL) and shake overnight at 20° C. VHH were expressed in bacteria periplasm and they contained a Strep-tag in C-terminal region. Thanks to the tag, we purified them from bacteria extract with an affinity chromatography column, Strep-Tactine Sepharose (Iba), according to manufacturer recommendations. In order to control sample purity, an electrophoresis in polyacrylamide gel could be performed. Proteins were revealed by coloration with Coomassie brilliant blue for 1H at RT under stirring. Then decoloration was fulfilled by successive water bath. Selections were realized with one immune phage display library, Inti against a brain extract from an Alzheimer's disease patient (Sg tau 4697). Among 61 clones isolated with the Sg tau 4697 screening, 2 clones VHH-A12 and VHH-E8 were expressed in E. Coli (FIG. 1) and further characterized.

The NV3-Cyto (NV) sequence (SEQ ID NO:7) is disclosed in WO2013068430 as neurovita 3. Keeping in mind that NV3 has to maintain its free carboxy-terminus (containing the PDZ-BD), the NV3-Cyto sequence has been inserted at the —COOH portion of the neurocargo-neurovita molecule. Said neurovita sequence may be in particular encoded by the nucleic acid with the sequence of:

```
                                            (SEQ ID NO: 8)
CGCCGGGTAAACCGCAGTGAACCGACCCAGCACAATCTGCGTGGGACTGG

TCGTGAGGTGTCCGTTACGCCACAGTCTGGCAAAATCATTAGCTCGTGGG

AAGTaCATGGCCAGCAAACCCGCTTA.
```

Alternatively, in the VHH3 VHH-comprising polypeptide, a neurovita peptide inactivated by deletion of the PDZ-BS is fused at the C-terminal extremity of said VHH-comprising polypeptide. Said inactivated neurovita has the sequence of SEQ ID NO:9 and can be encoded by the nucleic acid with the sequence of:

```
                                            SEQ ID NO: 10)
CGCCGGGTAAACCGCAGTGAACCGACCCAGCACAATCTGCGTGGGACTGG

TCGTGAGGTGTCCGTTACGCCACAGTCTGGCAAAATCATTAGCTCGTGGG

AAGTaCATGGCCAG.
```

A VHH A12 which does not recognize any human brain protein has been isolated from an immunized alpaca phage display. It is well expressed and has a basic pI (9.78). This VHH has the sequence of:

```
                                            (SEQ ID NO: 3)
EVQLQASGGGLAQPGGSLRLSVTVSGSIDVINNMAWYRQAPGNARELVAT

ITSGFSTNYASSVKGRFTISRDNAKKAVYLQMNSLKPEDTADYYSKVHLI

RLGAARAYDYWGQGTQVTVS
``` and can be encoded in particular by the nucleic acid with the sequence of:

```
                                            (SEQ ID NO: 4)
GAGGTGCAGCTGCAGGCGTCTGGGGGAGGCTTGGCGCAGCCTGGGGGGT

CCCTGAGACTCTCCGTAACAGTCTCTGGAAGTATCGATGTTATTAATAA

CATGGCCTGGTACCGCCAGGCTCCAGGGAATGCGCGCGAGTTGGTCGCC

ACAATTACTAGTGGTTTTAGCACAAACTATGCAAGCTCCGTGAAGGGCC

GATTCACCATCTCCAGAGACAACGCCAAGAAAGCGGTATATCTACAGAT

GAACAGCCTGAAACCTGAGGACACGGCCGATTATTACTCTAAGGTTCAC

TTAATACGTCTTGGGGCCGCGCGGGCGTATGACTACTGGGGCCAGGGGA

CCCAGGTCACCGTCTCC.
```

In order to increase the specificity of the nanobody molecule toward neuron cells only, we used the RDP sequences (i.e. Rabies Derived Peptide) derived from the G protein of the CVS-NIV sequence (european patent 09290257.6 (2009), PCTIB2010000967 (2010), U.S. Ser. No. 13/263,050 and US2012100116). Two particular sequences can be used either RDP1 YTIWMPENPRLGM- SCDIFTNSRGKRASKG (SEQ ID NO:1), particularly encoded by the nucleic acid with the sequence of:

```
                                          (SEQ ID NO: 2)
TATACGATTTGGATGCCGGAAAATCCACGTCTGGGCATGTCGTGCGATATC

TTTACCAACAGTCGCGGTAAACGCGCGAGCAAAGGG,
``` or RDP2 KSVRTWNEILPSKGCLRVGGRCHPHVNGGG (SEQ ID NO:32). The two peptides have been designed to contain epitopes involved into the recognition of two different neuronal molecules used by RABV as receptors (LafonM., 2005). In a first set of neurocargo-neurovita molecules, RDP1 only has been tailored. Other neuron cell-targeting peptide that can be used include the peptides with the sequence of: KSVRTWNEIIPSKGCLRVGGRCHPH (SEQ ID NO:33)

or with the sequence of YTIWMPENPRPGTPCDIFTNSRGKRASNG (SEQ ID NO:34).

The VHH-comprising polypeptides contain a strep-tag sequence GGGSAWSHPQFEKAAA (SEQ ID NO:5) to label the molecule, which can be encoded in particular by the nucleic acid with the sequence of:

GGTGGAGGCTCAGCTTGGAGCCACCCGCAGTTC-
GAAAAAGCGGCCGCA (SEQ ID NO:6). It also contains a peptide with the sequence MA (MA peptide), including the initiator methionine (particularly encoded by the nucleic acid with the sequence of: ATGGCC).

The above peptides have been fused in the following order (from N to C-terminal):MA peptide, RDP1, VHH A12, Strep tag, NV. The resulting polypeptide, designated herein VHH1, has the sequence of:

MAYTIWMPENPRLGMSCDIFTNSRGKRASK-
GEVQLQASGGGLAQPGGSLRLSVTVSGSIDVINNMA
WYRQAPGNARELVATITSGFSTNYASSVKGRFTISRD-
NAKKAVYLQMNSLKPEDTADYYSKVHLIRL
GAARAYDYWGQGTQVTVSGGGSAWSHPQFEKA-
AARRVNRSEPTQHNLRGTGREVSVTPQSGKIIS
SWEVHGQQTRL (SEQ ID NO:11). Said polypeptide can be in particular encoded by the nucleic acid with the sequence of:

ATGGCCTATACGATTTGGATGCCGGAAAATC-
CACGTCTGGGCATGTCGTGCGATATCTTTACCAA
CAGTCGCGGTAAACGCGCGAGCAAAGGGGAGGT-
GCAGCTGCAGGCGTCTGGGGGAGGCTTGG CGCA-
GCCTGGGGGGTCCCTGAGACTCTCCGTAACA-
GTCTCTGGAAGTATCGATGTTATTAATAAC
ATGGCCTGGTACCGCCAGGCTCCAGGGAAT-
GCGCGCGAGTTGGTCGCCACAATTACTAGTGGTT
TTAGCACAAACTATGCAAGCTCCGTGAAGGGC-
CGATTCACCATCTCCAGAGACAACGCCAAGAAA
GCGGTATATCTACAGATGAACAGCCTGAAACCT-
GAGGACACGGCCGATTATTACTCTAAGGTTCA
CTTAATACGTCTTGGGGCCGCGCGGGCGTATGAC-
TACTGGGGCCAGGGGACCCAGGTCACCGTC TCCG-
GTGGAGGCTCAGCTTGGAGCCACCCGCAGTTC-
GAAAAAGCGGCCGCACGCCGGGTAAAC
CGCAGTGAACCGACCCAGCACAATCT-
GCGTGGGACTGGTCGTGAGGTGTCCGTTACGC-
CACAGT CTGGCAAAATCATTAGCTCGTGGGAAG-
TACATGGCCAGCAAACCCGCTTATGATAA (SEQ ID NO:12), which includes two stop codons at the 3'end.

As a control, the corresponding molecules lacking the NV3-Cyto PDZ-binding domain (PDZ-BD) (or PDZ-binding sequence, PDZ-BS), designated herein VHH3, or lacking the RDP1 sequence, designated herein VHH2, have been generated. These polypeptides correspond to the following fused peptides and have the following sequences: VHH2: MA peptide, VHH A12, StrepTaq, NV;

```
                                          (SEQ ID NO: 13)
MAEVQLQASGGGLAQPGGSLRLSVTVSGSIDVINNMAWYRQAPGNARELV

ATITSGFSTNYASSVKGRFTISRDNAKKAVYLQMNSLKPEDTADYYSKVH

LIRLGAARAYDYWGQGTQVTVSGGGSAWSHPQFEKAAARRVNRSEPTQHN

LRGTGREVSVTPQSGKIISSWEVHGQQTRL,
``` which can in particular be encoded by the nucleic acid with the sequence of:

ATGGCCGAGGTGCAGCTGCAG-
GCGTCTGGGGGAGGCTTGGCGCAGC-
CTGGGGGGTCCCTGAG ACTCTCCGTAACA-
GTCTCTGGAAGTATCGATGTTATTAATAACATGGC-
CTGGTACCGCCAGGCTC
CAGGGAATGCGCGCGAGTTGGTCGCCACAAT-
TACTAGTGGTTTTAGCACAAACTATGCAAGCTCC
GTGAAGGGCCGATTCACCATCTCCAGAGA-
CAACGCCAAGAAAGCGGTATATCTACAGATGAACA
GCCTGAAACCTGAGGACACGGCCGATTAT-
TACTCTAAGGTTCACTTAATACGTCTTGGGGCCGCG
CGGGCGTATGACTACTGGGGCCAGGGGACCCAG-
GTCACCGTCTCCGGTGGAGGCTCAGCTTGG AGC-
CACCCGCAGTTCGAAAAAGCGGCCGCACGCCGGG-
TAAACCGCAGTGAACCGACCCAGCAC
AATCTGCGTGGGACTGGTCGTGAGGTGTCCGT-
TACGCCACAGTCTGGCAAAATCATTAGCTCGTG
GGAAGTACATGGCCAGCAAACCCGCTTATGATAA
(SEQ ID NO:14), which includes two stop codons at the 3'end;

VHH3: MA peptide, RDP1, VHH A12, StrepTag, NV with deleted PDZ-BD:

MAYTIWMPENPRLGMSCDIFTNSRGKRASK-
GEVQLQASGGGLAQPGGSLRLSVTVSGSIDVINNMA
WYRQAPGNARELVATITSGFSTNYASSVKGRFTISRD-
NAKKAVYLQMNSLKPEDTADYYSKVHLIRL
GAARAYDYWGQGTQVTVSGGGSAWSHPQFEKAAA
RRVNRSEPTQHNLRGTGREVSVTPQSGKIISSW-
EVHGQ (SEQ ID NO:15), which can in particular be encoded by the nucleic acid with the sequence of:

ATGGCCTATACGATTTGGATGCCGGAAAATC-
CACGTCTGGGCATGTCGTGCGATATCTTTACCAA
CAGTCGCGGTAAACGCGCGAGCAAAGGGGAGGT-
GCAGCTGCAGGCGTCTGGGGGAGGCTTGG CGCA-
GCCTGGGGGGTCCCTGAGACTCTCCGTAACA-
GTCTCTGGAAGTATCGATGTTATTAATAAC
ATGGCCTGGTACCGCCAGGCTCCAGGGAAT-
GCGCGCGAGTTGGTCGCCACAATTACTAGTGGTT
TTAGCACAAACTATGCAAGCTCCGTGAAGGGC-
CGATTCACCATCTCCAGAGACAACGCCAAGAAA
GCGGTATATCTACAGATGAACAGCCTGAAACCT-
GAGGACACGGCCGATTATTACTCTAAGGTTCA
CTTAATACGTCTTGGGGCCGCGCGGGCGTATGAC-
TACTGGGGCCAGGGGACCCAGGTCACCGTC TCCG-
GTGGAGGCTCAGCTTGGAGCCACCCGCAGTTC-
GAAAAAGCGGCCGCACGCCGGGTAAAC
CGCAGTGAACCGACCCAGCACAATCT-
GCGTGGGACTGGTCGTGAGGTGTCCGTTACGC-
CACAGT CTGGCAAAATCATTAGCTCGTGGGAAG-
TACATGGCCAGTGATAA (SEQ ID NO:16), which includes two stop codons at the 3'end.

The polypeptide consisting of the fusion of the following peptides in the following order may also be used: MA peptide, RDP1, VHH A12, NV; said polypeptide having the sequence of:

MAYTIWMPENPRLGMSCDIFTNSRGKRASK-
GEVQLQASGGGLAQPGGSLRLSVTVSGSIDVINNMA
WYRQAPGNARELVATITSGFSTNYASSVKGRFTISRD-
NAKKAVYLQMNSLKPEDTADYYSKVHLIRL
GAARAYDYWGQGTQVTVSRRVNRSEPTQHNLRGT-
GREVSVTPQSGKIISSWEVHGQQTRL (SEQ ID NO:45)
and particularly being encoded by the nucleic acid with the sequence of:

ATGGCCTATACGATTTGGATGCCGGAAAATC-
CACGTCTGGGCATGTCGTGCGATATCTTTACCAA
CAGTCGCGGTAAACGCGCGAGCAAAGGGGAGGT-
GCAGCTGCAGGCGTCTGGGGGAGGCTTGG CGCA-
GCCTGGGGGGTCCCTGAGACTCTCCGTAACA-
GTCTCTGGAAGTATCGATGTTATTAATAAC
ATGGCCTGGTACCGCCAGGCTCCAGGGAAT-
GCGCGCGAGTTGGTCGCCACAATTACTAGTGGTT
TTAGCACAAACTATGCAAGCTCCGTGAAGGGC-
CGATTCACCATCTCCAGAGACAACGCCAAGAAA
GCGGTATATCTACAGATGAACAGCCTGAAACCT-
GAGGACACGGCCGATTATTACTCTAAGGTTCA
CTTAATACGTCTTGGGGCCGCGCGGGCGTATGAC-
TACTGGGGCCAGGGGACCCAGGTCACCGTC
TCCCGCCGGGTAAACCGCAGTGAACCGACCCAG-
CACAATCTGCGTGGGACTGGTCGTGAGGTGT
CCGTTACGCCACAGTCTGGCAAAATCATT-
AGCTCGTGGGAAGTACATGGCCAGCAAAC-
CCGCTTA TGATAA (SEQ ID NO:46), which includes two stop codons at the 3'end.

All the constructs have been generated by the standard procedures used in genetic engineering (as described briefly in Préhaud C. et al, 2010).

Strikingly, the sequences of the VHH A12 disclosed herein show some divergence to sequences of VHHs of the prior art, even at residues where the latter show relatively strong conservation.

Example 2: Cloning and Expression of Neurocargo-Neurovita Molecules

The neurocargo-neurovita gene sequences (VHH1: SEQ ID NO:12, VHH2: SEQ ID NO:14, VHH3: SEQ ID NO:16) were synthesized chemically by Eurofin MWG Operon company and inserted in the pASK-IBA2 plasmid (IBA, BioTAGnology, USA) under the control of the tetracycline promoter. In this plasmid the ompA signal sequence directs the expressed protein into the periplasmic space and is cleaved off during the translocation process. In the periplasmic space, disulfide bond-forming proteins which are properly folded can be found. The recombinant plasmids were used to transform XL1-blue E. coli bacteria (Stratagene, USA). Recombinant bacteria were identified by PCR and glycerol stocks were made. VHH-comprising polypeptides were expressed and purified from the bacteria periplasm as described by P. Lafaye (2008). Alternatively, proteins can also be extracted directly from the cytoplasm. The periplasmic extract was further purified by immunoaffinity chromatography using a mouse high affinity anti strep tag mAb such as C23.21 (P. Lafaye, Institut Pasteur biological collection). Expression of VHH-comprising polypeptides was monitored by western blotting using mAb C23.21.

Further, in order to show its dimeric presentation, the purified Neurocargo-neurovita was in resolved in NuPage™ gel (Life Technologies, France) with NuPage MES running buffer either as denatured samples (NuPage™ LDS+DTT+ boiling) or native samples (NuPage™ LDS) according to manufacturer's instruction. The neurocargo-neurovita molecules species were identified by western blotting with the anti strep tag mAb C23.21 (FIG. 1C).

Example 3: Characterization of VHH A12 Neutral

VHH A12 was shown to have the following features: a basic pI (i.e. pI>8.5; in particular 9.86 for the VHH alone and 10.36 for the VHH1 polypeptide); no reactivity against a human brain extract (i.e. Sg tau4697) and a mouse brain extract (i.e. Tg 4510) and GFAP (i.e. glial fibrillary astrocytic protein) by western blotting; and no immunoreactivity on Tg 4510 mouse brain tissue by immunohistochemistry.

Figure 2A:
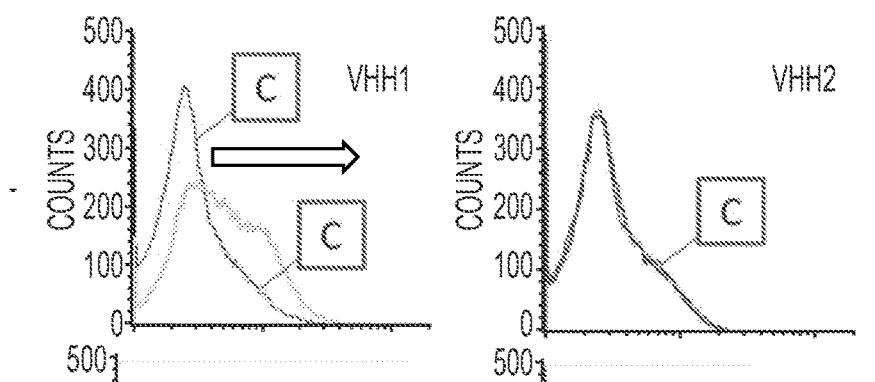
FIG. 2. Binding of VHH-comprising polypeptides to acetylcholine receptor alpha 7 sub-unit (AchR alpha7)
Figure 2B:
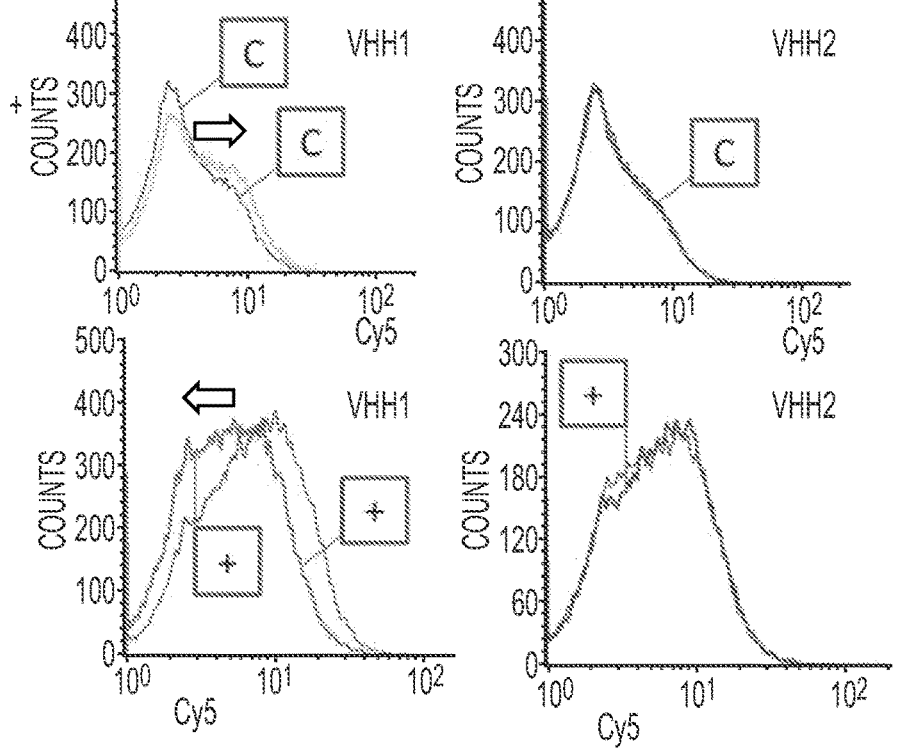
Figure 2C:
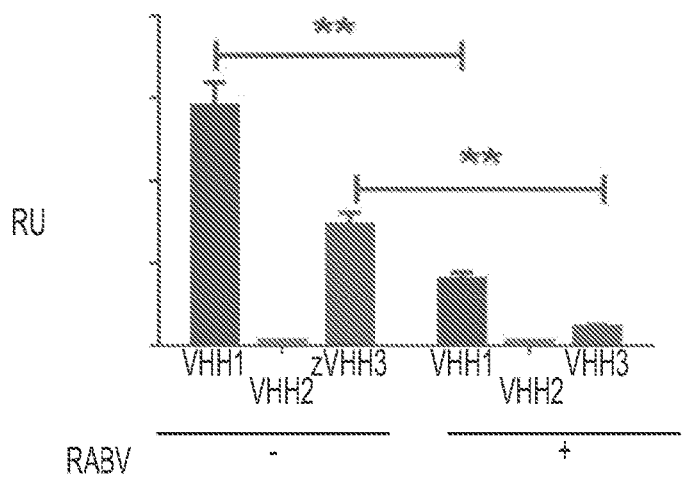

The specificity of the VHH of the invention (A12) as compared to a control VHH recognizing brain proteins (H8/E9, identical to VHH E9, Perruchini et al.) was determined by western blotting on 3 different antigens: a human brain extract (Sg tau 4697), a mouse brain extract (Tg 4510) and on a purified protein, GFAP, a specific marker of astrocytes. As shown in FIG. 2, no bands were detected by VHH A2. Furthermore, VHH immunohistochemistry was performed from Tg4510 mouse tissues (Grueninger et al, 2010) harbouring NFTs. As a control, a specific anti-NFT monoclonal antibody, AT8, showed excellent sensitivity and selectivity for immunodetection of NFTs on Tg 4510 mouse paraffin sections. In contrast, no labelling was observed with VHH A12 (FIG. 1). For western blotting, first we performed a polyacrylamide gel electrophoresis at 200 V for 45 min. Then we transferred proteins from gel to nitrocellulose membrane during 1H at 30 V. We saturated nitrocellulose membrane with PBS milk 2% for 1H under stirring. The membrane was then incubated for 1H with selected VHH diluted at 1 µg/ml in PBS milk 2%, and washed 3 times 5 min with PBS Tween. A secondary mouse mAb C23-21 recognizing Strep-tag (DI 2012-32 High-affinity monoclonal anti-Strep-Tag antibody C23.21; Girard-blanc C., Krey T., Vasiliauskaite ieva, Nato F., Lafaye P., Dartevelle S., Rey F.) was added at 1:2500 and incubated 1H at 37° C. Then after additional washes, an anti-mouse mAb labelled with peroxidase was added for 1 H. Three washes of 5 min in PBS Tween were performed. Next we revealed with photosensible films (Thermo Scientific, Pierce® ECL Western Blotting Substrate) according to manufacturer instructions.

Example 4: Neurites Outgrowth

Neurite outgrowth assays have been extensively described in Préhaud et al., 2010.

Neuroscreen cells (NS cells) are a pC12 subclone. The cells are grown in RPMI medium as described by manufacturer's instructions (http://www.cellomics.com/content/menu/Neuroscreen-1_Cells/). NS cells were monitored for 72 h and treated with 200 ng/ml of NGF a time=0 (one hit only) and neurocargo-neurovita (10 pg, at time=6, one hit only). Neurite outgrowth (NO) was basically undertaken as described for SH-SY5Y with the exception that the NO was monitored 72 h post infection and NS cells were always grown in their feeding medium (Cellomics, USA).

NS cells are imaged using a Cell insight (Cellomics, USA) on quadruplicate wells. The average neurite length per neuron is determined by using the Neuronal profiling bioapplication (Cellomics, USA).

Example 5: Scratch Assay (Axon Regeneration)

For scratch-induced assays, 200 mm2 of NT2-N cells (n=8) were seeded on poly-D-Lysin-laminin coated cell+ (Sarstedt, Germany) 12 wells plasticware, and were grown for two days in order to recover completely after trypsinisation. The medium was changed 4 h before scratching and 10 pg of neurocargo-neurovita was added per well. Individual wounds were made with an injection needle (26 G×½", 12-4.5). At least 10 scratching were made on each individual well. Alternatively the neurocargo-neurovita was added one hour before scratching. Cells were fixed with PFA (4%) 6 days post wounding and stained with crystal violet solution. Cells are imaged using a Leica DM 5000B microscope equipped with a DC 300FX camera (×20 objective) and analysed using ImageJ 1.38X Software (Wayne Rasband, NIH, USA, http://rsb.info.nih.gov/ij/) and its plug-in NeuronJ. The average percentage of neuron in regeneration is determined from 8 experiments.

Example 6: AchR Binding and Competition Assay Monitored by Flow Cytometry, Neurocargo-Neurovita Entry into NS Cells The flow cytometry procedures, which have been followed, have been described in Préhaud et al., 2003. Briefly, Alpha 7 AchR expressing HEK 293 cells (Yamauchi et al., 2011) and parental HEK 293 cells are grown in DMEM high glucose (Life Technologies, France) plus 10% FBS. HEK 293 cells or AchR expressing HEK 293 cells were seeded on 6 well plates (1.e+06 cells per well). 24 hours post seeding, cells were placed on ice and treated with 20 pg of neurocargo-neurovita for 30 mn before being processed for flow cytometry by using staining buffer. Alternatively for the competition assay, cells were treated either with U.V. inactivated 2.e+07 PFU of Rabies virus-CVS strain (as described in Mégret et al., 2005) or 16 µM Alpha bungarotoxin (Sigma, USA). In order to monitor the entry of the neurocargo-neurovita molecules, the same experiments were undertaken but permeabilization buffer was used which allowed detection of both the molecules bound to the receptors and the molecules in the cytoplasm. The neurocargo-neurovita molecules bound to the cytoplasmic membrane receptors were detected with the anti-strep tag mAb described above plus a Cy5 conjugated anti-mouse antibody (Jackson laboratory, USA).

Example 7: Determination of Neuronal Cell (NS) Growth Cone Motility

NS cells were differentiated with 200 ng/ml of NGF a time=0 (one hit only) and neurocargo-neurovita (10 pg, at time=6, one hit only). As a control cells were treated with a bacterial periplasmic extract of bacteria which do not express neurocargo-neurovita. At 48 h, cells were PFA fixed, permeabilized with 0.3% triton X100 and processed for immunofluorescence as already described (Préhaud et al., 2010). Nuclei were detected with Hoescth 33342, βIII Tubulin with a mouse anti beta 3 tubulin antibody (G7121, Promega, France) and an antimouse Alexa 488 antibody (Jackson laboratory, USA), and F actin network with Alexa 546 conjugated phalloidin (A22283, Life Technologies, France).

Example 8: Real Time PCR Analysis of Cellular Gene Expression

The RT-PCR gene expression analysis procedure has been extensively described in Préhaud et al., 2005. Here due to the cell culture plasticware used for the assays, the cDNAs molecules were made with RNA ranging from 200 ng to 1 pg. The primers used in this study are: TH (HSTH1SG, Qiagen, Germany), GFAP (F: CTGCTTCTTAACCCCAG-TAAGCCA (SEQ ID NO: 39), R: GAG CAGTGCCCT-GAAGATTAGCAG (SEQ ID NO:40)), AQP4 (F: GGTATAGTCAATTCTTATTTGAAT (SEQ ID NO:35), R: CTTGAATCTCAATAGGTGCCCTTA (SEQ ID NO:36)), PYGB (F: TCCTGCTGTGTCCTGAGGTGCATT (SEQ ID NO:43), R: GCCCAGATCCAGCATGCAAGGTGC (SEQ ID NO:44)), NEFH (F: CCCCAGGCGATGGACAATTAT-GAT (SEQ ID NO:41), R: CACTTGGTTTTATTGCACA-GAAGC (SEQ ID NO:42)), CD200R (F: TTAACACT-TCATGGCCTGTAAGA (SEQ ID NO:37), R: TGTGCCATTGCTCCAGTATTCTTG (SEQ ID NO:38)), and from Qiagen, Germany (HSSLC2A1-1, HSSLC7A5, HSSLC1A1-1, HSSLC38A5-1, HSSLC16A1, HSSLCO1C1, HSSLCABCB1-1, HSABCG2-1, HSABCC1-1, HSABCC2-1, HSABCC4-1, HSABCC5-1, HSLDLR-1, HSLRP1-1, HSINSR-1, HSLEPR-1, HSPV-LAP-1, HSLU-1, HSTFRC-1, HSAGER1, HSSTRA6-1).

Example 9: Production of an In Vitro Model of the Human BBB

The immortalization of the human cerebral microvascular endothelial cell line (hCMEC/D3) was performed by Weksler et al., 2005. hCMEC/D3 were grown in EBM-2 (Lonza, Switzerland) supplemented with fetal bovine serum (5%, Eurobio, France), hydrocortisone (1.4 uM, Sigma, USA), bFGF (1 ng/mL, Sigma, USA), Ascorbic acid (5 ug/mL, Sigma, USA), chemically defined lipids (1/100, Life technologies, France), HEPES (10 mM, Life technologies, France), penicillin-streptomycin (Life technologies, France). Cells were routinely cultured on rat-tail collagen I (150 ug/mL, R&D systems, U.K.)-coated culture flaks (Corning, USA), and split (via trypsinization) twice a week. A differentiated monolayer was obtained on rat-tail collagen I-(150 ug/mL, R&D systems, U.K.) and fibronectin-(10 ug/mL, Sigma, USA) coated polyester transwells (12 mm diameter, pore size 0.4 µm Corning, USA). Cells were seeded at a density of 25,000 cells/cm² and cultured for 5 days. The culture medium was changed at day 3 of differentiation. At day 5, the in vitro endothelial blood-brain barrier was cultured with the minibrain cells which are seeded on the lower compartment of the device (i.e. minibrain-BBB) or alternatively they were left on medium only (BBB). The minibrain-BBB model therefore comprises, in addition to the endothelial cells, neurons, astrocytes and microglial cells, while the BBB model comprises only the endothelial cells.

CHME microglial cells were grown in DMEM-F12 (Life Technologies, France) plus 10% FBS (Janabi et al., 1995), hNT2N/A (neurons-astrocytes) were differentiated and isolated from the human teratocarcinoma cells NTera/cl2D1, as described by Préhaud et al., 2005, Lafon et al., 2005 and Mégret et al., 2007. hNT2N/A were maintained in DMEM F12 (Life Technologies, France) plus 5% FBS. CHME and hNT2N/A cells were isolated by light tryspsinization and mixed to various ratios, ranging from 0.015 to 0.24, in order to match the microglia vs. neuron-astrocytes ratios of the different areas of brain Kettenmann and Ransom, 2012. These coculture cells, together designated as minibrain cells, were seeded on poly-D-Lysine-laminin coated CellBind plastic ware (Corning, USA), in EBM-2 complete medium (described above). After 24 hours, the transwell containing the monolayer of endothelial cells was added and the system was ready for use 24 hours later.

Example 10: Minibrain-BBB Crossing of Nanobody and Neurocargo-Neurovita Crossing and Targeting Minibrain-BBB device containing 1.5% microglia cells were seeded. One day post seeding, an Alexa 488 conjugated anti GFAP VHH (VHHE9, Li et al., 2012) was applied to the upper chamber (10 pg of nanobody). 3 and 24 hours later, the cells in the lower chamber were PFA fixed, permeabilized with 0.3% triton X100. Photographs were randomly taken (>500) by using the cellinsight (Cellomics, USA). Fluorescent foci were monitored.

Alternatively, for the neurocargo-neurovita molecules, the fluorescent foci were monitored after staining with the anti strep-tag antibody described above and an Alexa 488 conjugated anti-mouse antibody (Life technologies, France).

In order to determine the number of neurons targeted with neurocargo-neurovita molecules, cells were also stained with an anti Neurofilalent 200 KDa antibody (Sigma, USA) and an Alexa 546 conjugated anti-rabbit antibody (Life technologies, France).

Example 11: Determination of the Restrictive Paracellular Permeability with Lucifer Yellow The restrictive paracellular permeability of hCMEC/D3 cells was assessed by their low permeability to the nonpermeant fluorescent marker lucifer yellow (LY) (Sigma Aldrich, L0259). Briefly, after 6 days of culture on filters, hCMEC/D3 monolayers were transferred to 12-well plates containing 1.5 mL of transport medium (HBSS CaMg (Gibco, 14025-supplemented by 10 mM of hepes (Life technologies, 15630-080) and 1 mM of sodium pyruvate (Life technologies, 11360)) per well (abluminal compartment). 0.5 mL transport medium containing 50 µM of LY was then added to the luminal compartment. Incubations were performed at 37° C., 5% $CO_2$, 95% humidity. After 15, 25 and 45 minutes, the inserts were transferred into new wells, beforehand filled with 1.5 mL of transport medium. After 45 minutes, aliquots were taken for each time point, from both compartments and the concentration of LY determined using a fluorescence spectrophotometer (Tecan Infinite F500).

The endothelial permeability coefficient ($P_e$) of LY was calculated in centimetres/minute (cm/min), as described by Siflinger-Birnboim et al. (1987). To obtain a concentration-independent transport parameter, the clearance principle is used. Briefly, the average volume cleared is plotted versus time, and the slope is estimated by linear regression. Both insert permeability ($PS_f$, for insert only coated with collagen) and insert plus endothelial cell permeability ($PS_t$, for insert with collagen and cells) were taken into consideration, according to the following formula: $1/PS_e = 1/PS_t - 1/PS_f$.

The permeability value for the endothelial monolayer was then divided by the surface area of the porous membrane of the insert (Corning, 3460) to obtain the endothelial permeability coefficient ($P_e$) of the molecule (in cm·min-1).

Determination of the Transendothelial Electrical Resistance (TEER)

The TEER of the HCMEC/D3 was determined after 5, 6 and 7 days of culture in Endogro-MV medium (SCME004, Merck Millipore, France) as already described by Weksler et al (2005).

Example 12: The SK-N-SH D Cell Line

The SK-N-SH D cell line is a sub-clone of the ATCC HTB-11 SK-N-SH human neuroblastoma cell line. It has been isolated in differentiating medium as a sub-clone which can naturally differentiate at 100% as neuron-like cells which are beta 3-tubuline and actine-F positive cells. The cell line has been deposited at the CNCM (Institut Patseur, Paris, France) on 4 Sep. 2015, under the reference number 1-5010.

The SK-N-SH D cells are grown routinely in DMEM Glutamax-I-High Glucose (4.5 g/l)-Na Pyr, (Life Technologies, #31966-021) plus 10% fetal calf serum. The cells differentiate spontaneously when transferred either in Endogro-LS (# SCME 001) or Endogro-MV (# SCME004) media (Merck-millipore, France).

BBB models produced using these cells in the brain compartment, and otherwise similar to the above-described models and produced in a similar fashion, have been successfully tested for suitability in the uses disclosed herein.

In particular, a BBB model comprising, HCMEC-D3 and, in the brain compartment, SK-N-SH D cells, was produced and tested following procedures similar as above. A Neurovita-comprising VHH-comprising polypeptide of the invention, when incubated in this model, did not alter permeability as measured by $P_e$. The VHH-comprising polypeptide, comprising the Neuron cell-targeting peptide, was shown by fluorescence microscopy to cross the layer of endothelial cells and to be targeted to the brain cells in the brain compartment. Further models, comprising HCMEC D3 and, in the brain compartment, SK-N-SH D cells (neurons), U 373MG MG (ECACC #08061901) cells (astrocytes, i.e. macroglial cells) and CHME (microglial cells) could also be successfully developed.

BIBLIOGRAPHY

Bicker J, Alves G, Fortuna A, Falcão A. Blood-brain barrier models and theirrelevance for a successful development of CNS drug delivery systems: a review. Eur J Pharm Biopharm. 2014 August; 87(3):409-32. doi: 10.1016/j.ejpb.2014.03.012. Epub 2014 Mar. 28. PubMed PMID: 24686194.

Anna Carolina Carvalho da Fonseca, Diana Matias, Celina Garcia, Rackele Amaral, Luiz Henrique Geraldo, Catarina Freitas and Flavia Regina Souza Lima. The impact of microglial activation on blood-brain barrierin brain diseases. Trends Cell. Neurosci. (2014) doi:10.3389/fnce1.2014.00362

Fu A, Wang Y, Zhan L, Zhou R. Targeted delivery of proteins into the centralnervous system mediated by rabies virus glycoprotein-derived peptide. Pharm Res. 2012 June; 29(6):1562-9. doi: 10.1007/s11095-012-0667-y. Epub 2012 Jan. 10. PubMedPMID: 22231987.

Harmsen M M, De Haard H J. Properties, production, and applications of camelid single-domain antibody fragments. Appl Microbiol Biotechnol. 2007 November; 77(1):13-22. Epub 2007 Aug. 18. Review. PubMed PMID: 17704915; PubMed Central PMCID: PMC2039825.

Grueninger et al, 2010 Neurobiology of Disease 37, 294-306

Janabi N, Peudenier S, Heron B, Ng K H, Tardieu M. Establishment of humanmicroglial cell lines after transfection of primary cultures of embryonicmicroglial cells with the SV40 large T antigen. Neurosci Lett. 1995 Aug. 4; 195(2):105-8. PubMed PMID: 7478261.

Kettenmann H. and Ransom B R. Neuroglia. Oxford University Press, 2012, ISBN 13:9780199794591

Lafon M, Prehaud C, Megret F, Lafage M, Mouillot G, Roa M, Moreau P, Rouas-Freiss N, Carosella E D. Modulation of HLA-G expression in human neuralcells after neurotropic viral infections. J Virol. 2005 December; 79(24): 15226-37. PubMed PMID: 16306594; PubMed Central PMCID: PMC1316015.

Lentz T L, Hawrot E, Wilson P T. Synthetic Peptides Corresponding to Sequences of Snake Venom Neurotoxins and Rabies Virus Glycoprotein Bind to the Nicotinic Acetylcholine Receptor. PROTEINS: Structure, Function, and Genetics 2:298-307 (1987)

Li T, Bourgeois J P, Celli S, Glacial F, Le Sourd A M, Mecheri S, Weksler B, Romero I, Couraud P O, Rougeon F, Lafaye P. Cell-penetrating anti-GFAP VHH and corresponding fluorescent fusion protein VHH-GFP spontaneously cross the blood-brain barrier and specifically recognize astrocytes: application to brain imaging. FASEB J. 2012 October; 26(10):3969-79. doi: 10.1096/fj.11-201384. Epub 2012 Jun. 22. PubMed PMID: 22730440.

Lippmann E S, Al-Ahmad A, Palecek S P, Shusta E V. Modeling the blood-brain barrier using stem cell sources. Fluids Barriers CNS. 2013 Jan. 10; 10(1):2. doi:10.1186/2045-8118-10-2. PubMed PMID: 23305164; PubMed Central PMCID: PMC3564868.

Mégret F, Prehaud C, Lafage M, Moreau P, Rouas-Freiss N, Carosella E D, LafonM. Modulation of HLA-G and HLA-E expression in human neuronal cells after rabies virus or herpes virus simplex type 1 infections. Hum Immunol. 2007 April; 68(4):294-302. Epub 2006 Dec. 28. PubMed PMID: 17400066.

Mégret F, Prehaud C, Lafage M, Batejat C, Escriou N, Lay S, Thoulouze M I, Lafon M. Immunopotentiation of the antibody response against influenza HA with apoptotic bodies generated by rabies virus G-ERA protein-driven apoptosis. Vaccine. 2005 Nov. 16; 23(46-47):5342-50. Epub 2005 Jul. 18. PubMed PMID: 16054731.

Paquet-Durand F, Tan S, Bicker G. Turning teratocarcinoma cells into neurons: rapid differentiation of NT-2 cells in floating spheres. Brain Res Dev Brain Res. 2003 May 14; 142(2):161-7. PubMed PMID: 12711367.

(Perruchini et al, Acta Neuropathologica, 118, 685-695)

Peudenier S, Hery C, Montagnier L, Tardieu M. Human microglial cells: characterization in cerebral tissue and in primary culture, and study of their susceptibility to HIV-1 infection. Ann Neurol. 1991 February; 29(2):152-61. PubMedPMID: 1707249.

Préhaud C, Wolff N, Terrien E, Lafage M, Mégret F, Babault N, Cordier F, Tan G S, Maitrepierre E, Ménager P, Chopy D, Hoos S, England P, Delepierre M, Schnell M J, Buc H, Lafon M. Attenuation of rabies virulence: takeover by the cytoplasmic domain of its envelope protein. Sci Signal. 2010 Jan. 19; 3(105):ra5. doi:10.1126/scisignal.2000510. PubMed PMID: 20086240.

Préhaud C, Megret F, Lafage M, Lafon M. Virus infection switches TLR-3-positive human neurons to become strong producers of beta interferon. J Virol. 2005 October; 79(20):12893-904. PubMed PMID: 16188991; PubMed Central PMCID: PMC1235836.

Préhaud C, Lay S, Dietzschold B, Lafon M. Glycoprotein of nonpathogenic rabies viruses is a key determinant of human cell apoptosis. J Virol. 2003 October; 77(19): 10537-47. PubMed PMID: 12970438; PubMed Central PMCID: PMC228383.

Sandhu J K, Pandey S, Ribecco-Lutkiewicz M, Monette R, Borowy-Borowski H, Walker P R, Sikorska M. Molecular mechanisms of glutamate neurotoxicity in mixed cultures of NT2-derived neurons and astrocytes: protective effects of coenzyme Q10. J Neurosci Res. 2003 Jun. 15; 72(6): 691-703. PubMed PMID: 12774309.

Siflinger-Birnboim A, Del Vecchio P J, Cooper J A, Blumenstock F A, Shepard J M, Malik A B. Molecular sieving characteristics of the cultured endothelial monolayer. J Cell Physiol. 1987; 132:111-117. doi: 10.1002/jcp.1041320115.

Simmons D P, Abregu F A, Krishnan U V, Proll D F, Streltsov V A, Doughty L, Hattarki M K, Nuttall S D. Dimerisation strategies for shark IgNAR single domain-antibody fragments. J Immunol Methods. 2006 Aug. 31; 315(1-2):171-84. Epub 2006 Aug. 28. PubMed PMID: 16962608.

Sumi N, Nishioku T, Takata F, Matsumoto J, Watanabe T, Shuto H, Yamauchi A, Dohgu S, Kataoka Y. Lipopolysaccharide-activated microglia induce dysfunction of the blood-brain barrier in rat microvascular endothelial cells co-cultured with microglia. Cell Mol Neurobiol. 2010 March; 30(2):247-53. doi:10.1007/s10571-009-9446-7. Epub 2009 Aug. 29. PubMed PMID: 19728078.

Weksler B B, Subileau E A, Perrière N, Charneau P, Holloway K, Leveque M, Tricoire-Leignel H, Nicotra A, Bourdoulous S, Turowski P, Male D K, Roux F, Greenwood J, Romero I A, Couraud P O. Blood-brain barrier-specific properties of a human adult brain endothelial cell line. FASEB J. 2005 November; 19(13):1872-4. Epub 2005 Sep. 1. PubMed PMID: 16141364.

Yamauchi J G, Nemecz Á, Nguyen Q T, Muller A, Schroeder L F, Talley T T, Lindstrom J, Kleinfeld D, Taylor P. Characterizing ligand-gated ion channel receptors with genetically encoded Ca2++ sensors. PLoS One. 2011 Jan. 28; 6(1):e16519. doi: 10.1371/journal.pone.0016519. PubMed PMID: 21305050; PubMed Central PMCID: PMC3030600.

The invention claimed is:

1. An in vitro cell culture device comprising a container comprising a filter positioned in such a manner that it separates the container into a first compartment and a second compartment, wherein the filter comprises at least one confluent monolayer of immortalized human endothelial cells on a surface of the filter facing the first compartment and wherein the second compartment does not contain immortalized human endothelial cells and does contain immortalized human microglial cells to thereby provide a functional blood brain barrier model.

2. The device according to claim 1 wherein the filter comprising at least one confluent monolayer of immortalized human endothelial cells forms a separation between the first and second compartments which is impermeable to passive diffusion of molecules transported from one compartment to the other.

3. The device of claim 1, wherein the immortalized human endothelial cells are not in contact with the immortalized human microglial cells and wherein the immortalized human microglial cells are positioned in the second compartment opposite from the filter comprising the immortalized human endothelial cells.

4. The device of claim 1, wherein the immortalized human endothelial cells are immortalized human cerebral endothelial cells.

5. The device of claim 4, wherein the immortalized human cerebral endothelial cells are derived from the cell line hCMEC/D3 deposited at CNCM (Institut Pasteur, Paris, France) on Oct. 7, 2004 under deposit number No. I-3308.

6. The device of claim 1, wherein the immortalized human microglial cells are obtained by immortalization of human foetal microglia by the T antigen of SV40.

7. The device of claim 1, wherein the second compartment containing immortalized human microglial cells further contains at least one other human cell type selected from astrocytes and neurons.

8. The device of claim 7, wherein the at least one other human cell type selected from astrocytes and neurons is derived from the NTera/cl2D1 cell lines.

9. The device of claim 7, wherein the neurons are derived from the SK-N-SHD cell lines, deposited at the Centre Nationale de Collection des Microorganismes (Institut Pasteur, Paris, France) on 4 Sep. 2015, under the number CNCM 1-5010.

10. The device of claim 1, wherein the immortalized human microglial cells represent from 1.5% to 24% of cells in the second compartment.

11. A method for testing the permeability of a test substance across the blood-brain barrier, said method comprising incubating the test substance in a device of claim 1.

12. The method according to claim 11, comprising incubating the test substance in the first compartment of the device, and determining whether the test substance crosses the filter comprising at least one confluent monolayer of immortalized human endothelial cells during the incubation.

13. A method for testing the toxicity of a test substance on endothelial cells, said method comprising (i) applying the test substance to the first compartment of the container of the device according to claim 1, and (ii) measuring the toxic effect on the immortalized human endothelial cells within the first compartment.

14. A method of preparing a cell culture device the method comprising:
  (i) providing a filter carrying at least one confluent monolayer of immortalized human endothelial cells on a surface of the filter in a container,
  (ii) positioning the filter so that it separates the container into a first compartment and a second compartment, wherein the confluent monolayer of immortalized human endothelial cells on the surface of the filter are facing the first compartment, and
  (iii) providing immortalized human microglial cells in a second compartment.

15. The method according to claim 14, wherein the immortalized human endothelial cells are not in contact with the immortalized human microglial cells and wherein the immortalized human microglial cells are positioned in the second compartment opposite from the filter comprising the immortalized human endothelial cells.

16. The method according to claim 14, wherein the immortalized human endothelial cells are immortalized human cerebral endothelial cells derived from the cell line hCMEC/D3 deposited at CNCM (Institut Pasteur, Paris, France) on Oct. 7, 2004 under deposit number No. I-3308.

17. The method according to claim 14, wherein the immortalized human microglial cells are obtained by immortalization of human foetal microglia by the T antigen of SV40.

18. The method according to claim 14, wherein step (iii) further encompasses providing at least one other human cell type selected from astrocytes and neurons derived from the NTera/cl2D1 cell lines in the second compartment.

* * * * *